(12) United States Patent
Asaki et al.

(10) Patent No.: US 7,728,131 B2
(45) Date of Patent: Jun. 1, 2010

(54) AMIDE DERIVATIVE AND MEDICINE

(75) Inventors: Tetsuo Asaki, Uji (JP); Yukiteru Sugiyama, Kyoto (JP); Jun Segawa, Nara (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 249 days.

(21) Appl. No.: 10/584,829

(22) PCT Filed: Dec. 27, 2004

(86) PCT No.: PCT/JP2004/019553

§ 371 (c)(1),
(2), (4) Date: Jul. 10, 2008

(87) PCT Pub. No.: WO2005/063709

PCT Pub. Date: Jul. 14, 2005

(65) Prior Publication Data

US 2008/0293940 A1  Nov. 27, 2008

(30) Foreign Application Priority Data

Dec. 25, 2003 (JP) ............................... 2003-431398

(51) Int. Cl.
*C07D 401/04* (2006.01)
*C07D 401/14* (2006.01)
*C07D 403/04* (2006.01)
*C07D 403/14* (2006.01)
*A61K 31/53* (2006.01)
*A61K 31/506* (2006.01)

(52) U.S. Cl. ...................... 544/182; 544/238; 544/336; 544/356; 544/358; 514/242; 514/252.01; 514/252.12; 514/252.1; 514/272; 514/336

(58) Field of Classification Search ................ 544/182, 544/238, 336, 356, 358
See application file for complete search history.

(56) References Cited

U.S. PATENT DOCUMENTS

| 5,521,184 A * | 5/1996 | Zimmermann ......... 514/252.11 |
| 7,494,997 B2 * | 2/2009 | Asaki et al. ................. 514/242 |
| 2006/0014742 A1 | 1/2006 | Asaki |

FOREIGN PATENT DOCUMENTS

| EP | 0 564 409 A1 | 3/1993 |
| WO | WO 02/22597 A1 | 3/2002 |
| WO | WO 2004/014903 A1 | 2/2004 |

OTHER PUBLICATIONS

S. Kimura, et. al., NS-187, a Potent and Selective Dual Bcr-Abl/Lyn Tyrosine Kinase Inhibitor, is a Novel Agent for Imatinib-Resistant Leukemia, Blood, vol. 16, No. 12, 3948-3954 (Dec. 1, 2005).
T. Asaki, et. al., Design and Synthesis of 3-substituted Benzamide Derivatives as Bcr-Abl Kinase Inhibitors, 16 Bioorganic & Medicinal Chemistry Letters 1421-1425 (2006).
R. Parise, et. al., Liquid Chromatographic— Mass Spectrometric Assay for Quantitation of Imatinib and its Main Metabolite (CGP 74588) in Plasma, 791 J. Chromatography B 39-44 (2003).
B. Druker, et. al., Activity of a Specific Inhibitor of the BCR-ABL Tyrosine Kinase in the Blast Crises of Chronic Myeloid Leukemia and Acute Lumphoblastic Leukemia with the Philadelphia Chromosome, N. Engl. J. Med., vol. 344, No. 14, 1038-1042 (Apr. 5, 2001).
M. Gorre, et. al., Clinical Resistance to STI-571 Cancer Therapy Caused by BCR-ABL Gene Mutation and Amplification, Science, vol. 293 876-880 (Aug. 3, 2001).
MV Blagosklonny, STI-571 Must Select for Drug-Resistant Cells but 'No Cell Breathes Fire Out of its Nostrils Like a Dragon', 16 Leukemia 570-572 (2002).
A. Hochhaus, et. al., Moleculor and Chromosomal Mechanisms of Resistance to Imatinib (STI 1571) Therapy, 16 Leukemia 2190-2196 (2002).
W.K. Hofmann, et. al., Ph+Acute Lymphoblastic Leukemia Resistant to the Tyrosine Kinase Inhibitor STI 1571 has a Unique BCR-ABL Gene Mutation, Blood, vol. 99, No. 5 1860-1862 (Mar. 1, 2002).
M. Deininger, et. al., The Molecular Biology of Chronic Myeloid Leukemia, Blood, vol. 96, No. 10 3343-3356 (Nov. 15, 2000).

* cited by examiner

*Primary Examiner*—Shailendra Kumar
(74) *Attorney, Agent, or Firm*—Troutman Sanders LLP

(57) ABSTRACT

The present invention is directed to an amide derivative having excellent BCR-ABL tyrosine kinase inhibitory activity, or a salt thereof.

The present invention provides an amide derivative represented by the following general formula (1):
[Chemical 23]

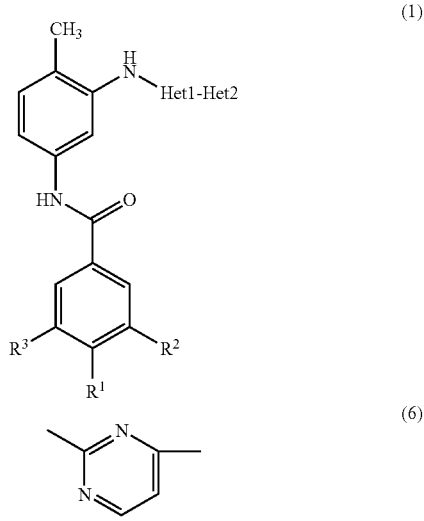

(wherein $R^1$ represents —$CH_2$—$R^{11}$, etc.; $R^2$ represents alkyl, halogen, haloalkyl, etc.; $R^3$ represents hydrogen, etc.; Het1 represents a group of the formula [6] as above, etc.; and Het2 represents pyrimidinyl, etc.), or a pharmaceutically acceptable salt thereof, and a pharmaceutical composition comprising the same as an active ingredient.

The compound of the present invention is useful as a BCR-ABL tyrosine kinase inhibitor.

16 Claims, No Drawings

AMIDE DERIVATIVE AND MEDICINE

This application claims priority from PCT/JP2004/019553, filed Dec. 27, 2004, which claims priority from Japanese Application No. 2003-431398, filed Dec. 25, 2003. Both of those references are incorporated herein in their entirety.

TECHNICAL FIELD

The present invention relates to an amide derivative or a salt thereof, and a pharmaceutical composition comprising an amide derivative or a salt thereof as an active ingredient.

While BCR-ABL tyrosine kinase (see, for example, Non-Patent Document 1) causes aberrant growth of cells, a compound which inhibits its activity is useful for the prevention or treatment of diseases caused by the activity of the BCR-ABL tyrosine kinase, for example, chronic myelogenous leukemia, acute lymphoblastic leukemia and acute myelogenous leukemia (see, for example, Non-Patent Document 2).

BACKGROUND ART ber is a gene which exists in the human twenty-second chromosome and abl is a gene which exists in the human ninth chromosome, and Philadelphia chromosome is formed by translocation of the human twenty-second and ninth chromosomes. It is known that a gene product of the chromosome, BCR-ABL, is a protein having tyrosine kinase activity and constantly generates the growth signal to cause aberrant growth of cells (see, for example, Non-Patent Document 2).

of Cell counting Kit-8 (5 mmol/l WST-8, 0.2 mmol/l 1-Methoxy PMS, 150 mmol/l NaCl) (manufactured by Dojindo) was added to each well. After reaction for color development in a $CO_2$ incubator for 3 hours, an absorbance of formazan, generated by reduction of WST-8 was determined at 450 nm using Multi-level counter ARVOsx (manufactured by Wallac).

In the RPMI-1640/FCS medium containing 0.1% DMSO, when absorbance of a region in which cells after culturing in the $CO_2$ incubator for 72 hours were seeded is defined as a cell growth inhibition rate of 0% and absorbance of a region in which cells were not seeded is defined as a cell growth inhibition rate of 100%, a log conc value in terms of log (inhibition rate/(100−inhibition rate)) and a plotted $IC_{50}$ value (μM) were calculated. The results are shown in Table 3.

As a control drug, 4-(4-methylpiperazin-1-ylmethyl)-N-{4-methyl-3-[4-(3-pyridyl)pyrimidin-2-ylamino]phenyl}benzamide (see Patent Document 1) was used.

TABLE 3

| Test drugs | K562 cells ($IC_{50}$ value: μM) | U937 cells ($IC_{50}$ value: μM) | Ratio (U937 cells/K562 cells) |
|---|---|---|---|
| Example 2 | 0.0028 | 15 | 5357 |
| Example 4 | 0.0020 | 28 | 14000 |
| Example 6 | 0.0012 | 4.3 | 3583 |
| Example 8 | 0.00098 | 4.6 | 4694 |
| Example 10 | 0.0021 | 8.1 | 3857 |
| Example 12 | 0.0056 | 4.7 | 839 |
| Example 14 | 0.0079 | 2.0 | 253 |
| Example 16 | 0.0011 | 4.1 | 3727 |
| Example 18 | 0.0048 | 4.6 | 958 |

Therefore, inhibition of the BCR-ABL tyrosine kinase activity makes it possible to suppress cell growth caused by the kinase and a compound which inhibits the activity is suited for use as a therapeutic agent for diseases such as chronic myelogenous leukemia, acute lymphoblastic leukemia and acute myelogenous leukemia. Although Glivec® (see, for example, Patent Document 1) has already been put on the market as a drug having the same action, other drugs having the same action mechanism have never been put on the market and thus it has been required to develop more excellent medicines.

It has recently been reported that recurrence is often recognized in patients wherein remission is attained by administration of Glivec® in BCR-ABL-positive acute lymphoblastic leukemia, in addition to examples of blastic crisis of chronic myelogenous leukemia (see, for example, Non-Patent Document 3). As a result of examination of leukemia cells of the patients suffering from the recurrence of disease, the appearance of a variant such as E255K is recognized (see, for example, Non-Patent Documents 4 to 7). Also in examples of administration of Glivec® to the patients with BCR-ABL-positive acute lymphoblastic leukemia, the appearance of resistant cells which mainly exhibits variation of E255K is recognized (see, for example, Non-Patent Document 8). With an increase in use of Glivec®, resistant patients further increase and thus it is required to develop a therapy.

Patent Document 1: Japanese Unexamined Patent No. 6-87834
Patent Document 2: Pamphlet of International Publication WO 02/22597
Non-Patent Document 1: Shtivelman E, et al.: Nature, 1985, 315, 550-554
Non-Patent Document 2: Daley G Q, et al.: Science, 1990, 247, 824-830
Non-Patent Document 3: Druker B J, et al.: N Engl J Med, 2001, 344, 1038-1042
Non-Patent Document 4: Weisberg E, et al.: Drug Resist Updat, 2001, 4, 22-28
Non-Patent Document 5: Gorre M E, et al.: Science, 2001, 293, 876-880
Non-Patent Document 6: Blagosklonny M V: Leukemia, 2002, 16, 570-572
Non-Patent Document 7: Hochhaus A, et al.: Leukemia, 2002, 16, 2190-2196
Non-Patent Document 8: Hofmann W-K, et al.: blood, 2002, 99, 1860-1862
Non-Patent Document 9: Deninger W N, et al.: blood, 2000, 96, 3343-3356
Non-Patent Document 10: J. Org. Chem., 1996, 61, 1133-1135
Non-Patent Document 11: J. Org. Chem., 2000, 65, 1144-1157
Non-Patent Document 12: Recl. Trav. Chim. Pays-Bas., 1950, 69, 673-699
Non-Patent Document 13: J. Heterocycl. Chem., 1970, 7, 1137-1141
Non-Patent Document 14: J. Am. Chem. Soc., 1999, 121, 4369-4378
Non-Patent Document 15: Tetrahedron Lett., 1997, 38, 8005-8008
Non-Patent Document 16: J. Med. Chem., 2002, 45, 3406-3417
Non-Patent Document 17: J. Med. Chem., 2000, 43, 3895-3905
Non-Patent Document 18: J. Med. Chem., 2000, 43, 1508-1518
Non-Patent Document 19: J. Med. Chem., 1975, 18, 1077-1088
Non-Patent Document 20: Bioorg. Med. Chem. Lett., 2001, 11, 2235-2239

Non-Patent Document 21: J. Heterocyclic Chem., 2000, 37, 1457-1462

DISCLOSURE OF THE INVENTION

Problems that the Invention is to Solve

An object of the present invention is to provide a novel amide derivative having an excellent BCR-ABL tyrosine kinase inhibitory activity, or a pharmaceutically acceptable salt thereof.

Means for Solving the Problems

The present inventors have intensively studied about various compounds and found that the above object is achieved by a novel amide derivative and a pharmaceutically acceptable salt thereof (hereinafter referred to as a "compound of the present invention"), thereby completing the present invention.

The present invention is directed to an amide derivative, which is a compound represented by the following general formula [1] in any of the following cases (A), (B) or (C), or a pharmaceutically acceptable salt thereof.

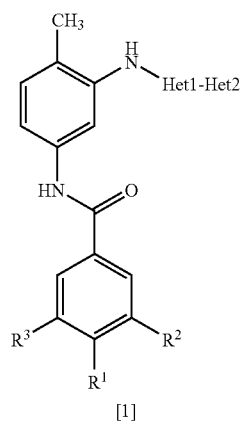

[Chemical 1]

[1]

(A)

$R^1$ represents any of groups of the following (1) through (3):

(1) —$CH_2$—$R^{11}$ [$R^{11}$ represents a saturated, nitrogen-containing heterocyclic group. The saturated, nitrogen-containing heterocyclic group is substituted by a group selected from the group consisting of oxo, —$CH_2$—$R^{111}$ ($R^{111}$ represents a saturated, nitrogen-containing heterocyclic group), a saturated, nitrogen-containing heterocyclic group, aminoalkyl, monoalkylaminoalkyl, dialkylaminoalkyl, alkoxy and (5-methyl-2-oxo-1,3-dioxol-4-yl)methyl, and further, may be substituted by 1 or 2 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl.], (2) —O—$R^{12}$ [$R^{12}$ represents a saturated, nitrogen-containing heterocyclic group. The saturated, nitrogen-containing heterocyclic group may be substituted by 1 to 3 same or different members selected from the group consisting of oxo, —$CH_2$—$R^{121}$ ($R^{121}$ represents a saturated, nitrogen-containing heterocyclic group), a saturated, nitrogen-containing heterocyclic group, aminoalkyl, monoalkylaminoalkyl, dialkylaminoalkyl, alkoxy, (5-methyl-2-oxo-1,3-dioxol-4-yl)methyl, alkyl, alkoxycarbonyl, halogen, haloalkyl, hydroxyalkyl, amino, monoalkylamino, dialkylamino, carbamoyl, monoalkylcarbamoyl and dialkylcarbamoyl.], and (3) —CH=$R^{13}$ [$R^{13}$ represents a saturated, nitrogen-containing heterocyclic group. The saturated, nitrogen-containing heterocyclic group may be substituted by 1 to 3 same or different members selected from the group consisting of oxo, —$CH_2$—$R^{131}$ ($R^{131}$ represents a saturated, nitrogen-containing heterocyclic group), a saturated, nitrogen-containing heterocyclic group, aminoalkyl, monoalkylaminoalkyl, dialkylaminoalkyl, alkoxy, (5-methyl-2-oxo-1,3-dioxol-4-yl)methyl, alkyl, alkoxycarbonyl, halogen, haloalkyl, hydroxyalkyl, amino, monoalkylamino, dialkylamino, carbamoyl, monoalkylcarbamoyl and dialkylcarbamoyl.].

$R^2$ represents alkyl, halogen, haloalkyl, hydroxyalkyl, alkoxy, alkoxyalkyl, alkoxycarbonyl, acyl, amino, monoalkylamino, dialkylamino, nitro, carbamoyl, monoalkylcarbamoyl, dialkylcarbamoyl or cyano.

$R^3$ represents hydrogen, halogen or alkoxy.

Het1 represents any of groups of the following chemical formulas [2] to [8].

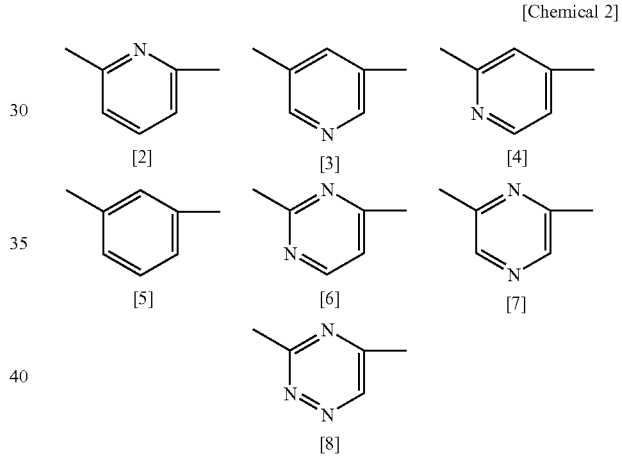

[Chemical 2]

represents pyridyl, pyrimidinyl, pyrazinyl, pyridazinyl or 1,2-dihydropyridazinyl (the Het2 may be substituted by 1 to 3 same or different members selected from the group consisting of alkyl, halogen and amino).

Exception is made for a compound wherein $R^{11}$ is pyrrolidinyl, piperidinyl, piperazinyl or morpholinyl (Each of the pyrrolidinyl, piperidinyl, piperazinyl and morpholinyl is substituted by a group selected from the group consisting of oxo, —$CH_2$—$R^{111}$ ($R^{111}$ represents a saturated, nitrogen-containing heterocyclic group), a saturated, nitrogen-containing heterocyclic group, aminoalkyl, monoalkylaminoalkyl, dialkylaminoalkyl, alkoxy and (5-methyl-2-oxo-1,3-dioxol-4-yl)methyl, and further, may be substituted by 1 or 2 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl); Het1 is a group of the formula [6]; and Het2 is pyrazinyl or pyridyl which may be substituted by alkyl.

(B)

$R^1$ represents —$CH_2$—$R^{14}$ ($R^{14}$ represents a saturated, nitrogen-containing heterocyclic group. The saturated, nitrogen-containing heterocyclic group may be substituted by 1 to 3 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl.).

$R^2$ represents alkyl, halogen, haloalkyl, hydroxyalkyl, alkoxy, alkoxyalkyl, alkoxycarbonyl, acyl, amino, monoalkylamino, dialkylamino, nitro, carbamoyl, monoalkylcarbamoyl, dialkylcarbamoyl or cyano.

$R^3$ represents hydrogen, halogen or alkoxy.

Het1 represents any of groups of the following chemical formulas [9] and [10].

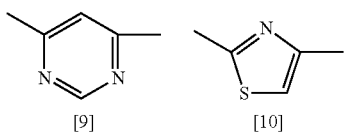

[Chemical 3]

[9]  [10]

Het2 represents pyridyl, pyrimidinyl, pyrazinyl, pyridazinyl or 1,2-dihydropyridazinyl (the Het2 may be substituted by 1 to 3 same or different members selected from the group consisting of alkyl, halogen and amino).

(C)

$R^1$ represents any of groups of the following (1) through (3):

(1) —$CH_2$—$R^{11}$ [$R^{11}$ represents a saturated, nitrogen-containing heterocyclic group. The saturated, nitrogen-containing heterocyclic group is substituted by a group selected from the group consisting of oxo, —$CH_2$—$R^{111}$ ($R^{111}$ represents a saturated, nitrogen-containing heterocyclic group), a saturated, nitrogen-containing heterocyclic group, aminoalkyl, monoalkylaminoalkyl, dialkylaminoalkyl, alkoxy and (5-methyl-2-oxo-1,3-dioxol-4-yl)methyl, and further, may be substituted by 1 or 2 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl.].

(2) —O—$R^{12}$ [$R^{12}$ represents a saturated, nitrogen-containing heterocyclic group. The saturated, nitrogen-containing heterocyclic group may be substituted by 1 to 3 same or different members selected from the group consisting of oxo, —$CH_2$—$R^{121}$ ($R^{121}$ represents a saturated, nitrogen-containing heterocyclic group), a saturated, nitrogen-containing heterocyclic group, aminoalkyl, monoalkylaminoalkyl, dialkylaminoalkyl, alkoxy, (5-methyl-2-oxo-1,3-dioxol-4-yl) methyl, alkyl, alkoxycarbonyl, halogen, haloalkyl, hydroxyalkyl, amino, monoalkylamino, dialkylamino, carbamoyl, monoalkylcarbamoyl and dialkylcarbamoyl.], and (3) —CH=$R^{13}$ [$R^{13}$ represents a saturated, nitrogen-containing heterocyclic group. The saturated, nitrogen-containing heterocyclic group may be substituted by 1 to 3 same or different members selected from the group consisting of oxo, —$CH_2$—$R^{131}$ ($R^{131}$ represents a saturated, nitrogen-containing heterocyclic group), a saturated, nitrogen-containing heterocyclic group, aminoalkyl, monoalkylaminoalkyl, dialkylaminoalkyl, alkoxy, (5-methyl-2-oxo-1,3-dioxol-4-yl) methyl, alkyl, alkoxycarbonyl, halogen, haloalkyl, hydroxyalkyl, amino, monoalkylamino, dialkylamino, carbamoyl, monoalkylcarbamoyl and dialkylcarbamoyl.]

$R^2$ represents alkyl, halogen, haloalkyl, hydroxyalkyl, alkoxy, alkoxyalkyl, alkoxycarbonyl, acyl, amino, monoalkylamino, dialkylamino, nitro, carbamoyl, monoalkylcarbamoyl, dialkylcarbamoyl or cyano.

$R^3$ represents hydrogen, halogen or alkoxy.

Het1 represents any of groups of the following chemical formulas [9] and [10].

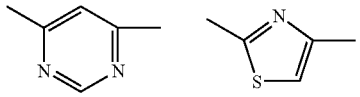

[Chemical 4]

Het2 represents pyridyl, pyrimidinyl, pyrazinyl, pyridazinyl or 1,2-dihydropyridazinyl (the Het2 may be substituted by 1 to 3 same or different members selected from the group consisting of alkyl, halogen and amino).

Examples of the preferable compounds among compounds of the above formula [1] include amide derivatives of the following (1) to (14), or pharmaceutically acceptable salts thereof:

(1) 4-(1-methylpiperidin-4-ylidenemethyl)-3-trifluoromethyl-N-{4-methyl-3-[4-(5-pyrimidinyl)pyrimidin-2-ylamino]phenyl}benzamide, (2) 4-(1-methylpiperidin-4-yloxy)-3-trifluoromethyl-N-{4-methyl-3-[4-(5-pyrimidinyl)pyrimidin-2-ylamino]phenyl}benzamide, (3) 4-(1-methylpiperazin-4-ylmethyl)-3-trifluoromethyl-N-{4-methyl-3-[6-(3-pyridyl)pyrimidin-4-ylamino]phenyl}benzamide, (4) 4-(1-methylpiperazin-4-ylmethyl)-3-trifluoromethyl-N-{4-methyl-3-[6-(5-pyrimidinyl)pyrimidin-4-ylamino]phenyl}benzamide, (5) (−)-4-((S)-3-amino-2-oxopyrrolidin-1-ylmethyl)-3-trifluoromethyl-N-{4-methyl-3-[4-(5-pyrimidinyl)pyrimidin-2-ylamino]phenyl}benzamide, (6) 4-[(S)-2-(1-pyrrolidinylmethyl)pyrrolidin-1-ylmethyl]-3-trifluoromethyl-N-{4-methyl-3-[4-(5-pyrimidinyl)pyrimidin-2-ylamino]phenyl}benzamide, (7) 4-[3-(dimethylaminomethyl)azetidin-1-ylmethyl]-3-trifluoromethyl-N-{4-methyl-3-[4-(5-pyrimidinyl)pyrimidin-2-ylamino]phenyl}benzamide, (8) 4-[(S)-3-(1-pyrrolidinyl)pyrrolidin-1-ylmethyl]-3-trifluoromethyl-N-{4-methyl-3-[4-(5-pyrimidinyl)pyrimidin-2-ylamino]phenyl}benzamide, (9) 4-{4-[(5-methyl-2-oxo-1,3-dioxol-4-yl)methyl]piperazin-1-ylmethyl}-3-trifluoromethyl-N-{4-methyl-3-[4-(5-pyrimidinyl)pyrimidin-2-ylamino]phenyl}benzamide,

(10) 4-(4-methylpiperazin-1-ylmethyl)-3-trifluoromethyl-N-{4-methyl-3-[4-(4-pyridyl)thiazol-2-ylamino]phenyl}benzamide,

(11) 4-[3-(dimethylamino)azetidin-1-ylmethyl]-3-trifluoromethyl-N-{4-methyl-3-[4-(5-pyrimidinyl)pyrimidin-2-ylamino]phenyl}benzamide,

(12) 4-[(R)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide,

(13) 4-[(S)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide, and

(14) 4-[(3R,4R)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide.

Furthermore, in the present invention, the amide derivatives of the following (1) to (37), or pharmaceutically acceptable salts thereof can be exemplified:

(1) 3-difluoromethyl-4-(4-methylpiperazin-1-ylmethyl)-N-{4-methyl-3-[4-(5-pyrimidinyl)pyrimidin-2-ylamino]phenyl}benzamide,
(2) 3-ethyl-4-(4-methylpiperazin-1-ylmethyl)-N-{4-methyl-3-[4-(5-pyrimidinyl)pyrimidin-2-ylamino]phenyl}benzamide,
(3) 4-(1-methylpiperidin-4-ylmethyl)-3-trifluoromethyl-N-{4-methyl-3-[4-(5-pyrimidinyl)pyrimidin-2-ylamino]phenyl}benzamide,
(4) 3,5-dichloro-4-[(S)-3-(dimethylamino)pyrrolidin-1-ylmethyl]-N-{4-methyl-3-[4-(5-pyrimidinyl)pyrimidin-2-ylamino]phenyl}benzamide,
(5) 3-methoxy-4-(4-methylpiperazin-1-ylmethyl)-N-{3-[4-(5-bromopyridin-3-yl)pyrimidin-2-ylamino]-4-methylphenyl}benzamide,
(6) 4-(4-ethylpiperazin-1-ylmethyl)-3-trifluoromethyl-N-{4-methyl-3-[4-(5-pyrimidinyl)pyrimidin-2-ylamino]phenyl}benzamide,
(7) 4-(4-ethylpiperazin-1-ylmethyl)-3-trifluoromethyl-N-{3-[4-(5-bromopyridin-3-yl)pyrimidin-2-ylamino]-4-methylphenyl}benzamide,
(8) 3-chloro-4-(4-methylpiperazin-1-ylmethyl)-N-{4-methyl-3-[4-(5-pyrimidinyl)pyrimidin-2-ylamino]phenyl}benzamide,
(9) 3-fluoromethyl-4-(1-methylpiperidin-4-ylmethyl)-N-{4-methyl-3-[4-(5-pyrimidinyl)pyrimidin-2-ylamino]phenyl}benzamide,
(10) 4-(4-methylpiperazin-1-ylmethyl)-3-trifluoromethyl-N-{4-methyl-3-[4-(5-pyrimidinyl)pyridin-2-ylamino]phenyl}benzamide,
(11) 4-(4-ethylpiperazin-1-ylmethyl)-3-trifluoromethyl-N-{4-methyl-3-[4-(5-pyrimidinyl)pyridin-2-ylamino]phenyl}benzamide,
(12) 4-(4-ethylpiperazin-1-ylmethyl)-3-trifluoromethyl-N-{4-methyl-3-[4-(3-pyridyl)pyridin-2-ylamino]phenyl}benzamide,
(13) 4-(4-methylpiperazin-1-ylmethyl)-3-trifluoromethyl-N-{4-methyl-3-[4-(3-pyridyl)pyridin-2-ylamino]phenyl}benzamide,
(14) 4-[4-(2-fluoroethyl)piperazin-1-ylmethyl]-3-trifluoromethyl-N-{4-methyl-3-[4-(5-pyrimidinyl)pyrimidin-2-ylamino]phenyl}benzamide,
(15) 4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide,
(16) 4-[(R)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide,
(17) 4-(1-piperazinylmethyl)-3-trifluoromethyl-N-{3-[4-(5-bromopyridin-3-yl)pyrimidin-2-ylamino]-4-methylphenyl}benzamide,
(18) 4-(1-piperazinylmethyl)-3-trifluoromethyl-N-{4-methyl-3-[4-(3-pyridyl)pyridin-2-ylamino]phenyl}benzamide,
(19) 4-(1-piperazinylmethyl)-3-trifluoromethyl-N-{4-methyl-3-[4-(5-pyrimidinyl)pyrimidin-2-ylamino]phenyl}benzamide,
(20) 4-(3-carbamoylpiperazin-1-ylmethyl)-3-trifluoromethyl-N-{4-methyl-3-[4-(5-pyrimidinyl)pyrimidin-2-ylamino]phenyl}benzamide,
(21) 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide,
(22) 4-(3-carbamoyl-4-methylpiperazin-1-ylmethyl)-3-trifluoromethyl-N-{4-methyl-3-[4-(5-pyrimidinyl)pyrimidin-2-ylamino]phenyl}benzamide,
(23) 4-((S)-3-methylpiperazin-1-ylmethyl)-3-trifluoromethyl-N-{4-methyl-3-[4-(5-pyrimidinyl)pyrimidin-2-ylamino]phenyl}benzamide,
(24) 4-((R)-3-methylpiperazin-1-ylmethyl)-3-trifluoromethyl-N-{4-methyl-3-[4-(5-pyrimidinyl)pyrimidin-2-ylamino]phenyl}benzamide,
(25) 4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide,
(26) 4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide,
(27) 4-((S)-3-aminopiperidinomethyl)-3-trifluoromethyl-N-{4-methyl-3-[4-(5-pyrimidinyl)pyrimidin-2-ylamino]phenyl}benzamide,
(28) 4-[(S)-3-(dimethylamino)piperidinomethyl]-3-trifluoromethyl-N-{4-methyl-3-[4-(5-pyrimidinyl)pyrimidin-2-ylamino]phenyl}benzamide,
(29) 4-((3S,4R)-3-amino-4-methylpyrrolidin-1-ylmethyl)-3-trifluoromethyl-N-{4-methyl-3-[4-(5-pyrimidinyl)pyrimidin-2-ylamino]phenyl}benzamide,
(30) 4-[(3S,4R)-3-(dimethylamino)-4-methylpyrrolidin-1-ylmethyl]-3-trifluoromethyl-N-{4-methyl-3-[4-(5-pyrimidinyl)pyrimidin-2-ylamino]phenyl}benzamide,
(31) 4-[(S)-3-(methylamino)pyrrolidin-1-ylmethyl]-3-trifluoromethyl-N-{4-methyl-3-[4-(5-pyrimidinyl)pyrimidin-2-ylamino]phenyl}benzamide,
(32) 4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide,
(33) 4-((R)-3,4-dimethylpiperazin-1-ylmethyl)-3-trifluoromethyl-N-{4-methyl-3-[4-(5-pyrimidinyl)pyrimidin-2-ylamino]phenyl}benzamide,
(34) 4-[(3R,4R)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide,
(35) 4-(1-methylpiperidin-4-yloxy)-3-trifluoromethyl-N-{4-methyl-3-[4-(3-pyridyl)pyrimidin-2-ylamino]phenyl}benzamide,
(36) 4-(1-methylpiperidin-4-ylidenemethyl)-3-trifluoromethyl-N-{4-methyl-3-[4-(3-pyridyl)pyrimidin-2-ylamino]phenyl}benzamide, and
(37) 4-[(R)-3-(dimethylaminomethyl)pyrrolidin-1-ylmethyl]-3-trifluoromethyl-N-{4-methyl-3-[4-(3-pyridyl)pyrimidin-2-ylamino]phenyl}benzamide.

Further, the present invention is directed to a pharmaceutical composition comprising the compound of the present invention as an active ingredient, for example, a BCR-ABL tyrosine kinase inhibitor. More specifically, the present invention is directed to a pharmaceutical composition as a therapeutic agent for chronic myelogenous leukemia, a therapeutic agent for acute lymphoblastic leukemia, or a therapeutic agent for acute myelogenous leukemia.

The compound of the present invention has BCR-ABL tyrosine kinase inhibitory activity and is useful as a drug for prevention or treatment of diseases such as chronic myelogenous leukemia, acute lymphoblastic leukemia and acute myelogenous leukemia (see, for example, Non-Patent Document 9).

The present invention will now be described in detail.

The "saturated, nitrogen-containing heterocyclic group" includes a 4- to 8-membered saturated ring group which is a saturated ring group having at least one nitrogen atom as an atom composing the ring and also may have 1 to 3 same or different members selected from the group consisting of a nitrogen atom, an oxygen atom and a sulfur atom. When the atom composing the ring is a nitrogen atom or a sulfur atom, the nitrogen atom or the sulfur atom may form an oxide. Examples thereof include pyrrolidinyl, piperidinyl, piperazinyl, azetidinyl, morpholinyl, thiomorpholinyl and hexahydro-1H-1,4-diazepinyl. However, the "saturated, nitrogen-containing heterocyclic group" of $R^{13}$ is limited to ones in which the atom composing the ring which links to $R^{13}$ via a double bond and the atom composing the ring adjacent thereto are carbon atoms, and for example, —CH=$R^{13}$ includes piperidin-4-ylidenemethyl.

"Alkyl" includes straight or branched alkyl groups having 1 to 10 carbons, for example, methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, n-nonyl and n-decyl. Straight alkyl groups having 1 to 3 carbon atoms are particularly preferred.

The alkyl moiety of "dialkylaminoalkyl", "alkoxy", "alkoxycarbonyl", "haloalkyl", "hydroxyalkyl", "monoalkylamino", "dialkylamino", "monoalkylcarbamoyl", "dialkylcarbamoyl", "alkoxyalkyl" and "hydroxyalkyl" includes the above-mentioned alkyl.

"Halogen" includes, for example, fluorine, chlorine, bromine and iodine.

"Haloalkyl" includes monohaloalkyl, dihaloalkyl and trihaloalkyl, and the halogen moiety of "haloalkyl" includes the above-mentioned halogen. "Haloalkyl" includes, for example, fluoromethyl, 2-fluoroethyl, difluoromethyl, trifluoromethyl and 2,2,2-trifluoroethyl.

"Acyl" includes acyl groups having 1 to 11 carbons, for example, formyl, acetyl, propionyl, butyryl, isobutyryl, benzoyl, 1-naphthoyl and 2-naphthoyl.

"Pyridyl" includes, for example, 2-pyridyl, 3-pyridyl and 4-pyridyl.

"Pyrimidinyl" includes, for example, 2-pyrimidinyl, 4-pyrimidinyl and 5-pyrimidinyl.

"Pyrazinyl" includes, for example, 2-pyrazinyl.

"Pyridazinyl" includes, for example, 3-pyridazinyl and 4-pyridazinyl.

"1,2-dihydropyridazinyl" includes, for example, 1,2-dihydropyridazin-3-yl and 1,2-dihydropyridazin-4-yl.

The "saturated, cyclic amino group" includes a 4- to 8-membered saturated ring group which is a saturated, cyclic amino group having at least one nitrogen atom as an atom composing the ring and also may have 1 to 3 same or different members selected from the group consisting of a nitrogen atom, an oxygen atom and a sulfur atom. When the atom composing the ring is a nitrogen atom or a sulfur atom, the nitrogen atom or the sulfur atom may form an oxide. Examples thereof include 1-pyrrolidinyl, 1-piperidinyl, 1-piperazinyl, 1-azetidinyl, 4-morpholinyl, 4-thiomorpholinyl, hexahydro-1H-1,4-diazepin-1-yl.

BEST MODE FOR CARRYING OUT THE INVENTION

The compound of the present invention can be produced from per se known compound or an intermediate which can be produced with ease, for example, by the following method. In the production of the compound of the present invention, it is common that the raw materials are used for reaction after being protected with proper protecting groups by the per se known methods, when the raw materials have substituents that affect the reaction. After the reaction, the protecting groups can be removed by per se known methods.

Process 1

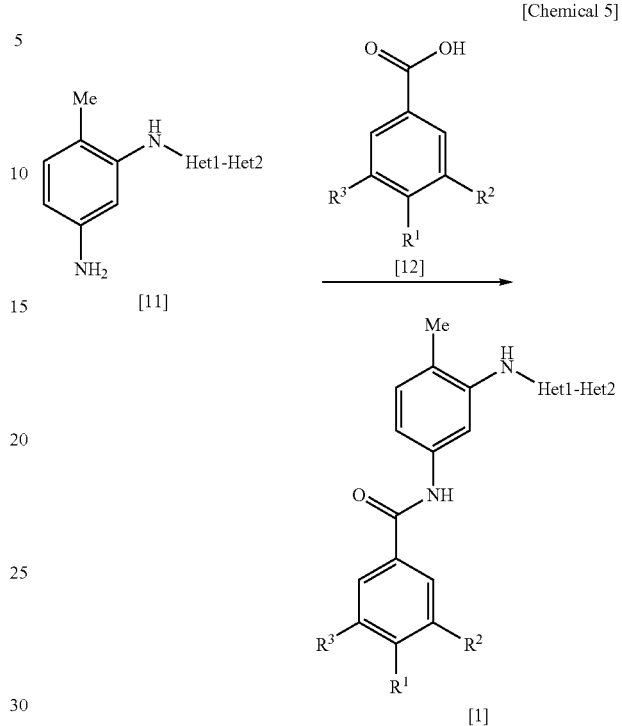

[wherein $R^1$, $R^2$, $R^3$, Het1 and Het2 are as defined above.]

This reaction is a condensation reaction of a compound [11] and a compound [12] and is therefore conducted by per se known methods used in the condensation reactions. A compound [1] can be produced by reacting a carboxylic acid as a compound [12], or a reactive derivative thereof with an amine as a compound [11]. Examples of the reactive derivatives of the compound [12] include those which are usually used in the amide condensation formation reaction, for example, acid halide (e.g., acid chloride, acid bromide, etc.), mixed acid anhydride, imidazolide and active amide. When using the carboxylic acid [12], a condensing agent (e.g., 1,1'-oxalyldiimidazole, 1-ethyl-3-(3-dimethylaminopropyl)carbodiimide, dicyclohexylcarbodiimide, diethyl cyanophosphonate, diphenylphosphoryl azide, 2-chloro-1-methylpyridinium iodide, 1H-benzotriazol-1-yloxytripyrrolidinophosphonium hexafluorophosphate, and benzotriazol-1-yloxytris(dimethylamino)phosphonium hexafluorophosphate) is used and the reaction is conducted at −20° C. to 100° C. in the presence or absence of a base (e.g., organic base such as triethylamine, N,N-diisopropyl-N-ethylamine, N,N-dimethylaniline, pyridine, 4-(dimethylamino)pyridine, 1,8-diazabicyclo[5.4.0]undec-7-ene, etc.). The solvent is not specifically limited as far as it is not involved in the reaction and examples thereof include ethers such as tetrahydrofuran and diethyl ether; amides such as N,N-dimethylformamide and N,N-dimethylacetamide; nitrites such as acetonitrile and propionitrile; hydrocarbons such as benzene and toluene; halogenated hydrocarbons such as chloroform and dichloromethane; and solvent mixtures thereof. In that case, additives (e.g., 1-hydroxybenzotriazole, N-hydroxysuccinimide, etc.) can also be added. The reaction time varies depending on the kinds of the raw material and the condensing agent and the reaction temperature, but usually it is preferably from 30 minutes to 24 hours. The amount of the compound [12] and the condensing agent is preferably 1 to 3 mol per mol of the compound [1,1]. When using an acid halide as the reactive derivative of the compound [12], the reaction is conducted at −20° C. to 100° C. using a pyridine solvent such as pyridine or 4-methylpyridine or the same base and solvent as those described above. Also 4-(dimethylamino)pyridine can be added as an additive. The reaction time varies depending on the kind of the acid halide and the reaction temperature, but usually it is preferably from 30 minutes to 24 hours.

Preparation Process of Raw Compound [11] for Use in Process 1

The compound [11] as the raw compound wherein Het1 is a group of the formula [6] can be prepared, for example, by the same manner as described in Patent Document 1.

The compound [11] as the raw compound wherein Het1 is a group of the formula [4], [5], [7] or [9] can be prepared by the following manner:

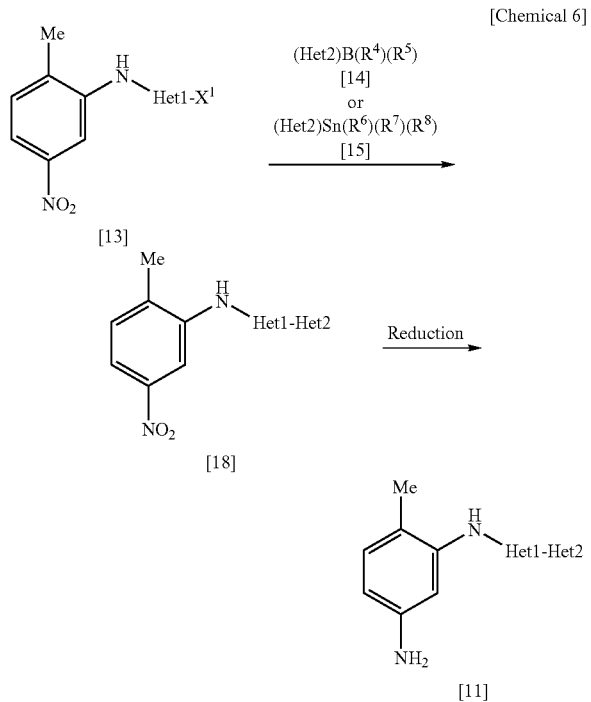

[Chemical 6]

[wherein Het1 and Het2 are as defined above; $R^4$ and $R^5$ may be the same or different from each other, and represent alkyl or hydroxy; $R^6$, $R^7$ and $R^8$ represent alkyl; and $X^1$ represents halogen.]

Step 1

This reaction is a cross-coupling reaction using a compound [13] and an organoboron compound [14] or an organotin compound [15] and can be conducted by per se known methods. For example, this reaction is conducted at 20° C. to 200° C. in a suitable solvent in the presence of a palladium catalyst. As the palladium catalyst, tetrakis(triphenylphosphine)palladium, dichlorobis(triphenylphosphine) palladium and dichlorobis(tri-o-tolylphosphine)palladium are usually used. The reaction solvent is not specifically limited as far as it is not involved in the reaction and examples thereof include ethers such as tetrahydrofuran, 1,4-dioxane and 1,2-dimethoxyethane; alcohols such as methanol and ethanol; amides such as N,N-dimethylformamide and N,N-dimethylacetamide; hydrocarbons such as benzene, toluene and xylene; organic amines such as pyridine and triethylamine; and solvent mixtures thereof. When using the compound [14], the addition of a base (e.g., sodium hydroxide, potassium carbonate, tripotassium phosphate, etc.) is essential. The reaction time varies depending on the kind of the raw material and the reaction temperature, but usually it is preferably from 1 hour to 48 hours.

Step 2

This reaction is a reaction of reducing an aromatic nitro group of a compound [16] into an amino group and is therefore conducted by per se known methods used in the reducing reaction. The method includes, for example, a method of treating with zinc or tin under the acidic conditions. According to the catalytic reduction method, for example, hydrogenation can be conducted using platinum, Raney nickel, platinum-carbon (Pt—C), palladium-carbon (Pd—C) or ruthenium complex as the catalyst. In addition, a method of using a sulfide such as sodium dithionite and a method of reducing with ammonium formate or hydrazine in the presence of a metal catalyst are exemplified.

The compound [13] as the raw compound wherein Het1 is a group of the formula [4] can be prepared, for example, by reacting 2,4-dichloropyridine (prepared, for example, by version of the method described in Non-Patent Document 12) with 2-methyl-5-nitroaniline according to the method of J. P. Wolfe et al. using a palladium catalyst (see Non-Patent Documents 10 and 11). When Het1 is a group of the formula [5], the compound can be prepared, for example, by reacting 1-bromo-3-iodobenzene with 2-methyl-5-nitroaniline. When Het1 is a group of the formula [7], the compound can be prepared, for example, by reacting 2,6-dichloropyrazine with 2-methyl-5-nitroaniline. When Het1 is a group of the formula [9], the compound can be prepared, for example, by reacting 4,6-dichloropirimidine with 2-methyl-5-nitroaniline. The reaction solvent is not specifically limited as far as it is not involved in the reaction and examples thereof include ethers such as tetrahydrofuran, 1,4-dioxane and 1,2-dimethoxyethane; hydrocarbons such as benzene, toluene and xylene; and solvent mixtures thereof. The reaction is conducted at 70° C. to 100° C. in the presence of a base. Examples of the palladium catalyst include tris(dibenzylideneacetone) dipalladium (0), palladium (II) acetate and tri(o-tolylphosphine) palladium (0). Usually, the amount of palladium is preferably from 0.5 mol % to 4 mol % based on the halogenated aryl. As a ligand of the palladium catalyst, for example, 1,3-bis(diphenylphosphino)propane, 1,1'-bis(diphenylphosphino)ferrocene and (±)-2,2'-bis(diphenylphosphino)-1,1'-binaphthyl [(±)-BINAP] can be used. Examples of the base include sodium t-butoxide, potassium t-butoxide, cesium carbonate, potassium carbonate and sodium carbonate. The reaction time varies depending on the kind of the raw material and the reaction temperature, but usually it is preferably from 1 hour to 36 hours.

The compound [13] can also be prepared by reacting 2,4-dichloropyridine, for example, when Het1 is a group of the formula [4], or by reacting 4,6-dichloropyrimidine, for example, when Het1 is a group of the formula [9], with 2-methyl-5-nitroaniline at 20° C. to 200° C. in a suitable solvent or in the absence of a solvent in the presence or absence of a base. Examples of the base include pyridine, triethylamine, N,N-diisopropyl-N-ethylamine, potassium carbonate, sodium hydrogen carbonate and potassium hydroxide. The solvent to be used is not specifically limited as far as it is not involved in the reaction and examples thereof include ethers such as tetrahydrofuran, dibutyl ether and 1,4-dioxane; amides such as N,N-dimethylformamide and N,N-dimethylacetamide; hydrocarbons such as benzene and toluene; alcohols such as ethylene glycol and 2-methoxyethanol; halogenated hydrocarbons such as chloroform and dichloromethane; dimethyl sulfoxide; and solvent mixtures thereof. The reaction time varies depending on the kind of the raw material and the reaction temperature, but usually it is preferably from 1 hour to 24 hours.

The compound [16a] as the raw compound (compound [16] wherein Het1 is a group of the formula [4]) can also be prepared, for example, by the following manner:

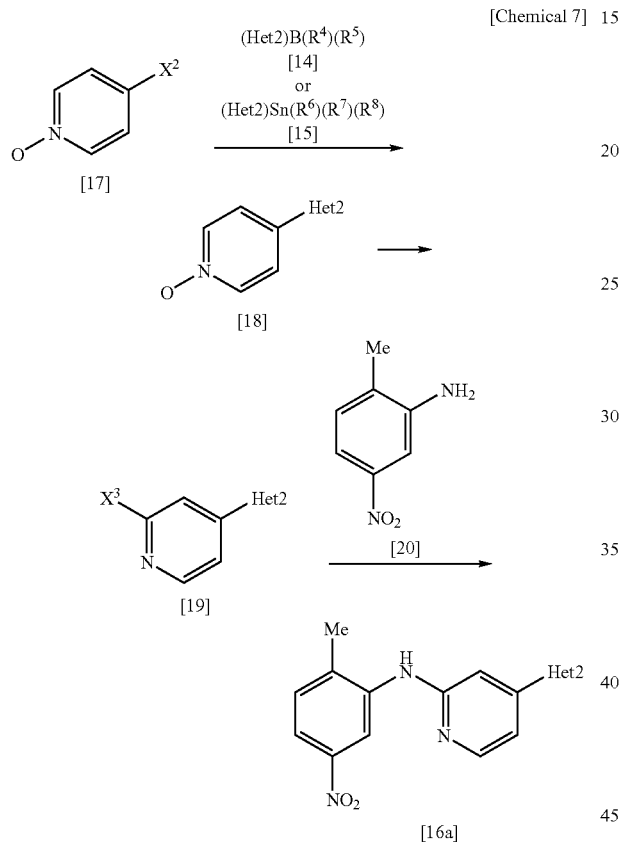

[Chemical 7]

[wherein $R^4$, $R^5$, $R^6$, $R^7$, $R^8$ and Het2 are as defined above, and $X^2$ and $X^3$ represent halogen.]

Step 1

This reaction is a cross-coupling reaction using a compound [17] and an organoboron compound [14] or an organotin compound [15] and can be conducted by the same manner as described above.

Step 2

A compound [19] is prepared by halogenating a compound [18]. The reaction is therefore conducted by per se known methods. The reaction is usually conducted using phosphorus oxychloride, phosphorus oxybromide, phosphorus pentachloride or phosphorus pentabromide with or without solvent. The reaction solvent is not specifically limited as far as it is not involved in the reaction and examples thereof include ethers such as tetrahydrofuran, dibutyl ether and 1,4-dioxane; amides such as N,N-dimethylformamide and N,N-dimethylacetamide; halogenated hydrocarbons such as chloroform and dichloromethane; and solvent mixtures thereof. The reaction is usually conducted at room temperature to 130° C. and usually the reaction time is preferably from 20 minutes to 24 hours.

Step 3

A compound [16a] can be prepared by reacting the compound [19] with a compound [20] according to the above method using a palladium catalyst (see, for example, Non-Patent Documents 10 and 11).

A compound [11a] (compound [11] wherein Het1 is a group of the formula [4]) can be prepared by reacting the compound [19] with a compound [21] according to the above method using a palladium catalyst (see, for example, Non-Patent Documents 10 and 11) to give a compound [22] and deprotecting the compound [22].

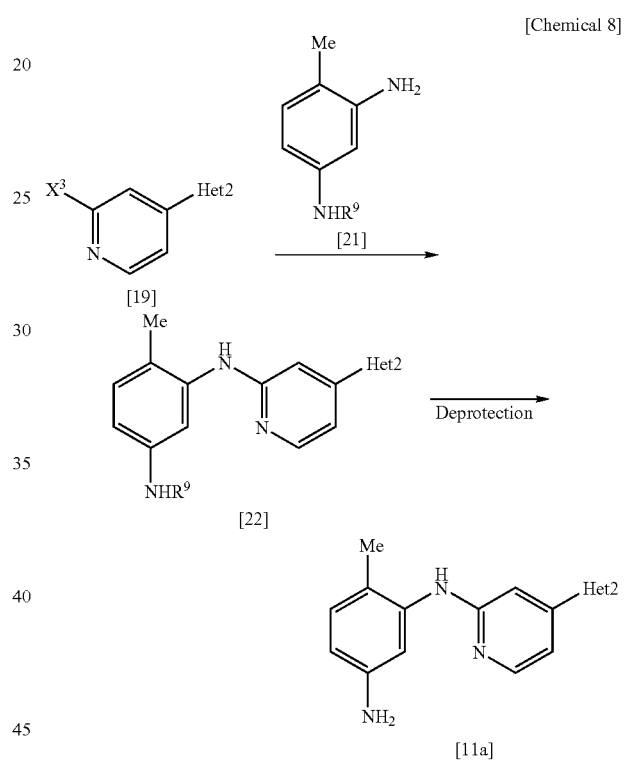

[Chemical 8]

[wherein Het2 and $X^3$ are as defined above, and $R^9$ represents a protecting group]

Step 1

The raw compound [21] can be prepared by protecting 2,4-diaminotoluene with a suitable protecting group by per se known methods. Examples of the protecting group include acyl derivatives such as benzoyl, acetyl and formyl; and urethane type derivatives such as benzyloxycarbonyl, t-butoxycarbonyl and 2,2,2-trichloroethoxycarbonyl. A compound [22] can be prepared by reacting the compound [19] with the compound [21] using the above palladium catalyst.

Step 2

In the deprotection reaction of the compound [22], an acyl type protecting group is removed by hydrolysis using acid or alkali, or removed with ammonia water or hydrazine. Examples of the acid used in the hydrolysis include inorganic acids such as hydrochloric acid and sulfuric acid, and examples of the base include inorganic bases such as sodium hydroxide and potassium hydroxide. The reaction solvent is not specifically limited as far as it is not involved in the reaction and examples thereof include alcohols such as methanol and ethanol; ethers such as tetrahydrofuran and 1,4-dioxane; water; and solvent mixtures thereof. The reaction temperature is from 0° C. to 100° C. and the reaction time is usually from several minutes to 24 hours. When the protecting group is a urethane type derivative, the protecting group can be removed by hydrogenation using a palladium catalyst, or removed with hydrochloric acid, trifluoroacetic acid, trimethylsilyl iodide or boron trifluoride, although depending on the kind of the protecting group.

The compound [11b] as the raw compound [11], wherein Het1 is a group of the formula [10], can be prepared by conducting the same method as in, for example, Non-Patent Document 13 to prepare the compound [16b] and then reducing the aromatic nitro group into the amino group as described hereinafter.

[Chemical 9]

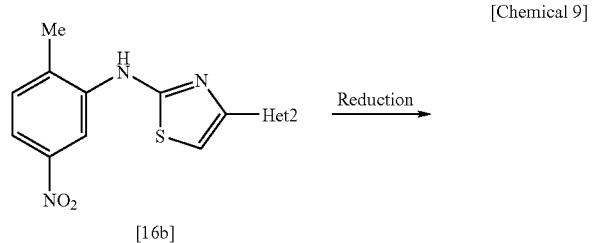

[wherein Het2 is as defined above.]

Preparation Process of Raw Compound [12] for Use in Process 1

The compound [12a] as the raw compound [12] can be prepared, for example, by the following manner:

[Chemical 10]

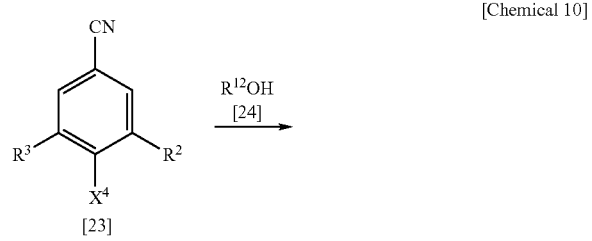

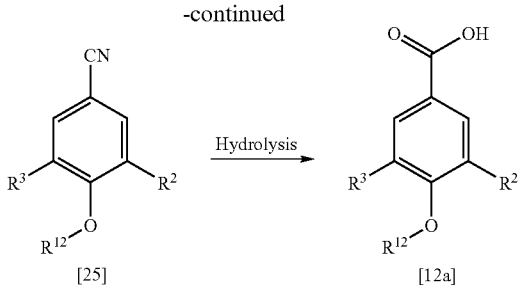

[wherein $R^2$, $R^3$ and $R^{12}$ are as defined above, and $X^4$ represents halogen.]

Step 1

A compound [25] can be prepared through an ether linkage formation between a halogenated aryl [23] and an alcohol [24]. This reaction is a nucleophilic substitution reaction of the compound [23] and alcohols and is conducted by per se known methods. This reaction is conducted in a suitable solvent in the presence of a base. Examples of the preferably used base include any basic material which is usually used (e.g., pyridine, triethylamine), alkoxides of alkali metals (e.g., potassium t-butoxide), metal hydride (e.g., sodium hydride), and inorganic bases (e.g., potassium carbonate, sodium hydrogen carbonate, sodium hydroxide, potassium hydroxide). The solvent to be used is not specifically limited as far as it is not involved in the reaction and examples thereof include ethers such as tetrahydrofuran and 1,4-dioxane; amides such as N,N-dimethylformamide and N,N-dimethylacetamide; nitriles such as acetonitrile and propionitrile; hydrocarbons such as benzene and toluene; dimethylsulfoxide; water; and solvent mixtures thereof. The reaction temperature is usually from −78° C. to 200° C. The reaction time varies depending on the kind of the raw material and the reaction temperature, but usually it is preferably from 30 minutes to 24 hours. In addition, in such the substitution reaction, copper powder, copper (I) halide or copper alkoxide is used as a catalyst. As an alternative method, a method of using a palladium catalyst of A. Aranyos, et al. or G. Mann, et al. (see, for example, Non-Patent Documents 14 and 15) can be used to prepare the compound [25] from the halogenated aryl [23] and the alcohol [24].

Step 2

A compound [12a] can be prepared by hydrolyzing the compound [25]. The reaction is usually conducted in a suitable solvent in the presence of an acid or a base. Examples of the acid used in the hydrolysis include inorganic acids such as hydrochloric acid and sulfuric acid, and organic acids such as acetic acid and formic acid, and examples of the base include inorganic bases such as sodium hydroxide and potassium hydroxide. Examples of the reaction solvent include alcohols such as methanol, ethanol and ethylene glycol; ethers such as tetrahydrofuran and 1,4-dioxane; water; and solvent mixtures thereof. The reaction temperature is from 0° C. to 200° C. and usually the reaction time is preferably from 30 minutes to 24 hours.

The compound [12b] as the raw compound [12] can be prepared, for example, by the following manner:

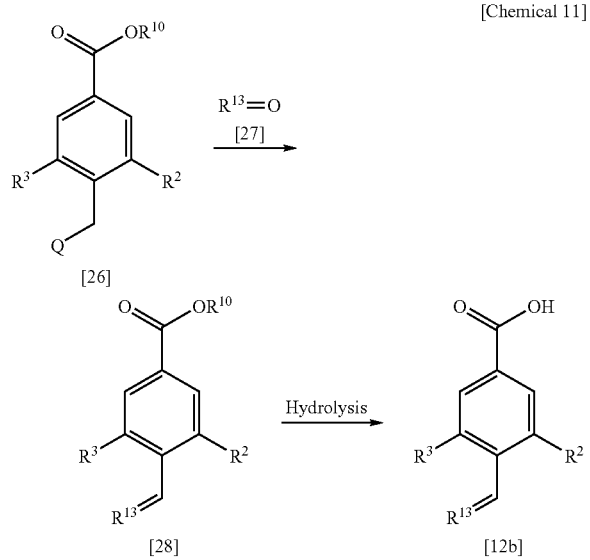

[wherein $R^2$, $R^3$ and $R^{13}$ are as defined above; $R^{10}$ represents alkyl; and Q represents dialkoxyphosphoryl halide salt or dialkoxy phosphoryl.]

Step 1

This reaction is a Wittig reaction or Horner-Emmons reaction of an organophosphorus compound [26] and a compound [27], and is therefore conducted by per se known methods such as the Wittig reaction or Horner-Emmons reaction. The reaction is conducted in a suitable solvent in the presence of a base at −78° C. to 150° C. Examples of the base to be used include n-butyllithium, sodium hydride, sodium ethoxide, potassium t-butoxide and lithium diisopropylamide. The solvent to be used is not specifically limited as far as it is not involved in the reaction and examples thereof include ethers such as tetrahydrofuran and 1,2-dimethoxyethane, amides such as N,N-dimethylformamide and N,N-dimethylacetamide; alcohols such as methanol and ethanol; hydrocarbons such as n-hexane, benzene and toluene; halogenated hydrocarbons such as chloroform and dichloromethane; dimethylsulfoxide; and solvent mixtures thereof. The reaction time varies depending on the kinds of the raw material and the condensing agent and the reaction temperature, but usually it is preferably from 30 minutes to 24 hours.

The compound [26] as the raw material is an alkyl(triaryl)phosphonium halide salt or alkyl(dialkoxy)phosphoryl, each of which can be prepared by version of the method described in Non-Patent Documents 16 and 17.

Step 2

A compound [12b] can be prepared by hydrolyzing the compound [28]. The reaction is usually conducted in a suitable solvent in the presence of an acid or a base. Examples of the acid used in the hydrolysis include inorganic acids such as hydrochloric acid and sulfuric acid, and examples of the base include inorganic bases such as sodium hydroxide and potassium hydroxide. Examples of the reaction solvent include alcohols such as methanol and ethanol; ethers such as tetrahydrofuran and 1,4-dioxane; water; and solvent mixtures thereof. The reaction temperature is from 0° C. to 100° C. and usually the reaction time is preferably from 30 minutes to 24 hours.

The compound [12c] as the raw compound [12] can be prepared, for example, by the following manner:

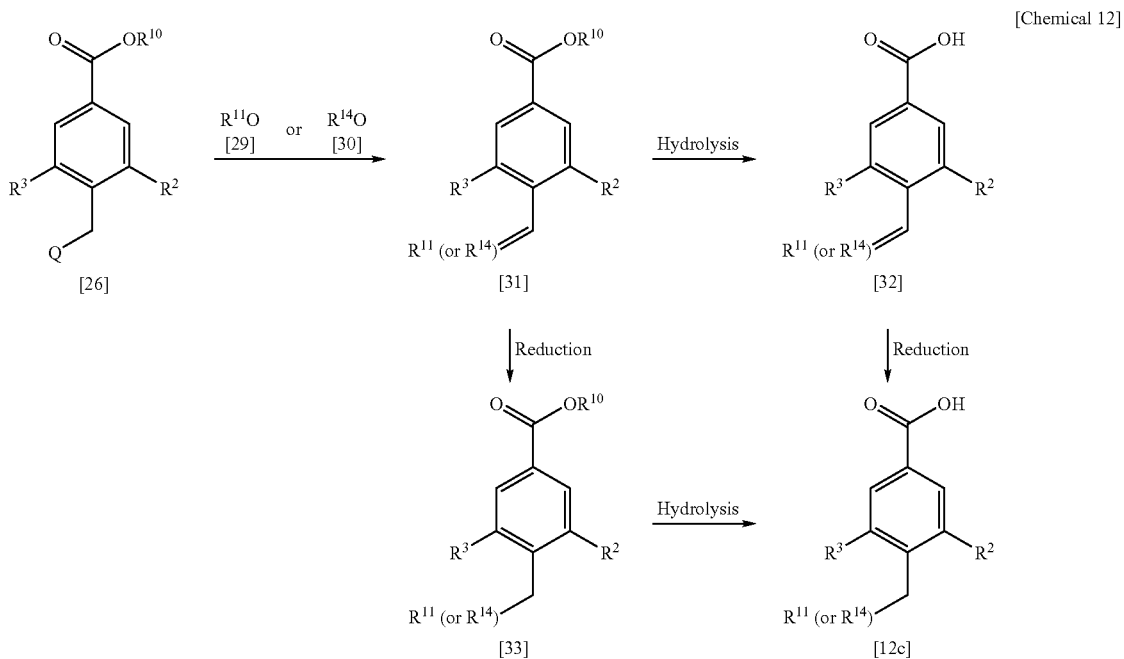

[wherein $R^2$, $R^3$, $R^{10}$, $R^{11}$, $R^{14}$ and Q are as defined above.]

Step 1

This reaction is a Wittig reaction or Horner-Emmons reaction of an organophosphorus compound [26] and a compound

[29] or a compound [30], and can be conducted by version of a general method for synthesizing [28] from the above described [26].

Step 2

A compound [12c] can be prepared by hydrolyzing the compound [31] to prepare a compound [32], and then reducing the compound [32]. Alternatively, the compound [12c] can be prepared by reducing the compound [31] to prepare a compound [33], and then hydrolyzing the compound [33]. The hydrolysis reaction can be conducted by version of a general method for synthesizing [12b] from the above described [28]. The reduction reaction can be conducted by per se known methods.

Further, in the case where $R^{11}$ or $R^{14}$ is a saturated, cyclic amino group, it can be prepared, for example, by the following method:

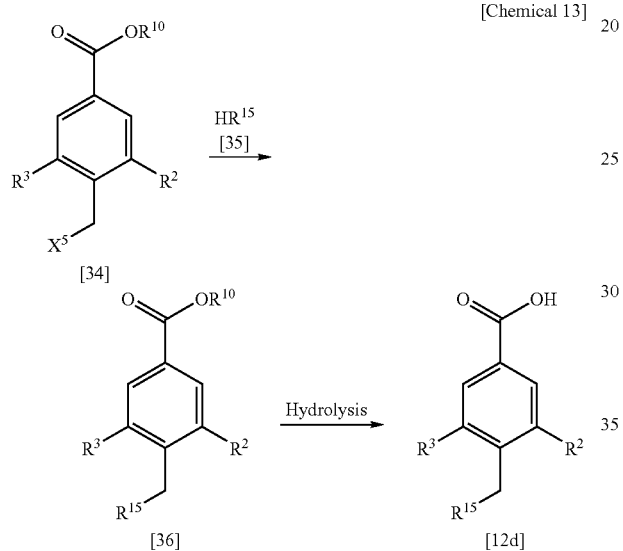

[wherein $R^2$, $R^3$ and $R^{10}$ are as defined above; $R^{15}$ represents a saturated, cyclic amino group; $X^5$ represents a leaving group such as Cl, Br, I, p-toluene sulfonyloxy and methane sulfonyloxy.]

Step 1

A compound [36] can be prepared by condensing a compound [34] (which can be prepared, for example, by version of the method described in Non-Patent Document 18) with a saturated, cyclic amine [35] (wherein the leaving group $X^5$ represents a leaving group such as halogen, p-toluene sulfonyloxy and methane sulfonyloxy). This reaction is a nucleophilic substitution reaction of the compound [34] and amines and is conducted by per se known methods. This reaction is conducted in a suitable solvent using an excess amine or in the presence of a base. Examples of preferable base include pyridine, triethylamine, N,N-diisopropyl-N-ethylamine, potassium carbonate and sodium hydrogen carbonate. The solvent to be used is not specifically limited as far as it is not involved in the reaction and examples thereof include ethers such as tetrahydrofuran and diethyl ether; amides such as N,N-dimethylformamide and N,N-dimethylacetamide; nitriles such as acetonitrile and propionitrile; hydrocarbons such as benzene and toluene; alcohols such as methanol and ethanol; water; and solvent mixtures thereof. The reaction temperature is usually from 0° C. to 100° C. The reaction time varies depending on the kind of the raw material and the reaction temperature, but usually it is preferably from 30 minutes to 24 hours.

Step 2

A compound [12d] can be prepared by hydrolyzing the compound [36].

This reaction is a hydrolysis reaction of esters, and can be conducted by version of a general method for synthesizing [12b] from the above described [28].

Process 2

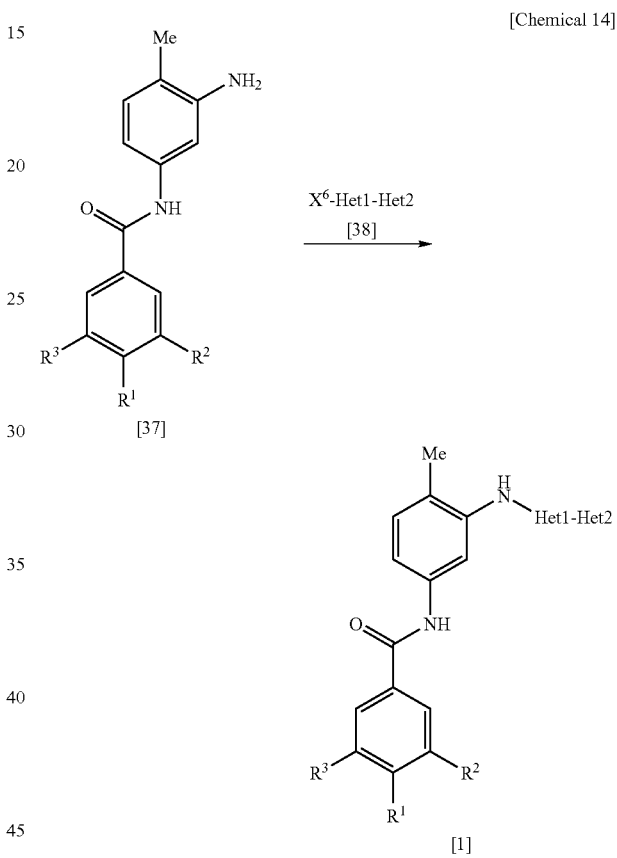

[wherein $R^1$, $R^2$, $R^3$, Het1 and Het2 are as defined above; $X^6$ represents Cl, Br, I or $SR^{16}$ (wherein $R^{16}$ represents alkyl).]

A compound [1] can be prepared by reacting a compound [37] with a compound [38]. The reaction is conducted at 20° C. to 200° C. in the absence of a solvent or a suitable solvent in the presence or absence of a base. Examples of the base include pyridine, triethylamine, N,N-diisopropyl-N-ethylamine, potassium carbonate, sodium hydrogen carbonate and potassium hydroxide. The solvent is not specifically limited as far as it is not involved in the reaction and examples thereof include ethers such as tetrahydrofuran, dibutyl ether and 1,4-dioxane; amides such as N,N-dimethylformamide and N,N-dimethylacetamide; hydrocarbons such as benzene and toluene; alcohols such as ethylene glycol and 2-methoxyethanol; halogenated hydrocarbons such as chloroform and dichloromethane; dimethyl sulfoxide; and solvent mixtures thereof. The reaction time varies depending on the kind of the raw material and the reaction temperature, but usually it is preferably from 1 hour to 24 hours.

Further, the compound [1] can be prepared by reacting the compound [37] with the compound [38] using a method using the palladium catalyst as described in the process 1 (see, for example, Non-Patent Documents 10 and 11).

The compound [37] as the raw compound can be prepared, for example, by condensing 2,4-diaminotoluene with carboxylic acid as the compound [1,2] or a reactive derivative thereof by version of the process 1.

The compound [38] as the raw compound can be prepared by using 2,6-dibromopyridine, for example, when Het1 is a group of the formula [2]; 3,5-dibromopyridine, for example, when Het1 is a group of the formula [3]; 2,4-dibromopyridine, for example, when Het1 is a group of the formula [4]; 1,3-dibromobenzene, for example, when Het1 is a group of the formula [5]; 2,4-dichloropyrimidine, for example, when Het1 is a group of the formula [6]; and 2,6-dichloropyrazine, for example, when Het1 is a group of the formula [7] in accordance with the process 4 described hereinafter. When Het1 is a group of the formula [4], the compound [38] can also be prepared by the method described in the above-mentioned process 1.

Process 3

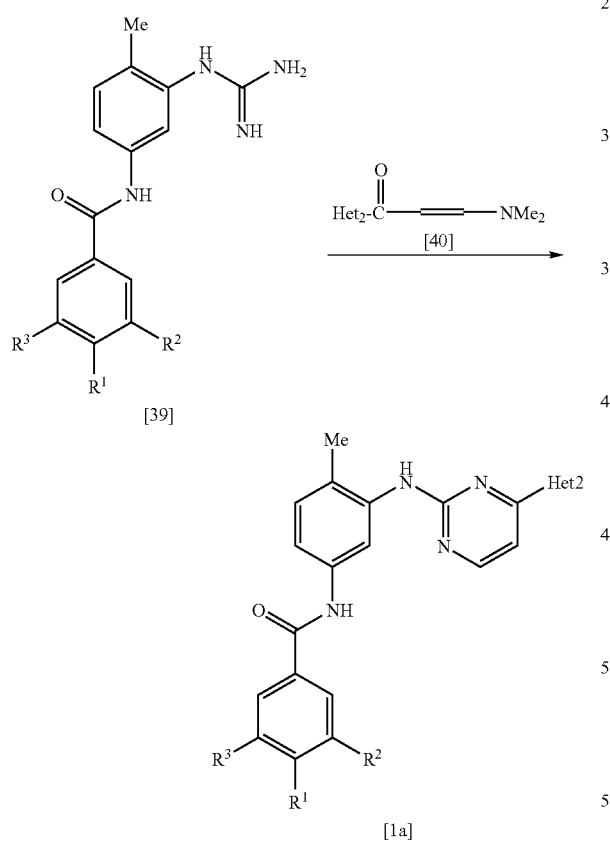

[wherein $R^1$, $R^2$, $R^3$ and Het2 are as defined above.]

A compound [1a](compound [1] wherein Het1 is a group of the formula [6]) can be prepared by reacting a compound [39] or its acid addition salt with a compound [40]. The reaction is conducted at 20° C. to 200° C. in a suitable solvent. The solvent to be used is not specifically limited as far as it is not involved in the reaction and examples thereof include alcohols such as methanol, ethanol, 2-propanol and 2-methoxyethanol. The amount of the compound [40] to be used is from 1- to 2-fold mol, and preferably from 1- to 1.2-fold mol, per mol of the compound [39]. The reaction time varies depending on the kind of the raw material and the reaction temperature, but usually it is preferably from 30 minutes to 30 hours. When using the acid addition salt of the compound [39], the reaction can be conducted by adding a suitable base (e.g., potassium carbonate, sodium hydrogen carbonate, sodium hydroxide, potassium hydroxide, etc.).

The compound [39] as the raw compound can be prepared in the form of a free salt or an acid addition salt by reacting the compound [37] with cyanamide by the method described in the document (see, for example, Non-Patent Document 19).

The compound [40] as the raw compound can be prepared, for example, by version of the method described in Patent Document 1.

Process 4

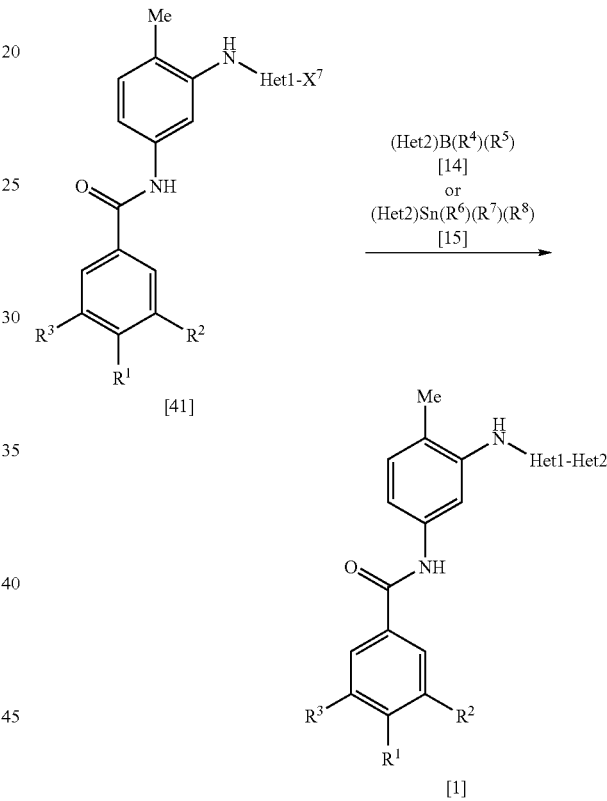

[wherein $R^1$, $R^2$, $R^3$, $R^4$, $R^5$, $R^6$, $R^7$, $R^8$, Het1 and Het2 are as defined above; and $X^7$ represents halogen.]

This reaction is a cross-coupling reaction using a compound [41] and an organoboron compound [14] or an organotin compound [15] and can be conducted by per se known methods. For example, this reaction is conducted at 20° C. to 200° C. in a suitable solvent in the presence of a palladium catalyst. As the palladium catalyst, tetrakis(triphenylphosphine)palladium, dichlorobis(triphenylphosphine)palladium and dichlorobis(tri-o-tolylphosphine)palladium are usually used. The reaction solvent is not specifically limited as far as it is not involved in the reaction and examples thereof include ethers such as tetrahydrofuran, 1,4-dioxane and 1,2-dimethoxyethane; alcohols such as methanol and ethanol; amides such as N,N-dimethylformamide and N,N-dimethylacetamide; hydrocarbons such as benzene, toluene and xylene; organic amines such as pyridine and triethylamine; and solvent mixtures thereof. When using the compound [14], the addition of a base (e.g., sodium hydroxide, potassium carbonate, tripotassium phosphate, etc.) is essential. The reaction time varies depending on the kind of the raw material and the reaction temperature, but usually it is preferably from 1 hour to 48 hours.

The compound [41] as the raw compound can be prepared, for example, by reacting a compound [37] with 4-hydroxy-2-(methylthio)pyridine when Het1 is a group of the formula [4], or reacting a compound [37] with 4-hydroxy-2-(methylthio)pyrimidine and treating the reaction product with phosphorus oxychloride (see, for example, Non-Patent Document 20) when Het1 is a group of the formula [6], or reacting by the method described in the document (see, for example, Non-Patent Document 21) using a compound [37] and 2,4-dichloropyrimidine when Het1 is a group of the formula [6].

Process 5

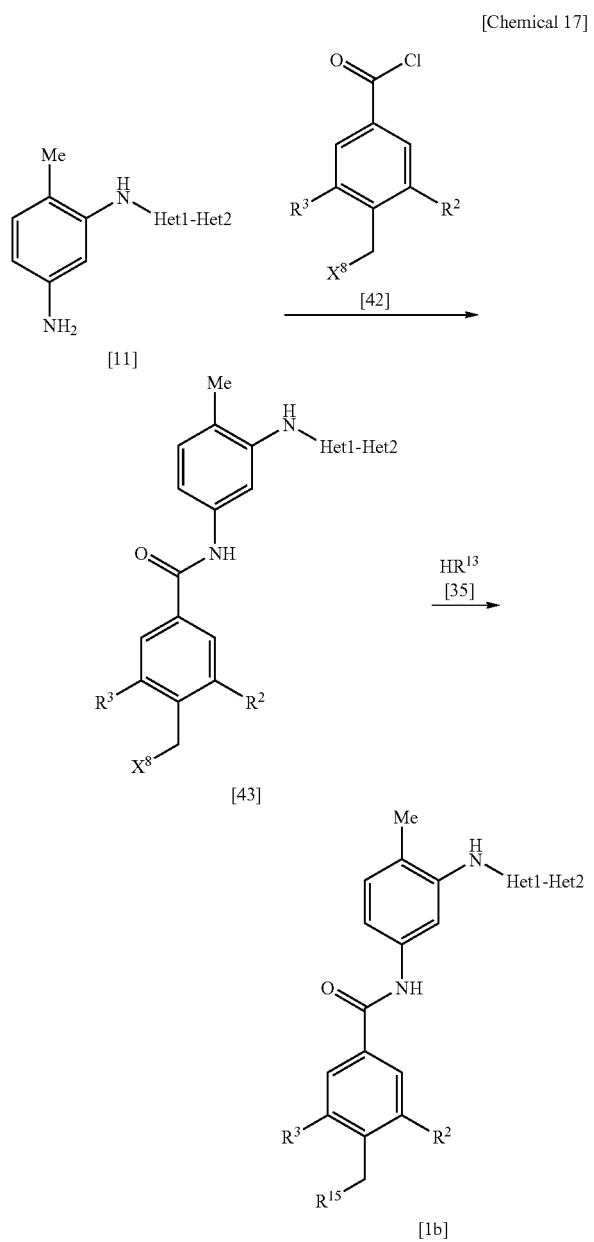

[Chemical 17]

[wherein $R^2$, $R^3$ and $R^{15}$, Het1 and Het2 are as defined above; and $X^8$ represents halogen.]

Step 1

This reaction is conducted by condensing a compound [11] and acid chloride [42] according to the method described in the process 1.

Step 2

A compound [1b] (the compound [1] wherein $R^1$ is —$CH_2$—$R^{15}$) can be prepared by condensing a compound [43] with an amine [35]. This reaction is a condensation reaction of acid chloride and amines and is conducted by per se known methods. This reaction is conducted in a suitable solvent using an excess amine or in the presence of a base. Examples of preferable base include pyridine, triethylamine, N,N-diisopropyl-N-ethylamine, potassium carbonate and sodium hydrogen carbonate. The solvent is not specifically limited as far as it is not involved in the reaction and examples thereof include ethers such as tetrahydrofuran, diethyl ether and 1,3-dioxane; amides such as N,N-dimethylformamide and N,N-dimethylacetamide; nitriles such as acetonitrile and propionitrile; hydrocarbons such as benzene and toluene; alcohols such as methanol and ethanol; water; and solvent mixtures thereof. The reaction temperature is usually from 0° C. to 100° C. The reaction time varies depending on the kind of the raw material and the reaction temperature, but usually it is preferably from 30 minutes to 24 hours.

Process 6

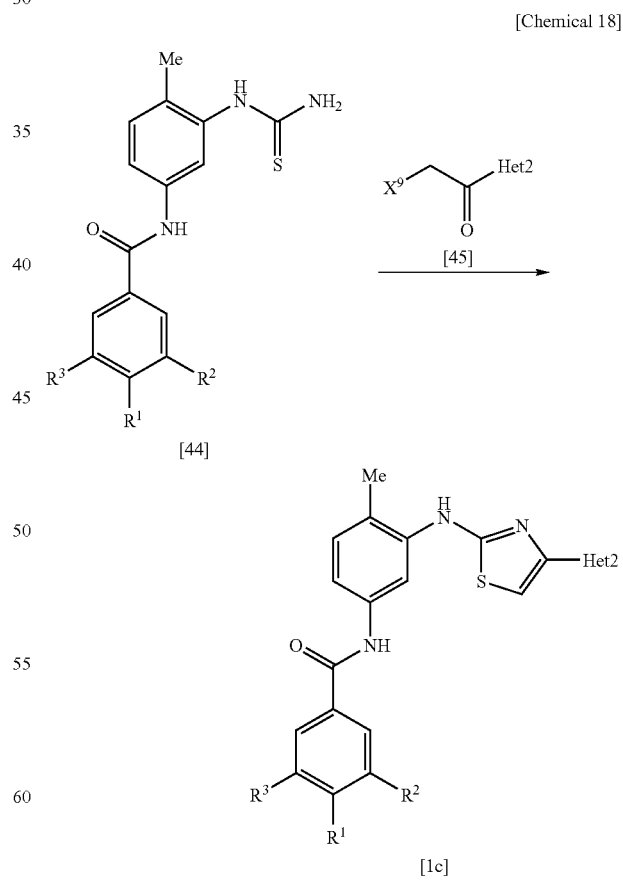

[Chemical 18]

[wherein $R^1$, $R^2$, $R^3$ and Het2 are as defined above; and $X^9$ represents halogen.]

A compound [1c] (compound [1] wherein Het1 is a group of the formula [10]) can be prepared by reacting a compound [44] and a compound [45] or its acid addition salt to form a ring. This reaction can be conducted by per se known methods as a method for synthesizing a 2-aminothiazole derivative (see, for example, Non-Patent Document 13).

The amide derivative according to the present invention can be used in the form of a free base as a medicine, however, it can be also used as a pharmaceutically acceptable salt made by the per se known methods. These salts include salts of mineral acids such as hydrochloric acid, hydrobromic acid, sulfuric acid and phosphoric acid, and salts of organic acids such as acetic acid, citric acid, tartaric acid, maleic acid, succinic acid, fumaric acid, p-toluene sulfonic acid, benzene sulfonic acid and methane sulfonic acid.

The hydrochloride of the amide derivative according to the present invention, for example, can be obtained by dissolving the amide derivative according to the present invention in an alcohol solution, an ethyl acetate solution or an ether solution of the hydrogen chloride.

As shown in test examples described hereinafter, the compound of the present invention has high inhibitory activity of BCR-ABL tyrosine kinase as compared with a pyrimidine derivative disclosed specifically in Patent Document 1. Therefore, the compound of the present invention is useful as a preventive or therapeutic agent for diseases involved in BCR-ABL tyrosine kinase, for example, chronic myelogenous leukemia, acute lymphoblastic leukemia and acute myelogenous leukemia.

When the compound of the present invention is administered as a medicine, it can be administered to mammals, including humans, either by itself or as a pharmaceutical composition in which the compound is contained in a pharmaceutically acceptable non-toxic and inert carrier in the proportion of, for example, 0.1% to 99.5%, or preferably 0.5% to 90%.

One or more auxiliary agents for formulation such as fillers or a solid, semisolid or liquid diluent are used. It is desirable to administer the pharmaceutical composition in unit dosage form. The pharmaceutical composition of the present invention can be administered intravenously, orally, directly to the target tissue, topically (e.g., transdermally) or rectally. It is a matter of course that a dosage form suitable for any of the administration modes described above is employed. It is desirable to administer orally.

It is desirable to set the dosage of the compound as a BCR-ABL tyrosine kinase inhibitor or a therapeutic agent for chronic myelogenous leukemia by considering the condition of the patient, such as age, body weight, and the characteristics and severity of the disease and other factors such as the administration route; but usually for adults, an amount in the range of 0.1 mg/person to 1000 mg/person per day, and preferably 1 mg/person to 500 mg/person per day, is generally a dose of the compound of the present invention.

In some cases, amounts below this range are sufficient, and conversely, in other cases larger amounts are required. It can be administered by dividing the total dosage into two or three doses per day.

EXAMPLES

The present invention will now described in more detail by way of Reference Examples, Examples, Test Examples and Formulation Examples of the compound of the present invention, to which, however, the present invention is not limited.

Reference Example 1

3-ethyl-4-(4-methylpiperazin-1-ylmethyl)benzoyl chloride hydrochloride

Step 1 ethyl 3-iodo-4-methylbenzoate 40.61 g of 3-iodo-4-methylbenzoic acid was suspended in 406 ml of ethanol and 9.1 ml of concentrated sulfuric acid was added, and then the mixture was heated at reflux for 24 hours. After the solvent was distilled off under reduced pressure, the residue was mixed with iced water, made basic with an aqueous saturated sodium hydrogen carbonate solution, followed by extraction with ethyl acetate twice. The extracts were washed in turn with water and saturated saline and then dried over anhydrous magnesium sulfate. The solvent was distilled off under reduced pressure to obtain 44.44 g of a crude product as a brown oily product.

Step 2 ethyl 4-(bromomethyl)-3-iodobenzoate 44.4 g of ethyl 3-iodo-4-methylbenzoate obtained in the step 1 was dissolved in 550 ml of carbon tetrachloride and 25.3 g of N-bromosuccinimide and 355 mg of benzoyl peroxide were added thereto, and then the reaction solution was heated at reflux under exposure to light from an incandescent lamp (1500 W) for 8 hours. Insolubles were removed by filtration, and then the solvent in the filtrate was distilled off under reduced pressure to obtain 56.99 g of a crude product as reddish violet crystals.

Step 3 ethyl 3-iodo-4-(4-methylpiperazin-1-ylmethyl)benzoate 57.0 g of ethyl 4-(bromomethyl)-3-iodobenzoate obtained in the step 2 was dissolved in 570 ml of anhydrous tetrahydrofuran and, after adding 22.8 g of potassium carbonate, 12.1 g of N-methylpiperazine in 70 ml of tetrahydrofuran solution was added dropwise over 20 minutes while stirring at room temperature. After stirring at room temperature for 4 hours, insolubles were removed by filtration and the solvent in the filtrate was distilled off under reduced pressure. The residue was purified by silica gel column chromatography to obtain 32.9 g of the objective compound as a yellow oily product.

Step 4 ethyl 4-(4-methylpiperazin-1-ylmethyl)-3-(trimethylsilanylethynyl)benzoate

To 3.77 g of ethyl 3-iodo-4-(4-methylpiperazin-1-ylmethyl)benzoate obtained in the step 3, 34 mg of bis(triphenylphosphine)palladium(II) dichloride, 19 mg of copper iodide, 1.65 ml of trimethylsilylacetylene and 38 ml of triethylamine were added in turn and the reaction solution was heated at reflux at 80° C. for 2 hours under an argon atmosphere. The reaction solution was air-cooled, insolubles were removed by filtration, the insolubles were washed with ethyl acetate, and then the solvent in the filtrate was distilled off under reduced pressure. Ethyl acetate was added to the residue and the mixture was washed in turn with 5% aqueous ammonia, water and saturated saline, and then the organic layer was distilled off under reduced pressure. The residue was purified by silica gel column chromatography to obtain 2.60 g of the objective compound as a yellow oily product.

Step 5

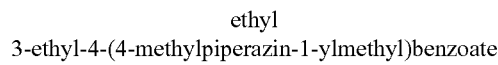
ethyl 3-ethyl-4-(4-methylpiperazin-1-ylmethyl)benzoate 2.60 g of ethyl 4-(4-methylpiperazin-1-ylmethyl)-3-(trimethylsilanylethynyl)benzoate obtained in the step 4 was dissolved in 13 ml of methanol and 3.0 g of potassium carbonate was added thereto, and then the mixture was stirred at room temperature for one minute. After the solvent was distilled off under reduced pressure, ethyl acetate and water were added to the reaction mixture and the aqueous layer was separated. The organic layer was washed twice with water and with saturated saline, and then dried over anhydrous magnesium sulfate and the solvent was distilled off under reduced pressure. The residue was dissolved in 26 ml of ethanol and 260 mg of 10% palladium-carbon was added, and then the mixture was hydrogenated at room temperature under 4 atm for 15 hours. The catalyst was removed by filtration and the solvent in the filtrate was distilled off under reduced pressure to obtain 1.83 g of a crude product as a yellow oily product.

Step 6

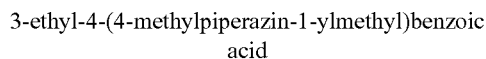
3-ethyl-4-(4-methylpiperazin-1-ylmethyl)benzoic acid 1.83 g of ethyl 3-ethyl-4-(4-methylpiperazin-1-ylmethyl)benzoate obtained in the step 5 was dissolved in 20 ml of ethanol and 10 ml of a 1N aqueous sodium hydroxide solution was added thereto, and then the mixture was heated at reflux for 2 hours. The reaction solution was neutralized by adding 10 ml of 1N hydrochloric acid under ice cooling. After water was distilled off under reduced pressure, water was azeotropically removed by adding toluene to the residue to obtain 2.16 g of a crude product as a yellow crystal.

Step 7

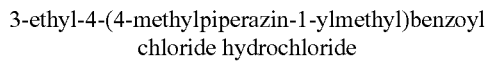
3-ethyl-4-(4-methylpiperazin-1-ylmethyl)benzoyl chloride hydrochloride 2.16 g of 3-ethyl-4-(4-methylpiperazin-1-ylmethyl)benzoic acid obtained in the step 6 was dissolved in 8.3 ml of thionyl chloride and the mixture was heated at reflux for 16 hours. After the reaction solution was air-cooled, diethyl ether was added to the reaction solution and the deposited crystal was collected by filtration, and then washed with diethyl ether to obtain a crude product.

Reference Example 2

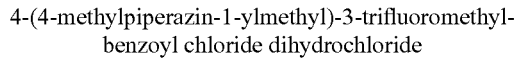
4-(4-methylpiperazin-1-ylmethyl)-3-trifluoromethylbenzoyl chloride dihydrochloride Step 1

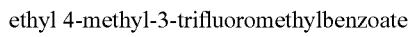
ethyl 4-methyl-3-trifluoromethylbenzoate

This compound was prepared in the same manner as in Reference Example 1 (step 1), except that 4-methyl-3-trifluoromethylbenzoic acid was used.

Pale Yellow Oily Product

Step 2

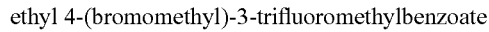
ethyl 4-(bromomethyl)-3-trifluoromethylbenzoate

This compound was prepared in the same manner as in Reference Example 1 (step 2), except that ethyl 4-methyl-3-trifluoromethylbenzoate obtained in the step 1 was used.

Pale Yellow Oily Product

Step 3

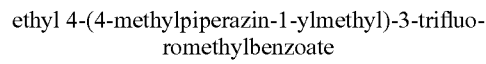
ethyl 4-(4-methylpiperazin-1-ylmethyl)-3-trifluoromethylbenzoate

This compound was prepared in the same manner as in Reference Example 1 (step 3), except that ethyl 4-(bromomethyl)-3-trifluoromethylbenzoate obtained in the step 2 was used.

Yellowish Brown Oily Product

Step 4

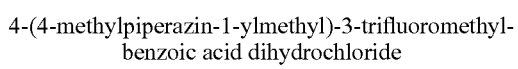
4-(4-methylpiperazin-1-ylmethyl)-3-trifluoromethylbenzoic acid dihydrochloride This compound was prepared in the same manner as in Reference Example 1 (step 6), except that ethyl 4-(4-methylpiperazin-1-ylmethyl)-3-trifluoromethylbenzoate obtained in the step 3 was used, and that the reaction solution was acidified (pH 3) with concentrated hydrochloric acid in place of 1N hydrochloric acid.

Pale Brown Crystals

Melting point: 233-238° C. (with decomposition)

Step 5

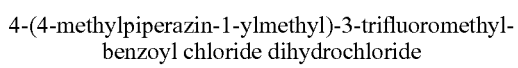
4-(4-methylpiperazin-1-ylmethyl)-3-trifluoromethylbenzoyl chloride dihydrochloride This compound was prepared in the same manner as in Reference Example 1 (step 7), except that 4-(4-methylpiperazin-1-ylmethyl)-3-trifluoromethylbenzoic acid dihydrochloride obtained in the step 4 was used, and that the reaction was heated at reflux for 24 hours.

Colorless Crystals

Reference Example 3

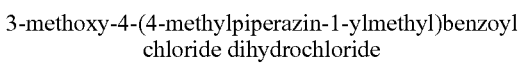
3-methoxy-4-(4-methylpiperazin-1-ylmethyl)benzoyl chloride dihydrochloride This compound was prepared in the same manner as in Reference Example 2 (steps 2 to 5), except that methyl 3-methoxy-4-methylbenzoate was used in the step 2.

Colorless Crystals

Reference Example 4

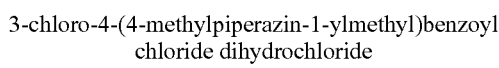
3-chloro-4-(4-methylpiperazin-1-ylmethyl)benzoyl chloride dihydrochloride This compound was prepared in the same manner as in Reference Example 2, except that 3-chloro-4-methylbenzoic acid was used in the step 1.

Colorless Crystals

Reference Example 5

4-(4-ethylpiperazin-1-ylmethyl)-3-trifluoromethyl-benzoyl chloride dihydrochloride This compound was prepared in the same manner as in Reference Example 2, except that N-ethylpiperazine was used in the step 2.

Colorless Crystals

Reference Example 6

3,5-dichloro-4-[(S)-3-(dimethylamino)pyrrolidin-1-ylmethyl]benzoyl chloride hydrochloride Step 1 methyl 3,5-dichloro-4-methylbenzoate

This compound was prepared in the same manner as in Reference Example 1 (step 1), except that 3,5-dichloro-4-methylbenzoic acid (Japanese Unexamined Patent Publication (Kokai) No. 6-192196) was used and methanol was used as the solvent, and that the crude product was purified by silica gel column chromatography.

Pale Yellow Crystals
  Melting point: 49-50° C.

Step 2 methyl 4-(bromomethyl)-3,5-dichlorobenzoate

This compound was prepared in the same manner as in Reference Example 1 (step 2), except that methyl 3,5-dichloro-4-methylbenzoate obtained in the step 1 was used, and that the reaction was heated at reflux for 2 hours.

Orange Crystals
  Melting point: 63-65° C.

Step 3 methyl 3,5-dichloro-4-[(S)-3-(dimethylamino)pyrrolidin-1-ylmethyl]benzoate

This compound was prepared in the same manner as in Reference Example 1 (step 3), except that methyl 4-(bromomethyl)-3,5-dichlorobenzoate obtained in the step 2 and (S)-(−)-3-(dimethylamino)pyrrolidine were used, and that the reaction was conducted at room temperature for 17 hours.

Pale Yellow Oily Product

Step 4

3,5-dichloro-4-[(S)-3-(dimethylamino)pyrrolidin-1-ylmethyl]benzoic acid

This compound was prepared in the same manner as in Reference Example 1 (step 6), except that methyl 3,5-dichloro-4-[(S)-3-(dimethylamino)pyrrolidin-1-ylmethyl]benzoate obtained in the step 3 was used and methanol was used as the solvent, and that after methanol was added to the residue and the resulting mixture was stirred, insolubles were removed by filtration and the solvent in the filtrate was distilled off under reduced pressure to obtain the objective compound.

Pale Orange Amorphous

Step 5

3,5-dichloro-4-[(S)-3-(dimethylamino)pyrrolidin-1-ylmethyl]benzoyl chloride hydrochloride This compound was prepared in the same manner as in Reference Example 1 (step 7), except that 3,5-dichloro-4-[(S)-3-(dimethylamino)pyrrolidin-1-ylmethyl]benzoic acid obtained in the step 4 was used, and that treatment after the reaction was that thionyl chloride was distilled off under reduced pressure, and then the operation of adding of toluene to the residue, followed by azeotropic removal of thionyl chloride was repeated twice.

Pale Yellow Crystals
  Melting point: 210-219° C. (with decomposition)

Reference Example 7

4-(1-methylpiperidin-4-ylidenemethyl)-3-trifluoromethylbenzoyl chloride hydrochloride Step 1 ethyl 4-(dimethoxyphosphorylmethyl)-3-trifluoromethylbenzoate 6.20 g of ethyl 4-(bromomethyl)-3-trifluoromethylbenzoate (Reference Example 2 (step 2)) was dissolved in 12 ml of trimethyl phosphite and the mixture was heated at reflux for 4 hours under an argon atmosphere. After the completion of the reaction, the operation of adding of toluene to the residue, followed by azeotropic removal of trimethyl phosphite was repeated three times. The residue was purified by silica gel column chromatography to obtain 4.96 g of the objective compound as a yellow oily product.

Step 2 ethyl 4-(1-methylpiperidin-4-ylidenemethyl)-3-trifluoromethylbenzoate

Under an argon atmosphere, 624 mg of 60% sodium hydride was washed twice with n-hexane, a solution of 4.96 g of ethyl 4-(dimethoxyphosphorylmethyl)-3-trifluoromethylbenzoate obtained in the step 1 and 1.60 ml of N-methylpiperidone dissolved in 50 ml of 1,2-dimethoxyethane was added, and then the mixture was gradually heated up to 85° C. and heated at reflux for 1 hour. The reaction solution was air-cooled, mixed with ice water, followed by extraction with ethyl acetate twice. The organic layer was washed with saturated saline and dried over anhydrous magnesium sulfate, and then the solvent was distilled off under reduced pressure. The residue was purified by silica gel column chromatography to obtain 3.21 g of the objective compound as a yellow oily product.

Step 3

4-(1-methylpiperidin-4-ylidenemethyl)-3-trifluoromethylbenzoic acid

This compound was prepared in the same manner as in Reference Example 1 (step 6), except that ethyl 4-(1-methylpiperidin-4-ylidenemethyl)-3-trifluoromethylbenzoate obtained in the step 2 was used.

Yellow Amorphous

Step 4

4-(1-methylpiperidin-4-ylidenemethyl)-3-trifluoromethylbenzoyl chloride hydrochloride This compound was prepared in the same manner as in Reference Example 1 (step 7), except that 4-(1-methylpiperidin-4-ylidenemethyl)-3-trifluoromethylbenzoic acid obtained in the step 3 was used, and that treatment after the reaction was that thionyl chloride was distilled off under reduced pressure, and then the operation of adding of toluene to the residue, followed by azeotropic removal of thionyl chloride was repeated three times.

Green-Brown Amorphous

Reference Example 8

4-(1-methylpiperidin-4-ylmethyl)-3-trifluoromethylbenzoyl chloride hydrochloride Step 1 ethyl 4-(1-methylpiperidin-4-ylmethyl)-3-trifluoromethylbenzoate 1.57 g of ethyl 4-(1-methylpiperidin-4-ylidenemethyl)-3-trifluoromethylbenzoate (Reference Example 7 (step 2)) was dissolved in 32 ml of methanol and 78 mg of 10% palladium-carbon was added, and then the mixture was hydrogenated at room temperature under 1 atm for 24 hours. The catalyst was removed by filtration and the solvent in the filtrate was distilled off under reduced pressure. The mixture was again dissolved in 32 ml of methanol and 78 mg of 10% palladium-carbon was added thereto, and then the mixture was hydrogenated at room temperature under 1 atm for 4 hours. Further, 78 mg of palladium-carbon was added and the mixture was hydrogenated at room temperature under 1 atm for 24 hours. 78 mg of palladium-carbon was further added and the mixture was hydrogenated at room temperature under 1 atm for 19 hours. The catalyst was removed by filtration and the solvent in the filtrate was distilled off under reduced pressure to obtain 1.54 g of the objective compound as a green oily product.

Step 2

4-(1-methylpiperidin-4-ylmethyl)-3-trifluoromethylbenzoic acid

This compound was prepared in the same manner as in Reference Example 1 (step 6), except that ethyl 4-(1-methylpiperidin-4-ylmethyl)-3-trifluoromethylbenzoate obtained in the step 1 was used, and that the crude product was mixed with methanol and stirred, insolubles were removed by filtration, the filtrate was distilled off under reduced pressure, and then the residue was crystallized by adding acetonitrile.

Colorless Crystals
Melting point: 247-250° C. (with decomposition)

Step 3

4-(1-methylpiperidin-4-ylmethyl)-3-trifluoromethylbenzoyl chloride hydrochloride This compound was prepared in the same manner as in Reference Example 1 (step 7), except that 4-(1-methylpiperidin-4-ylmethyl)-3-trifluoromethylbenzoic acid obtained in the step 2 was used, and that treatment after the reaction was that thionyl chloride was distilled off under reduced pressure, and then the operation of adding of toluene to the residue, followed by azeotropic removal of thionyl chloride was repeated twice.

Pale Green Crystals
Melting point: 157-164° C. (with decomposition)

Reference Example 9

3-difluoromethyl-4-(4-methylpiperazin-1-ylmethyl)benzoyl chloride hydrochloride Step 1 t-butyl 3-iodo-4-methylbenzoate 26.20 g of 3-iodo-4-methylbenzoic acid was suspended in 500 ml of t-butyl alcohol and 43.65 g of di-t-butyl dicarbonate was added, and then the mixture was stirred at room temperature. To the mixture was added 1.22 g of 4-(dimethylamino)pyridine, the mixture was stirred at room temperature for 10 minutes, and then the mixture was heated at reflux for 4 hours. After the solvent was distilled off under reduced pressure, the residue was mixed with ethyl acetate and further distilled off under reduced pressure. After 10 ml of ethyl acetate and 30 ml of n-hexane were added to the residue and the resulting mixture was stirred. Insolubles were removed by filtration and the solvent in the filtrate was distilled off under reduced pressure. 30 ml of n-hexane was added to the residue and the same operation as described above was performed with the mixture. The residue was purified by silica gel column chromatography to obtain 22.01 g of the objective compound as a colorless oily product.

Step 2 t-butyl 3-formyl-4-methylbenzoate 7.00 g of t-butyl 3-iodo-4-methylbenzoate obtained in the step 1 was dissolved in 200 ml of anhydrous tetrahydrofuran and the mixture was stirred under cooling in a dry ice/acetone bath under an argon atmosphere. 15.5 ml of n-butyllithium (1.6 M n-hexane solution) was added dropwise at the internal temperature of −66° C. or less. After stirring for 5 minutes, 3.4 ml of N,N-dimethylformamide was added dropwise over 5 minutes and the mixture was stirred for 50 minutes. 100 ml of water was slowly added dropwise thereto. The mixture was heated up to room temperature, followed by extraction with ethyl acetate. The mixture was dried over anhydrous magnesium sulfate and the solvent was distilled off under reduced pressure. The residue was purified by silica gel column chromatography to obtain 3.76 g of the objective compound as colorless crystals.

Melting point: 53-55° C.

Step 3 t-butyl 3-difluoromethyl-4-methylbenzoate 3.76 g of t-butyl 3-formyl-4-methylbenzoate obtained in the step 2 was dissolved in 17 ml of anhydrous methylene chloride and 2.71 ml of diethylaminosulfur trifluoride (DAST) was added at room temperature, followed by stirring for 7 hours. The reaction solution was mixed with ethyl acetate, washed with aqueous saturated sodium hydrogen carbonate and dried over anhydrous magnesium sulfate, and then the solvent was distilled off under reduced pressure. The residue was purified by silica gel column chromatography to obtain 3.10 g of the objective compound as a pale yellow oily product.

Step 4 t-butyl 4-(bromomethyl)-3-difluoromethylbenzoate

This compound was prepared in the same manner as in Reference Example 1 (step 2), except that t-butyl 3-difluoromethyl-4-methylbenzoate obtained in the step 3 was used.

Step 5 t-butyl 3-difluoromethyl-4-(4-methylpiperazin-1-ylmethyl)benzoate

This compound was prepared in the same manner as in Reference Example 1 (step 3), except that t-butyl 4-(bromomethyl)-3-difluoromethylbenzoate obtained in the step 4 was used.

Colorless Oily Product

Step 6

3-difluoromethyl-4-(4-methylpiperazin-1-ylmethyl)benzoic acid

This compound was prepared in the same manner as in Reference Example 1 (step 6), except that t-butyl 3-difluoromethyl-4-(4-methylpiperazin-1-ylmethyl)benzoate obtained in the step 5 was used, and that the resulting crude product was mixed with methanol, insolubles were removed by filtration, the filtrate was distilled off under reduced pressure, and then the residue was crystallized from acetonitrile.

Colorless Crystals

Melting point: 160-167° C. (with decomposition)

Step 7

3-difluoromethyl-4-(4-methylpiperazin-1-ylmethyl)benzoyl chloride hydrochloride

This compound was prepared in the same manner as in Reference Example 1 (step 7), except that 3-difluoromethyl-4-(4-methylpiperazin-1-ylmethyl)benzoic acid obtained in the step 6 was used.

Colorless Crystals

Melting point: 217-222° C. (with decomposition)

Reference Example 10

3-fluoromethyl-4-(1-methylpiperazin-4-ylmethyl)benzoyl chloride hydrochloride

Step 1 t-butyl 4-(bromomethyl)-3-iodobenzoate

This compound was prepared in the same manner as in Reference Example 1 (step 2), except that t-butyl 3-iodo-4-methylbenzoate (Reference Example 9 (step 1) was used.

Purple Oily Product

Step 2 t-butyl 3-iodo-4-(1-methylpiperidin-4-ylidenemethyl)benzoate

This compound was prepared in the same manner as in Reference Example 7 (steps 1 and 2), except that t-butyl 4-(bromomethyl)-3-iodobenzoate obtained in the step 1 was used.

Pale Yellow Oily Product

Step 3 t-butyl 3-formyl-4-(1-methylpiperidin-4-ylidenemethyl)benzoate

This compound was prepared in the same manner as in Reference Example 9 (step 2), except that t-butyl 3-iodo-4-(1-methylpiperidin-4-ylidenemethyl)benzoate obtained in the step 2 was used, and that the resulting crude product was not purified.

Step 4 t-butyl 3-hydroxymethyl-4-(1-methylpiperidin-4-ylidenemethyl)benzoate 4.75 g of t-butyl 3-formyl-4-(1-methylpiperidin-4-ylidenemethyl)benzoate obtained in the step 3 was dissolved in 47.5 ml of anhydrous methanol and the mixture was stirred under ice-water cooling. 689 mg of sodium borohydride was added thereto and the mixture was stirred under cooling for 3.5 hours. The reaction solution was mixed with ice and an aqueous saturated sodium hydrogen carbonate solution, followed by extraction with ethyl acetate three times, and dried over anhydrous magnesium sulfate, and then the solvent was distilled off under reduced pressure. The residue was purified by silica gel column chromatography to obtain 2.41 g of the objective compound as a yellow amorphous.

Step 5 t-butyl 3-hydroxymethyl-4-(1-methylpiperidin-4-ylmethyl)benzoate 2.41 g of t-butyl 3-hydroxymethyl-4-(1-methylpiperidin-4-ylidenemethyl)benzoate obtained in the step 4 was dissolved in methanol and 241 mg of 10% palladium-carbon was added, and then the mixture was hydrogenated at room temperature under 4 atm for 2 hours. 241 mg of 10% palladium-carbon was added and the mixture was further hydrogenated at room temperature under 4 atm for 12 hours. The catalyst was removed by filtration and 482 mg of 10% palladium-carbon was added to the filtrate, and then the mixture was again hydrogenated at room temperature under 4 atm for 22 hours. The catalyst was removed by filtration and the solvent was distilled off under reduced pressure to obtain 2.34 g of the objective compound as a pale green amorphous.

Step 6 t-butyl 3-fluoromethyl-4-(1-methylpiperidin-4-ylmethyl)benzoate 982 mg of DAST was dissolved in 10 ml of anhydrous dichloromethane and the mixture was stirred under cooling in a dry ice/acetone bath under an argon atmosphere. A solution of 1.77 g of t-butyl 3-hydroxymethyl-4-(1-methylpiperidin-4-ylmethyl)benzoate obtained in the step 5 in 18 ml of anhydrous dichloromethane was added dropwise for 3 hours and the reaction solution was stirred for 2 hours. After heating up to room temperature, saturated sodium hydrogen carbonate was added to the reaction solution to separate the aqueous layer. The aqueous layer was subjected to extraction with ethyl acetate twice. The organic layers were combined and dried over anhydrous magnesium sulfate, and then the solvent was distilled off under reduced pressure. The residue was purified by silica gel column chromatography to obtain 954 mg of a crude product as a yellow oily product.

Step 7

3-fluoromethyl-4-(1-methylpiperidin-4-ylmethyl)benzoic acid

This compound was prepared in the same manner as in Reference Example 1 (step 6), except that t-butyl 3-fluoromethyl-4-(1-methylpiperidin-4-ylmethyl)benzoate obtained in the step 6 was used, and that water was distilled off, methanol was added to the residue, insolubles were removed by filtration, and then the solvent in the filtrate was distilled off under reduced pressure.

White Amorphous

Step 8

3-fluoromethyl-4-(1-methylpiperidin-4-ylmethyl)benzoyl chloride hydrochloride

This compound was prepared in the same manner as in Reference Example 1 (step 7), except that 3-fluoromethyl-4-(1-methylpiperidin-4-ylmethyl)benzoic acid obtained in the step 7 was used, and that treatment after the reaction was that thionyl chloride was distilled off under reduced pressure, and then the operation of adding of toluene to the residue, followed by azeotropic removal of thionyl chloride was repeated twice.

Orange Amorphous

Reference Example 11

4-(1-methylpiperidin-4-yloxy)-3-trifluoromethylbenzoyl chloride hydrochloride

Step 1

4-(1-methylpiperidin-4-yloxy)-3-trifluoromethylbenzonitrile 6.68 g of potassium t-butoxide was suspended in 40 ml of anhydrous tetrahydrofuran and a solution of 6.85 g of 1-methyl-4-hydroxypiperidine in 20 ml of anhydrous tetrahydrofuran was added dropwise over 35 minutes while stirring under ice-water cooling and further the mixture was stirred for 30 minutes. On the other hand, 7.50 g of 4-fluoro-3-trifluoromethylbenzonitrile was dissolved in 40 ml of anhydrous tetrahydrofuran, the mixture was stirred under cooling in a dry ice/acetone bath, and the solution prepared earlier was added dropwise at the internal temperature of −70° C. After adding dropwise, the reaction solution was stirred overnight while naturally heating up to room temperature. The reaction solution was ice-cooled, an aqueous saturated ammonium chloride solution and water were added thereto, and then the solvent was distilled off under reduced pressure. The residue was subjected to extraction with ethyl acetate twice. The extracts were washed in turn with water and saturated saline and dried over anhydrous magnesium sulfate, and then the solvent was distilled off under reduced pressure. The residue was purified by silica gel column chromatography to obtain 7.31 g of the objective compound as colorless crystals.

Melting point: 66-69° C.

Step 2

4-(1-methylpiperidin-4-yloxy)-3-trifluoromethylbenzoic acid 1.0 g of 4-(1-methylpiperidin-4-yloxy)-3-trifluoromethylbenzonitrile obtained in the step 1 was dissolved in 20 ml of ethanol and 17.6 ml of a 1N aqueous sodium hydroxide solution was added thereto, and the mixture was heated at reflux for 24 hours. After the solvent was distilled off under reduced pressure, water was added to the residue. The aqueous layer was washed once with diethyl ether and neutralized with 17.6 ml of 1N hydrochloric acid under ice-water cooling. After water was distilled off under reduced pressure, the operation of adding methanol to the residue, followed by azeotropic removal of water was repeated three times. After the addition of methanol and stirring, insolubles were removed by filtration and the solvent in the filtrate was distilled off under reduced pressure. The resulting crude crystal was washed with acetonitrile to obtain 0.96 g of the objective compound as colorless crystals.

Melting point: 254° C. (with decomposition)

Step 3

4-(1-methylpiperidin-4-yloxy)-3-trifluoromethylbenzoyl chloride hydrochloride 800 mg of 4-(1-methylpiperidin-4-yloxy)-3-trifluoromethylbenzoic acid obtained in the step 2 was suspended in anhydrous toluene and 0.94 ml of thionyl chloride and 80 μl of anhydrous N,N-dimethylformamide were added in turn, and then the mixture was heated at reflux for 18 hours. After stirring under ice-water cooling, the deposited crystals were collected by filtration and then washed with toluene to obtain 500 mg of the objective compound as colorless crystals.

Melting point: 242° C. (with decomposition)

Reference Example 12

4-[(R)-3-(dimethylamino)pyrrolidin-1-ylmethyl)-3-trifluoromethylbenzoic acid

This compound was prepared in the same manner as in Reference Example 2 (steps 1 to 4), except that (R)-(+)-3-(dimethylamino)pyrrolidine was used in the step 3, and that the reaction solution was neutralized (pH 7) with 1N hydrochloric acid in place of concentrated hydrochloric acid in the step 4 and the crude product was purified by silica gel column chromatography.

Colorless Crystals

Melting point: 206-209° C. (with decomposition)

Reference Example 13

4-[4-(t-butoxycarbonyl)piperazin-1-ylmethyl]-3-trifluoromethylbenzoic acid

This compound was prepared in the same manner as in Reference Example 2 (steps 1 to 4), using N-(t-butoxycarbonyl)piperazine in the step 3. However, in the step 4, the reaction was conducted at room temperature for 3 hours; the reaction solution was neutralized (pH 7) with 1N hydrochloric acid in place of concentrated hydrochloric acid, followed by extraction with ethyl acetate; and the resulting crude product obtained by purification with silica gel column chromatography was washed with n-hexane.

Colorless Crystals

Melting point: 131-136° C. (with decomposition)

Reference Example 14

4-[4-(2-fluoroethyl)piperazin-1-ylmethyl]-3-trifluoromethylbenzoic acid

Step 1 ethyl 4-[4-(2-hydroxyethyl)piperazin-1-ylmethyl]-3-trifluoromethylbenzoate

This compound was prepared in the same manner as in Reference Example 2 (step 3), except that 1-(2-hydroxyethyl)piperazine was used.

Yellow Oily Product

Step 2 ethyl 4-[4-(2-fluoroethyl)piperazin-1-ylmethyl]-3-trifluoromethylbenzoate 4.50 g of ethyl 4-[4-(2-hydroxyethyl)piperazin-1-ylmethyl]-3-trifluoromethylbenzoate obtained in the step 1 was dissolved in 90 ml of anhydrous dichloromethane and the mixture was stirred under cooling in a dry ice/acetone bath under an argon atmosphere. A solution of 4.03 g of DAST in 50 ml of anhydrous dichloromethane was added dropwise for 20 minutes and the reaction solution was stirred for 10 minutes. The reaction solution was stirred for 1 hour under ice-water cooling and then stirred at room temperature for 2 hours. The reaction solution was alkalified (pH 9) by adding ice and 100 ml of an aqueous saturated sodium hydrogen carbonate solution, and then insolubles were removed by filtration. The filtrate was subjected to extraction with ethyl acetate and dried over anhydrous magnesium sulfate, and then the solvent was distilled off under reduced pressure. The residue was purified by silica gel column chromatography to obtain 2.16 g of the objective compound as a yellow oily product.

Step 3

4-[4-(2-fluoroethyl)piperazin-1-ylmethyl]-3-trifluoromethylbenzoic acid

This compound was prepared in the same manner as in Reference Example 1 (step 6), except that ethyl 4-[4-(2-fluoroethyl)piperazin-1-ylmethyl]-3-trifluoromethylbenzoate obtained in the step 2 was used, and that after neutralization, the aqueous layer was followed by extraction with ethyl acetate, the separated aqueous layer was mixed with saturated saline, subjected to extraction with ethyl acetate, and further mixed with a table salt, followed by extraction with ethyl acetate five times.

Colorless Crystals

Melting point: 152-155° C. (with decomposition)

Reference Example 15

4-{4-[2-(t-butyldimethylsilanoxy)ethyl]piperazin-1-ylmethyl}-3-trifluoromethylbenzoic acid Step 1 ethyl 4-[4-(2-(t-butyldimethylsilanoxyethyl)piperazin-1-ylmethyl)-3-trifluoromethylbenzoate 2.82 g of ethyl 4-[4-(2-hydroxyethyl)piperazin-1-ylmethyl]-3-trifluoromethylbenzoate (Reference Example 14 (step 1)) was dissolved in anhydrous N,N-dimethylformamide and 1.33 g of imidazole and 1.42 g of t-butyldimethylchlorosilane were added in turn, and then the mixture was stirred at room temperature for 1 hour. The reaction solution was mixed with water, followed by extraction with ethyl acetate, and dried over anhydrous magnesium sulfate, and then the solvent was distilled off under reduced pressure. The residue was purified by silica gel column chromatography to obtain 3.70 g of the objective compound as a pale yellow oily product.

Step 2

4-[4-(2-(t-butyldimethylsilanoxyethyl)piperazin-1-ylmethyl)-3-trifluoromethylbenzoic acid This compound was prepared in the same manner as in Reference Example 1 (step 6), except that ethyl 4-[4-(2-(t-butyldimethylsilanoxyethyl)piperazin-1-ylmethyl)-3-trifluoromethylbenzoate obtained in the step 1 was used, and that ethanol was used as the solvent and after neutralization, the aqueous layer was subjected to extraction with ethyl acetate twice and the organic layer was washed with saturated saline.

Pale Yellow Amorphous

Reference Example 16

4-[1-(t-butoxycarbonyl)-2-carbamoylpiperazin-4-ylmethyl]-3-trifluoromethylbenzoic acid Step 1 ethyl 4-(3-carbamoylpiperazin-1-ylmethyl)-3-trifluoromethylbenzoate

This compound was prepared in the same manner as in Reference Example 2 (step 3), except that 2-carbamoylpiperazine was used.

Colorless Oily Product

Step 2 ethyl 4-[1-(t-butoxycarbonyl)-2-carbamoylpiperazin-4-ylmethyl]-3-trifluoromethylbenzoate 3.07 g of ethyl 4-(3-carbamoylpiperazin-1-ylmethyl)-3-trifluoromethylbenzoate obtained in the step 1 and 0.20 g of 4-(dimethylamino)pyridine were dissolved in 34 ml of acetonitrile and 1.96 g of di-t-butyl dicarbonate was added thereto, and then the mixture was stirred at room temperature for 3 hours. The deposited crystal was collected by filtration and then washed with a small amount of acetonitrile to obtain 2.08 g of the objective compound as colorless crystals.
Melting point: 124-125° C.

Step 3

4-[1-(t-butoxycarbonyl)-2-carbamoylpiperazin-4-ylmethyl]-3-trifluoromethylbenzoic acid 2.84 g of ethyl 4-[1-(t-butoxycarbonyl)-2-carbamoylpiperazin-4-ylmethyl]-3-trifluoromethylbenzoate obtained in the step 2 was suspended in 15 ml of methanol and 10 ml of a 1N aqueous sodium hydroxide solution was added thereto, and then the reaction solution was stirred at room temperature for 18 hours. The reaction solution was neutralized by adding 10 ml of 1N hydrochloric acid. The deposited crystal was collected by filtration and then washed with water to obtain 2.51 g of the objective compound as colorless crystals.
Melting point: 230-233° C. (with decomposition)

Reference Example 17

4-[(S)-3-(t-butoxycarbonylamino)-2-oxopyrrolidin-1-ylmethyl]-3-trifluoromethylbenzoic acid Step 1 ethyl 4-[(S)-3-(t-butoxycarbonylamino)-2-oxopyrrolidin-1-ylmethyl]-3-trifluoromethylbenzoate 669 mg of (S)-3-(t-butoxycarbonylamino)pyrrolidin-2-one (J. Med. Chem., 1999, 42, 3557-3571) was dissolved in 30 ml of tetrahydrofuran/N,N-dimethylformamide (9:1) and the mixture was stirred under ice cooling. 60% sodium hydride was added thereto and the mixture was stirred for 20 minutes. A solution (3 ml) of ethyl 4-(bromomethyl)-3-trifluoromethylbenzoate (Reference Example 2 (step 2)) in tetrahydrofuran was added dropwise, followed by stirring at room temperature for 6 hours after removing an ice bath. The reaction solution was poured into an aqueous saturated ammonium chloride solution, followed by extraction with ethyl acetate twice, and dried over anhydrous magnesium sulfate, and then the solvent was distilled off under reduced pressure. The residue was purified by silica gel column chromatography to obtain 867 mg of the objective compound as pale yellow crystals.
Melting point: 93-95° C.

Step 2

4-((S)-3-(t-butoxycarbonylamino)-2-oxopyrrolidin-1-ylmethyl)-3-trifluoromethylbenzoic acid 829 mg of ethyl 4-((S)-3-(t-butoxycarbonylamino)-2-oxopyrrolidin-1-ylmethyl)-3-trifluoromethylbenzoate obtained in the step 1 was dissolved in 5 ml of methanol and 2.9 ml of a 1N aqueous sodium hydroxide solution was added thereto, and then the reaction solution was stirred at room temperature for 20 hours. The reaction solution was neutralized by adding 2.9 ml of 1N hydrochloric acid and methanol was distilled off under reduced pressure. The residue was mixed with water, followed by extraction with ethyl acetate, and then dried over anhydrous magnesium sulfate. The solvent was distilled off under reduced pressure to obtain 800 mg of the objective compound as a pale yellow amorphous.

Reference Example 18

4-methyl-3-[4-(5-pyrimidinyl)pyrimidin-2-ylamino]aniline

Step 1

3-(dimethylamino)-1-(5-pyrimidinyl)-2-propen-1-one 6.01 g of N,N-dimethylformamide dimethylacetal was added to 1.54 g of 5-acetylpyrimidine (Khim. Geterotsikl. Soedim., 1981, (7), 958-962) and the mixture was heated at reflux for 15 hours. After the reaction solution was air-cooled, a small amount of diisopropyl ether was added and the deposited crystal was collected by filtration to obtain 1.52 g of the objective compound as reddish brown crystals.
Melting point: 133-135° C.

Step 2

1-(2-methyl-5-nitrophenyl)guanidine

To 135 g of 1-(2-methyl-5-nitrophenyl)guanidine nitrate (Japanese Unexamined Patent Publication (Kokai) No. 6-87834), 21 g of sodium hydroxide in 1.0 L of a cold aqueous solution was directly added, followed by stirring at room temperature for 10 minutes. The crystals were filtered, sufficiently washed with water and then forced-air dried at 60° C. to obtain 102 g of the objective compound as pale yellow crystals.
Melting point: 135-142° C.

Step 3

1-methyl-4-nitro-2-[4-(5-pyrimidinyl)pyrimidin-2-ylamino]benzene

To 1.51 g of 3-(dimethylamino)-1-(5-pyrimidinyl)-2-propen-1-one obtained in the step 1, 1.66 g of 1-(2-methyl-5-nitrophenyl)guanidine obtained in the step 2 was added, followed by stirring at 120° C. for 2 hours. To the mixture, 2-propanol was added and the crystals were collected by filtration and then washed in turn with 2-propanol and diethyl ether to obtain 1.95 g of the objective compound as pale brown crystals.
Melting point: 200-203° C.

Step 4

4-methyl-3-[4-(5-pyrimidinyl)pyrimidin-2-ylamino]aniline 18.50 g of 1-methyl-4-nitro-2-[4-(5-pyrimidinyl)pyrimidin-2-ylamino]benzene obtained in the step 3 was suspended in 1.3 L of tetrahydrofuran-methanol (1:1) and 7.40 g of 10% palladium-carbon was added under an argon atmosphere.

9.06 ml of formic acid was added thereto under stirring at room temperature, and then the reaction solution was heated at reflux for 1 hour. After the reaction solution was air-cooled, the catalyst was removed by filtration and washed with methanol, and the solvent in the filtrate was then distilled off under reduced pressure. The residue was dissolved in chloroform. To the residue, an aqueous saturated sodium hydrogen carbonate solution was added to separate the aqueous layer. The aqueous layer was subjected to extraction with chloroform twice. The organic layers were combined and dried over anhydrous magnesium sulfate, and then the solvent was distilled off under reduced pressure. The amorphous obtained by purification of the residue with silica gel column chromatography was crystallized by adding chloroform to obtain 11.97 g of the objective compound as pale yellow crystals.

Melting point: 164-167° C.

Reference Example 19

3-[4-(5-bromopyridin-3-yl)pyrimidin-2-ylamino]-4-methylaniline

Step 1

5-bromonicotinoyl chloride

To 5.00 g of 5-bromonicotinic acid, 74 ml of thionyl chloride was added and the mixture was heated at reflux for 6 hours. After the solvent was distilled off under reduced pressure, the crystal was washed with diisopropyl ether and collected by filtration to obtain 4.09 g of the objective compound as colorless crystals.

Melting point: 72-74° C.

Step 2

3-acetyl-5-bromopyridine 1.24 g of ground magnesium chloride was suspended in 13 ml of toluene and 6.2 ml of triethylamine and 2.93 g of diethyl malonate were added in turn. After stirring at room temperature for 1.5 hours, a suspension of 4.08 g of 5-bromonicotinoyl chloride obtained in the step 1 in 10 ml of toluene was added dropwise over 15 minutes, followed by stirring at room temperature for 2 hours. After neutralizing with 40 ml of 1N hydrochloric acid, the aqueous layer was separated. The aqueous layer was further subjected to extraction with diethyl ether and the organic layers were combined, and then the solvent was distilled off under reduced pressure. To the resulting oily product, dimethyl sulfoxide-water (17 ml-0.7 ml) was added, followed by stirring with heating at 150 to 160° C. for 2 hours. The reaction solution was air-cooled, and then water was added. Then, the deposited crystals were collected by filtration. The deposited crystals were dissolved in ethyl acetate, washed in turn with water and an aqueous saturated sodium hydrogen carbonate solution and then dried over anhydrous magnesium sulfate. 0.60 g of activated carbon (Kyoryoku Shirasagi MOIWY433) was added and, after standing for 10 minutes, activated carbon was removed by filtration, the filtrate was concentrated under reduced pressure. The residue was purified by silica gel column chromatography to obtain 0.89 g of the objective compound as pale yellow crystals.

Melting point: 87-89.5° C.

Step 3

1-(5-bromopyridin-3-yl)-3-(dimethylamino)-2-propen-1-one

To 859 mg of 3-acetyl-5-bromopyridine obtained in the step 2, 563 mg of N,N-dimethylformamide dimethyl acetal was added and the mixture was heated at reflux for 1 hour. After air cooling, the reaction solution was directly purified by silica gel column chromatography. The resulting crude crystals were washed with diethyl ether and then collected by filtration to obtain 860 mg of the objective compound as yellow crystals.

Melting point: 131-131.5° C.

Step 4

2-[4-(5-bromopyridin-3-yl)pyrimidin-2-ylamino]-1-methyl-4-nitrobenzene

To 833 mg of 1-(5-bromopyridin-3-yl)-3-(dimethylamino)-2-propen-1-one obtained in the step 3 and 634 mg of 1-(2-methyl-5-nitrophenyl)guanidine (Reference Example 6 (step 2)), 7 ml of 2-propanol was added and the mixture was heated at reflux for 17 hours. After the reaction solution was air-cooled, the deposited crystals were collected by filtration and washed with diethyl ether to obtain 823 mg of the objective compound as pale yellow crystals.

Melting point: 206-208° C.

Step 5

3-[4-(5-bromopyridin-3-yl)pyrimidin-2-ylamino]-4-methylaniline

To 807 mg of 2-[4-(5-bromopyridin-3-yl)pyrimidin-2-ylamino]-1-methyl-4-nitrobenzene obtained in the step 4, 5 ml of concentrated hydrochloric acid was added and a solution of 2.36 g of tin chloride (II) dihydrate in 3.5 ml of concentrated hydrochloric acid was added while stirring with heating at 55° C. The mixture was gradually heated up to 100° C. and further stirred with heating at 100° C. for 15 minutes. After the reaction solution was air-cooled, water was added and alkalified with a 10% aqueous sodium hydroxide solution. After the addition of chloroform and stirring for a while, insolubles were removed by filtration and the aqueous layer was separated. The aqueous layer was further subjected to extraction with chloroform and the organic layers were combined and, after drying over anhydrous magnesium sulfate, the solvent was distilled off under reduced pressure. The residue was purified by silica gel column chromatography to obtain a crude product. The crude product was crystallized by adding diethyl ether-ethyl acetate and the crystals were collected by filtration to obtain 528 mg of the objective compound as yellow crystals.

Melting point: 129.5-130° C.

Reference Example 20

4-methyl-3-[6-(3-pyridyl)pyrimidin-4-ylamino]aniline

Step 1

2-[(6-chloro)pyrimidin-4-ylamino]-1-methyl-4-nitrobenzene 2.64 g of 2-methyl-5-nitroaniline and 10.33 g of 4,6-dichloropyrimidine were stirred with heating at 110° C. for 16 hours. After air cooling, the reaction solution was dissolved in methanol. An aqueous saturated sodium hydrogen carbonate solution and ethyl acetate were added to separate the aqueous layer. The aqueous layer was further subjected to extraction with ethyl acetate twice. The organic layers were combined and dried over anhydrous magnesium sulfate, and then the solvent was distilled off under reduced pressure. The residue was purified by silica gel column chromatography to obtain a crude product. The crude product was washed with diisopropyl ether to obtain 3.61 g of the objective compound as yellow crystals.

Melting point: 161-163° C.

Step 2

1-methyl-4-nitro-2-[6-(3-pyridyl)pyrimidin-4-ylamino]benzene 2.00 g of 2-[(6-chloro)pyrimidin-4-ylamino]-1-methyl-4-nitrobenzene obtained in the step 1 was dissolved in 80 ml of tetrahydrofuran, 1.22 g of diethyl(3-pyridyl)borane and 870 mg of tetrakis(triphenylphosphine)palladium (0) were added in turn, and then the mixture was stirred at room temperature under an argon atmosphere. To the mixture were added 1.27 g of potassium hydroxide and 10 ml of water and then the reaction solution was heated at reflux for 6 hours. The reaction solution was mixed with water, followed by extraction with ethyl acetate three times, and dried over anhydrous magnesium sulfate, and then the solvent was distilled off under reduced pressure. The crude crystals were washed with ethyl acetate to obtain 1.43 g of the objective compound as brown crystals.

Melting point: 187-192° C.

Step 3

4-methyl-3-[6-(3-pyridyl)pyrimidin-4-ylamino]aniline 1.85 g of 1-methyl-4-nitro-2-[6-(3-pyridyl)pyrimidin-4-ylamino]benzene obtained in the step 2 was suspended in 74 ml of anhydrous methanol and 555 mg of 10% palladium-carbon was added. 3.80 g of ammonium formate was added under an argon atmosphere and the mixture was heated at reflux at a bath temperature of 90° C. for 4 hours. The catalyst was removed by filtration and the solvent in the filtrate was distilled off under reduced pressure. The residue was mixed with water and was subjected to extraction with ethyl acetate twice. The organic layer was dried over anhydrous magnesium sulfate, and then the solvent was distilled off under reduced pressure. The residue was crystallized by adding ethyl acetate to obtain 1.41 g of the objective compound as pale yellow crystals.

Melting point: 176-179° C.

Reference Example 21

4-methyl-3-[6-(5-pyrimidinyl)pyrimidin-4-ylamino]aniline

Step 1

1-methyl-4-nitro-2-[6-(5-pyrimidinyl)pyrimidin-4-ylamino]benzene 3.28 g of 2-[(6-chloro)pyrimidin-4-ylamino]-1-methyl-4-nitrobenzene (Reference Example 20 (step 1)) were dissolved with heating in 130 ml of anhydrous ethanol. 1.69 g of dihydroxy(5-pyrimidinyl)borane was added, and then deaeration was performed, followed by purging with argon. 5.82 g of potassium carbonate and 2.15 g of tetrakis(triphenylphosphine)palladium (0) were added in turn, and then the mixture was heated at reflux for 7.5 hours. The reaction solution was mixed with water, followed by extraction with ethyl acetate twice, and dried over anhydrous magnesium sulfate, and then the solvent was distilled off under reduced pressure. The residue was crystallized by adding chloroform-methanol to obtain 808 mg of the objective compound as ocherous crystals.

Melting point: 257-261° C. (with decomposition)

Step 2

4-methyl-3-[6-(5-pyrimidyl)pyrimidin-4-ylamino]aniline

This compound was prepared in the same manner as in Reference Example 20 (step 3), except that 1-methyl-4-nitro-2-[6-(5-pyrimidyl)pyrimidin-4-ylamino]benzene obtained in the step 1 was used, and that the reaction was conducted for 1.5 hours.

Yellow Crystals
Melting point: 98-102° C. (with decomposition)

Reference Example 22

4-methyl-3-[4-(5-pyrimidinyl)pyridin-2-ylamino]aniline

Step 1

2-[(4-chloro)pyridin-2-ylamino]-1-methyl-4-nitrobenzene

To 2.00 g of 2,4-dichloropyridine, 2.26 g of 2-methyl-5-nitroaniline, 121 mg of palladium (II) acetate, 336 mg of (±)-2,2'-bis(diphenylphosphino)-1,1'-binaphthyl [(±)-BINAP] and 6.16 g of cesium carbonate, 120 ml of toluene was added, and then the mixture was stirred with heating at 70° C. for 23 hours under an argon atmosphere. After insolubles were removed by filtration, the solvent was distilled off under reduced pressure. The residue was purified by silica gel column chromatography to obtain a crude product. The crude product was washed with diethyl ether to obtain 1.22 g of the objective compound as yellow crystals.

Melting point: 130-133° C.

Step 2

1-methyl-4-nitro-2-[4-(5-pyrimidinyl)pyridin-2-ylamino]benzene

To 120 ml of deaerated tetrahydrofuran-water (1:1), 1.73 g of 2-[(4-chloro)pyridin-2-ylamino]-1-methyl-4-nitrobenzene obtained in the step 1, 890 mg of dihydroxy(5-pyrimidinyl)borane, 3.10 g of potassium carbonate and 1.15 g of tetrakis(triphenylphosphine)palladium (0) were added in turn and the mixture was stirred with heating at 80° C. for 46 hours under an argon atmosphere. The reaction solution was diluted with ethyl acetate to separate the aqueous layer, and then the aqueous layer was further subjected to extraction with ethyl acetate. The organic layers were combined and dried over anhydrous magnesium sulfate, and then the solvent was distilled off under reduced pressure. The residue was purified by silica gel column chromatography to obtain a crude product. The crude product was washed with diethyl ether to obtain 820 mg of the objective compound as orange crystals.

Melting point: 229-230° C. (with decomposition)

Step 3

4-methyl-3-[4-(5-pyrimidinyl)pyridin-2-ylamino] aniline 163 mg of 1-methyl-4-nitro-2-[4-(5-pyrimidinyl)pyridin-2-ylamino]benzene obtained in the step 2 was dissolved in 32 ml of tetrahydrofuran-methanol (1:1) and 98 mg of 10% palladium-carbon was added. Furthermore, 284 mg of ammonium formate was added and the mixture was heated at reflux at a bath temperature of 90° C. for 40 minutes. The catalyst was removed by filtration and the solvent in the filtrate was distilled off under reduced pressure. To the residue, water and ethyl acetate were added to separate the aqueous layer. The aqueous layer was further subjected to extraction with ethyl acetate. The organic layers were combined and dried over anhydrous magnesium sulfate, and then the solvent was distilled off under reduced pressure. The residue was purified by silica gel column chromatography to obtain 149 mg of the objective compound as pale yellow crystals.

Melting point: 179-180° C.

Reference Example 23

4-methyl-3-[4-(3-pyridyl)pyridin-2-ylamino]aniline

Step 1

1-methyl-4-nitro-2-[4-(3-pyridyl)pyridin-2-ylamino] benzene

This compound was prepared in the same manner as in Reference Example 22 (step 2), except that diethyl(3-pyridyl) borane was used, and that the crude product obtained by purification with silica gel column chromatography was crystallized by adding chloroform-methanol.

Orange Crystals

Melting point: 170-173° C. (with decomposition)

Step 2

4-methyl-3-[4-(3-pyridyl)pyridin-2-ylamino]aniline

To 126 mg of 1-methyl-4-nitro-2-[4-(3-pyridyl)pyridin-2-ylamino]benzene obtained in the step 1, 1 ml of concentrated hydrochloric acid was added and a solution of 465 mg of tin chloride (II) dihydrate in 1 ml of concentrated hydrochloric acid was added while stirring with heating at 60° C. The mixture was gradually heated up to 100° C. and further stirred with heating at 100° C. for 40 minutes. After the reaction solution was air-cooled, water was added and the solution was alkalified with a 10% aqueous sodium hydroxide solution. The reaction solution was subjected to extraction with ethyl acetate three times and dried over anhydrous magnesium sulfate, and then the solvent was distilled off under reduced pressure. The resulting crude crystals were washed with a small amount of chloroform and then collected by filtration to obtain 93 mg of the objective compound as pale yellow crystals.

Melting point: 183-186° C.

Reference Example 24

1-methylpiperazine-2-carboxamide dihydrochloride

Step 1

4-(t-butoxycarbonyl)-1-methylpiperazine-2-carboxamide

A solution of 6.00 g of 4-(t-butoxycarbonyl)piperazine-2-carboxamide and 3.28 g of a 37% aqueous formaldehyde solution in 60 ml of methanol was ice-cooled, and 16.66 g of sodium triacetoxyborohydride was added, followed by stirring at room temperature for 24 hours after removing an ice bath. The reaction solution was again ice-cooled, 3.28 g of a 37% aqueous formaldehyde solution and 16.66 g of sodium triacetoxyborohydride were added thereto. After stirring at room temperature for 16 hours, the reaction solution was diluted with ice water, alkalified with an aqueous saturated sodium hydrogen carbonate solution, followed by extraction with ethyl acetate three times. The organic layers were combined and dried over anhydrous magnesium sulfate, and then the solvent was distilled off under reduced pressure. The residue was purified by silica gel column chromatography to obtain 5.42 g of the objective compound as colorless crystals.

Melting point: 137-138° C.

Step 2

1-methylpiperazine-2-carboxamide dihydrochloride 5.40 g of 4-(t-butoxycarbonyl)-1-methylpiperazine-2-carboxamide obtained in the step 1 was dissolved in 29 ml of methanol, 48 ml of hydrochloric acid-methanol (Reagent 10, Tokyo Chemical Industry Co., Ltd.) was added, and the mixture was heated at reflux for 6 hours. The reaction solution was concentrated under reduced pressure and dried under reduced pressure to obtain 5.97 g of a crude product as a blue-green oily product.

Reference Example 25

3-(dimethylaminomethyl)azetidine dihydrochloride

Step 1

1-(t-butoxycarbonyl)-3-(dimethylaminomethyl)azetidine

To a solution of 920 mg of 1-(t-butoxycarbonyl)-3-(aminomethyl)azetidine in 18 ml of methanol, 5.66 ml of acetic acid, 4.12 g of a 37% aqueous formaldehyde solution and 3.14 g of sodium triacetoxyborohydride were added in turn, followed by stirring at room temperature for 20 hours. The reaction solution was alkalified by adding an aqueous saturated sodium hydrogen carbonate solution, subjected to extraction with ethyl acetate three times. The organic layers were combined, washed with water and then dried over anhydrous magnesium sulfate. Then, the solvent was distilled off under reduced pressure. The residue was purified by silica gel column chromatography to obtain 673 mg of the objective compound as a colorless oily product.

Step 2

3-(dimethylaminomethyl)azetidine dihydrochloride

This compound was prepared in the same manner as in Reference Example 24 (step 2), except that 1-(t-butoxycarbonyl)-3-(dimethylaminomethyl)azetidine obtained in the step 1 was used.

Pale Yellow Oily Product

Reference Example 26

(S)-3-(N,N-diethylamino)pyrrolidine dihydrochloride

Step 1

(S)-1-(benzyloxycarbonyl)-3-(N,N-diethylamino)pyrrolidine

To a solution of 1.40 g of (S)-3-amino-1-(benzyloxycarbonyl)pyrrolidine (J. Med. Chem., 1992, 35, 1764-1773) in 28 ml of tetrahydrofuran, 2.6 g of potassium carbonate and 1.0 ml of ethyl iodide were added under ice-cool stirring, followed by stirring for 24 hours. The reaction solution was concentrated under reduced pressure, mixed with water, followed by extraction with ethyl acetate, and dried over anhydrous magnesium sulfate, and then the solvent was distilled off under reduced pressure. The residue was purified by silica gel column chromatography to obtain 0.70 g of the objective compound as a yellow oily product.

Step 2

(S)-3-(N,N-diethylamino)pyrrolidine dichloride 700 mg of (S)-1-(benzyloxycarbonyl)-3-(N,N-diethylamino)pyrrolidine obtained in the step 1 was dissolved in 28 ml of methanol and 70 mg of 10% palladium-carbon was added, and then the mixture was hydrogenated at room temperature under 3 atm for 2 hours. The catalyst was removed by filtration and 10 ml of 10% hydrochloric acid-methanol was added to the filtrate, followed by concentrating under reduced pressure to obtain 576 mg of a crude product.

Reference Example 27

(S)-3-(1-pyrrolidinyl)pyrrolidine hydrochloride

Step 1

(S)-1-benzyl-3-(1-pyrrolidinyl)pyrrolidine 2.00 g of (R)-1-benzyl-3-(p-toluenesulfonyloxy)pyrrolidine (J. Med. Chem., 1992, 35, 4205-4208) was dissolved in 12 ml of ethanol, 1.63 g of pyrrolidine was added, and then the mixture was stirred at 140° C. for 20 hours in a sealed tube. The reaction solution was concentrated under reduced pressure, mixed with water, followed by extraction with ethyl acetate, and dried over anhydrous magnesium sulfate, and then the solvent was distilled off under reduced pressure. The residue was purified by silica gel column chromatography to obtain 0.97 g of the objective compound as a brown oily product.

Step 2

(S)-3-(1-pyrrolidinyl)pyrrolidine hydrochloride 0.97 g of (S)-1-benzyl-3-(1-pyrrolidinyl)pyrrolidine obtained in the step 1 was dissolved in 30 ml of ethanol and 4.21 ml of a 1N hydrochloric acid was added. 1.68 g of 10% palladium-carbon was added thereto and then the mixture was hydrogenated at room temperature under normal pressures overnight. The catalyst was removed by filtration and the filtrate was concentrated under reduced pressure to obtain 0.74 g of a crude product as a slightly-red oily product.

Reference Example 28

(3S,4S)-3-(dimethylamino)-4-methoxypyrrolidine dihydrochloride

Step 1

(3S,4S)-1-(t-butoxycarbonyl)-3-(dimethylamino)-4-hydroxypyrrolidine

This compound was prepared in the same manner as in Reference Example 25 (step 1), except that (3S,4S)-1-(t-butoxycarbonyl)-3-hydroxy-4-(methylamino)pyrrolidine (Tetrahedron: Asymmetry, 2001, 12, 2989-2997) was used, and that the reaction was conducted for 1 hour under ice cooling, the reaction solution was alkalified with a 1N aqueous sodium hydroxide solution and methanol was mostly distilled off under reduced pressure, followed by extraction with ethyl acetate twice.

Colorless Oily Product

Step 2

(3S,4S)-1-(t-butoxycarbonyl)-3-(dimethylamino)-4-methoxypyrrolidine

To a suspension of 448 mg of 60% sodium hydride in 5 ml of anhydrous N,N-dimethylformamide, 1.59 g of methyl iodide was added and a solution of 2.15 g of (3S,4S)-1-(t-butoxycarbonyl)-3-(dimethylamino)-4-hydroxypyrrolidine obtained in the step 1 dissolved in 10 ml of anhydrous N,N-dimethylformamide was added dropwise under ice-cool stirring, followed by stirring at room temperature for 1 hour after removing an ice bath. The reaction solution was ice-cooled and a 1% aqueous acetic acid solution was added dropwise thereto, and then the mixture was subjected to extraction with ethyl acetate twice. The organic layers were combined, washed with saturated saline and then dried over anhydrous sodium sulfate. Then, the solvent was distilled off under reduced pressure. The residue was purified by silica gel column chromatography to obtain 1.10 g of the objective compound as a colorless oily product.

Step 3

(3S,4S)-3-(dimethylamino)-4-methoxypyrrolidine dihydrochloride

This compound was prepared in the same manner as in Reference Example 24 (step 2), except that (3S,4S)-1-(t-butoxycarbonyl)-3-(dimethylamino)-4-methoxypyrrolidine obtained in the step 2 was used, and that the reaction was conducted at 80° C. for 1.5 hours.

Yellow Oily Product

Reference Example 29

(2R,4S)-4-(dimethylamino)-2-methylipyrrolidine dihydrochloride

Step 1

(2R,4R)-1-(t-butoxycarbonyl)-2-methyl-4-(p-toluenesulfonyloxy)pyrrolidine

To a solution of 1.02 g of (2R,4R)-1-(t-butoxycarbonyl)-4-hydroxy-2-methylpyrrolidine (J. Med. Chem., 1988, 31, 1598-1611) in 10 ml of anhydrous dichloromethane, 1.7 ml of triethylamine and 1.16 g of p-toluenesulfonyl chloride were added, and then the mixture was stirred at room temperature overnight. The reaction solution was mixed with water, and followed by extraction with ethyl acetate twice. The organic layers were combined, washed in turn with water, 1N hydrochloric acid and a 1N aqueous sodium hydroxide solution and dried over anhydrous sodium sulfate, and then the solvent was distilled off under reduced pressure. The residue was purified by silica gel column chromatography to obtain 1.54 g of the objective compound as a colorless oily product.

Step 2

(2R,4S)-1-(t-butoxycarbonyl)-4-(dimethylamino)-2-methylpyrrolidine

To 1.99 g of (2R,4R)-1-(t-butoxycarbonyl)-2-methyl-4-(p-toluenesulfonyloxy)pyrrolidine obtained in the step 1, 50 ml of dimethylamine (2M methanol solution) was added, and then the mixture was stirred at 140° C. overnight in a sealed tube. The reaction solution was concentrated under reduced pressure, and then the residue was purified by silica gel column chromatography to obtain 874 mg of the objective compound as a brown oily product.

Step 3

(2R,4S)-4-(dimethylamino)-2-methylpyrrolidine dihydrochloride

This compound was prepared in the same manner as in Reference Example 24 (step 2), except that (2R,4S)-1-(t-butoxycarbonyl)-4-(dimethylamino)-2-methylpyrrolidine obtained in the step 2 was used, and that the reaction was conducted at 80° C. for 2 hours.

Brown Oily Product

Reference Example 30

(S)-3-[N-(t-butoxycarbonyl)-N-methylamino]pyrrolidine

Step 1

(S)-1-benzyl-3-[N-(t-butoxycarbonyl)]-N-methylamino]pyrrolidine

0.67 g of (S)-1-benzyl-3-(methylamino)pyrrolidine (J. Med. Chem., 1992, 35, 4205-4213) was dissolved in 5 ml of dichloromethane, a solution of di-t-butyl dicarbonate in 5 ml of dichloromethane was added thereto, and the mixture was stirred at room temperature overnight. The reaction solution was concentrated under reduced pressure, and then the crude product was purified by silica gel column chromatography to obtain 0.80 g of the objective compound as a colorless oily product.

Step 2

(S)-3-[N-(t-butoxycarbonyl)-N-methylamino]pyrrolidine

0.80 g of (S)-1-benzyl-3-[N-(t-butoxycarbonyl)]-N-methylamino]pyrrolidine obtained in the step 1 was dissolved in 18 ml of ethanol, 1.10 g of 10% palladium-carbon was added, and then the mixture was hydrogenated at room temperature under normal pressures overnight. The catalyst was removed by filtration, and the filtrate was concentrated under reduced pressure to obtain 0.42 g of the objective compound as a colorless oily product.

Reference Example 31

4-(bromomethyl)-3-trifluoromethyl-N-{4-methyl-3-[4-(5-pyrimidinyl)pyrimidin-2-ylamino]phenyl}benzamide

Step 1

4-(bromomethyl)-3-trifluoromethylbenzoic acid

To 60.0 g of 4-methyl-3-trifluoromethylbenzoic acid was added 600 ml of isopropyl acetate. Under stirring at room temperature, a solution of 133.0 g of sodium bromate in 420 ml of water and a solution of 91.7 g of sodium hydrogensulfite in 180 ml of water were added in turn. The mixture was gradually heated from 30° C. up to 50° C. at intervals of 10° C. and stirred until the color of the reaction solution disappeared. The aqueous layer was separated to remove, and to the organic layer were added a solution of 133.0 g of sodium bromate in 420 ml of water and a solution of 91.7 g of sodium hydrogensulfite in 180 ml of water, and then the mixture was gradually heated up to 60° C. as above. After separation, to the organic layer were further added a solution of 133.0 g of sodium bromate in 420 ml of water and a solution of 91.7 g of sodium hydrogensulfite in 180 ml of water, and the mixture was gradually heated as above and heated to the temperature the mixture was finally refluxed. After the completion of the reaction, the reaction solution was separated, the organic layer was washed twice with a 5% aqueous sodium thiosulfate solution and twice with 15% saline, dried over anhydrous magnesium sulfate, and, then the solvent was distilled off under reduced pressure. To the residue was added 120 ml of n-heptane, the mixture was stirred, and then the crystals were collected by filtration to obtain 50.0 g of the objective compound as colorless crystals.

Melting point: 140-143° C.

Step 2

4-(bromomethyl)-3-trifluoromethyl-N-{4-methyl-3-[4-(5-pyrimidinyl)pyrimidin-2-ylamino]phenyl}benzamide

7.69 g of 4-(bromomethyl)-3-trifluoromethylbenzoic acid obtained in the step 1 was suspended in 154 ml of anhydrous dichloromethane. Under ice-cool stirring, 6.59 ml of oxalyl chloride and 0.1 ml of anhydrous N,N-dimethylformamide were added dropwise. Under ice cooling, the mixture was further stirred for 3 hours, and then the reaction solution was concentrated under reduced pressure. To the residue was added 70 ml of anhydrous 1,4-dioxane, and then 7.00 g of 4-methyl-3-[4-(5-pyrimidinyl)pyrimidin-2-ylamino]aniline (Reference Example 18) and 4.18 g of potassium carbonate were added in turn, followed by stirring at room temperature for 18 hours. To the reaction solution was added 175 ml of water, and the mixture was violently stirred for one hour. Then, the deposit was collected by filtration and washed in turn with water, a small amount of acetonitrile, ethyl acetate and diisopropyl ether to obtain 8.10 g of the objective compound as pale yellow crystals.

Melting point: 198-202° C. (with decomposition)

Reference Example 32

4-(piperazin-1-ylmethyl)-3-trifluoromethyl-N-{[4-methyl-3-[4-(5-pyrimidinyl)pyrimidin-2-ylamino]phenyl}benzamide This compound was prepared in the same manner as in Example 47, except that piperazine was used, and that piperazine was used in an amount of 10 equivalents based on the raw material.

Pale Yellow Crystals

Melting point: 208-213° C.

Reference Example 33

4-(4-methylpiperazin-1-ylmethyl)-3-trifluoromethyl-N-[4-methyl-3-(thioureido)phenyl]benzamide Step 1

4-(4-methylpiperazin-1-ylmethyl)-3-trifluoromethyl-N-(3-amino-4-methylphenyl)benzamide 1.04 g of 2,4-diaminotoluene, 104 mg of 4-(dimethylamino)pyridine and 4.9 ml of N,N-diisopropyl-N-ethylamine were dissolved in 40 ml of acetonitrile. Under ice-cool stirring, 3.70 g of 4-(4-methylpiperazin-1-ylmethyl)-3-trifluoromethylbenzoyl chloride dihydrochloride (Reference Example 2) was added by four portions. After stirring for 1 hour, the solvent was distilled off under reduced pressure and diluted with water. The reaction solution was alkalified with an aqueous saturated sodium hydrogen carbonate solution, followed by extraction with ethyl acetate twice, and dried over anhydrous magnesium sulfate. The solvent was distilled off under reduced pressure, and the residue was purified by silica gel column chromatography to obtain 2.56 g of the objective compound as a pale brown amorphous.

Step 2

4-(4-methylpiperazin-1-ylmethyl)-3-trifluoromethyl-N-[3-(3-benzoylthioureido)-4-methylphenyl]benzamide To a solution of 0.21 g of ammonium thiocyanate in 1.5 ml of acetone was added dropwise a solution of 0.35 g of benzoyl chloride in 0.5 ml of acetone, under stirring at room temperature. After the mixture was refluxed for 15 minutes, a solution of 1.00 g of 4-(4-methylpiperazin-1-ylmethyl)-3-trifluoromethyl-N-(3-amino-4-methylphenyl)benzamide obtained in the step 1 in 4 ml of acetone was added dropwise and the mixture was further heated at reflux for 15 minutes. The reaction solution was air-cooled to room temperature, and then diluted with water. The solution was subjected to extraction with ethyl acetate twice and dried over anhydrous magnesium sulfate. Then, the solvent was distilled off under reduced pressure, and the residue was purified by silica gel column chromatography to obtain 0.98 g of the objective compound as colorless crystals.

Melting point: 127-129° C.

Step 3

4-(4-methylpiperazin-1-ylmethyl)-3-trifluoromethyl-N-[4-methyl-3-(thioureido)phenyl]benzamide To a solution of 960 mg of 4-(4-methylpiperazin-1-ylmethyl)-3-trifluoromethyl-N-[3-(3-benzoylthioureido)-4-methylphenyl]benzamide obtained in the step 2 in 10 ml of methanol was added 4 ml of a 1N aqueous sodium hydroxide solution. The mixture was heated at reflux for 2 hours, and then the solvent was mostly distilled off under reduced pressure and diluted with water. The reaction solution was acidified by adding 6 ml of 1N hydrochloric acid, and then alkalified by adding 28% aqueous ammonia. The deposited crystals were collected by filtration to obtain 718 mg of the objective compound as colorless crystals.

Melting point: 215-216° C. (with decomposition)

Reference Example 34

3-(dimethylamino)azetidine dihydrochloride

Step 1

1-(t-butoxycarbonyl)-3-(dimethylamino)azetidine

This compound was prepared in the same manner as in Reference Example 25 (Step 1), except that 1-(t-butoxycarbonyl)-3-aminoazetidine was used.

Step 2

3-(dimethylamino)azetidine dihydrochloride

This compound was prepared in the same manner as in Reference Example 25 (Step 2), except that 1-(t-butoxycarbonyl)-3-(dimethylamino)azetidine obtained in the step 1 was used.

Colorless Oily Product

Reference Example 35

(S)-3-(dimethylaminomethyl)pyrrolidine dihydrochloride

Step 1

(R)-1-(t-butoxycarbonyl)-3-(dimethylaminomethyl)pyrrolidine

This compound was prepared in the same manner as in Reference Example 25 (Step 1), except that (R)-3-(aminomethyl)-1-(t-butoxycarbonyl)pyrrolidine was used.

Step 2

(S)-3-(dimethylaminomethyl)pyrrolidine dihydrochloride

This compound was prepared in the same manner as in Reference Example 25 (Step 2), except that (R)-1-(t-butoxycarbonyl)-3-(dimethylaminomethyl)pyrrolidine obtained in the step 1 was used.

Colorless Oily Product

Reference Example 36

(R)-3-(dimethylaminomethyl)pyrrolidine dihydrochloride

Step 1

(S)-1-(t-butoxycarbonyl)-3-(dimethylaminomethyl) pyrrolidine

This compound was prepared in the same manner as in Reference Example 25 (Step 1), except that (S)-3-(aminomethyl)-1-(t-butoxycarbonyl)pyrrolidine was used.

Step 2

(R)-3-(dimethylaminomethyl)pyrrolidine dihydrochloride

This compound was prepared in the same manner as in Reference Example 25 (Step 2), except that (S)-1-(t-butoxycarbonyl)-3-(dimethylaminomethyl)pyrrolidine obtained in the step 1 was used.

Pale Yellow Oily Product

Reference Example 37

(3R,4R)-3-(dimethylamino)-4-methoxyppyrrolidine dihydrochloride

This compound was prepared using (3R,4R)-1-(t-butoxycarbonyl)-3-hydroxy-4-(methylamino)pyrrolidine (Tetrahedron: Asymmetry, 2001, 12, 2989-2997) according to the method of Reference Example 28 (Step 1 to Step 3).

Colorless Oily Product

Structural formulas and properties of the following Reference Examples 38 to 81 are shown in Table 1.

Reference Example 38

3-bromo-4-(4-methylpiperazin-1-ylmethyl)-N-{4-methyl-3-[4-(3-pyridyl)pyrimidin-2-ylamino]phenyl}benzamide

Reference Example 39

3-iodo-4-(4-methylpiperazin-1-ylmethyl)-N-{4-methyl-3-[4-(3-pyridyl)pyrimidin-2-ylamino]phenyl}benzamide

Reference Example 40

3-chloro-4-(4-methylpiperazin-1-ylmethyl)-N-{4-methyl-3-[4-(3-pyridyl)pyrimidin-2-ylamino]phenyl}benzamide

Reference Example 41

3-fluoro-4-(4-methylpiperazin-1-ylmethyl)-N-{4-methyl-3-[4-(3-pyridyl)pyrimidin-2-ylamino]phenyl}benzamide

Reference Example 42

4-(4-methylpiperazin-1-ylmethyl)-3-trifluoromethyl-N-{4-methyl-3-[4-(3-pyridyl)pyrimidin-2-ylamino]phenyl}benzamide

Reference Example 43

4-(4-methylpiperazin-1-ylmethyl)-3-trifluoromethyl-N-{4-methyl-3-[4-(5-pyrimidinyl)pyrimidin-2-ylamino]phenyl}benzamide

Reference Example 44

3-bromo-4-(4-methylpiperazin-1-ylmethyl)-N-{4-methyl-3-[4-(2-pyrazinyl)pyrimidin-2-ylamino]phenyl}benzamide

Reference Example 45

3-bromo-4-(4-methylpiperazin-1-ylmethyl)-N-{3-[4-(6-chloropyridin-3-yl)pyrimidin-2-ylamino]-4-methylphenyl}benzamide

Reference Example 46

3-bromo-4-(4-methylpiperazin-1-ylmethyl)-N-{3-[4-(5-bromopyridin-3-yl)pyrimidin-2-ylamino]-4-methylphenyl}benzamide

Reference Example 47

4-(4-methylpiperazin-1-ylmethyl)-3-trifluoromethyl-N-{3-[4-(5-bromopyridin-3-yl)pyrimidin-2-ylamino]-4-methylphenyl}benzamide

Reference Example 48

3-bromo-4-(4-methylpiperazin-1-ylmethyl)-N-{3-[4-(1,2-dihydropyridazin-4-yl)pyrimidin-2-ylamino]-4-methylphenyl}benzamide

Reference Example 49

3-bromo-4-(4-methylpiperazin-1-ylmethyl)-N-{4-methyl-3-[4-(3-pyridazinyl)pyrimidin-2-ylamino]phenyl}benzamide

Reference Example 50

3-bromo-4-(4-methylpiperazin-1-ylmethyl)-N-{4-methyl-3-[4-(5-pyrimidinyl)pyrimidin-2-ylamino]phenyl}benzamide

Reference Example 51

3-bromo-4-(4-methylpiperazin-1-ylmethyl)-N-{4-methyl-3-[4-(3-pyridyl)pyridin-2-ylamino]phenyl}benzamide

Reference Example 52

3-bromo-4-(4-methylpiperazin-1-ylmethyl)-N-{4-methyl-3-[4-(5-pyrimidinyl)pyridin-2-ylamino]phenyl}benzamide

Reference Example 53

3-bromo-4-(4-methylpiperazin-1-ylmethyl)-N-{4-methyl-3-[2-(3-pyridyl)pyridin-6-ylamino]phenyl}benzamide

Reference Example 54

3-bromo-4-(4-methylpiperazin-1-ylmethyl)-N-{4-methyl-3-[3-(3-pyridyl)pyridin-5-ylamino]phenyl}benzamide

Reference Example 55

3-bromo-4-(4-methylpiperazin-1-ylmethyl)-N-{4-methyl-3-[3-(3-pyridyl)phenylamino]phenyl}benzamide

Reference Example 56

3-bromo-4-(4-methylpiperazin-1-ylmethyl)-N-{4-methyl-3-[2-(3-pyridyl)pyrazin-6-ylamino]phenyl}benzamide

Reference Example 57

3-bromo-4-(4-methylpiperazin-1-ylmethyl)-N-{4-methyl-3-[5-(3-pyridyl)-1,2,4-triazin-3-ylamino]phenyl}benzamide

Reference Example 58

3-methyl-4-(4-methylpiperazin-1-ylmethyl)-N-{4-methyl-3-[4-(3-pyridyl)pyrimidin-2-ylamino]phenyl}benzamide

Reference Example 59

4-(4-methylpiperazin-1-ylmethyl)-3-nitro-N-{4-methyl-3-[4-(3-pyridyl)pyrimidin-2-ylamino]phenyl}benzamide

Reference Example 60

3-methoxy-4-(4-methylpiperazin-1-ylmethyl)-N-{4-methyl-3-[4-(3-pyridyl)pyrimidin-2-ylamino]phenyl}benzamide

Reference Example 61

3,5-dibromo-4-(4-methylpiperazin-1-ylmethyl)-N-{4-methyl-3-[4-(3-pyridyl)pyrimidin-2-ylamino]phenyl}benzamide

Reference Example 62

3,5-dimethoxy-4-(4-methylpiperazin-1-ylmethyl)-N-{4-methyl-3-[4-(3-pyridyl)pyrimidin-2-ylamino]phenyl}benzamide

Reference Example 63

3-(N,N-dimethylcarbamoyl)-4-(4-methylpiperazin-1-ylmethyl)-N-{4-methyl-3-[4-(3-pyridyl)pyrimidin-2-ylamino]phenyl}benzamide

Reference Example 64

3-bromo-4-(4-ethylpiperazin-1-ylmethyl)-N-{4-methyl-3-[4-(3-pyridyl)pyrimidin-2-ylamino]phenyl}benzamide

Reference Example 65

3-bromo-4-[4-(n-propyl)piperazin-1-ylmethyl]-N-{4-methyl-3-[4-(3-pyridyl)pyrimidin-2-ylamino]phenyl}benzamide

Reference Example 66

3-bromo-4-(N,N-dimethylaminomethyl)-N-{4-methyl-3-[4-(3-pyridyl)pyrimidin-2-ylamino]phenyl}benzamide

Reference Example 67

3-bromo-4-(N,N-diethylaminomethyl)-N-{4-methyl-3-[4-(3-pyridyl)pyrimidin-2-ylamino]phenyl}benzamide

Reference Example 68

3-bromo-4-(1-pyrrolidinylmethyl)-N-{4-methyl-3-[4-(3-pyridyl)pyrimidin-2-ylamino]phenyl}benzamide

Reference Example 69

3-bromo-4-(piperidinomethyl)-N-{4-methyl-3-[4-(3-pyridyl)pyrimidin-2-ylamino]phenyl}benzamide

Reference Example 70

3-bromo-4-(morpholinomethyl)-N-{4-methyl-3-[4-(3-pyridyl)pyrimidin-2-ylamino]phenyl}benzamide

Reference Example 71

3-bromo-4-(cis-3,5-dimethylpiperazin-1-ylmethyl)-N-{4-methyl-3-[4-(3-pyridyl)pyrimidin-2-ylamino]phenyl}benzamide

Reference Example 72

3-bromo-4-(4-methyl-hexahydro-1H-1,4-diazepin-1-ylmethyl)-N-{4-methyl-3-[4-(3-pyridyl)pyrimidin-2-ylamino]phenyl}benzamide

Reference Example 73

3-bromo-4-(1-piperazinylmethyl)-N-{4-methyl-3-[4-(5-pyrimidinyl)pyrimidin-2-ylamino]phenyl}benzamide

Reference Example 74

4-[4-(t-butoxycarbonyl)piperazin-1-ylmethyl]-3-trifluoromethyl-N-{4-methyl-3-[4-(5-pyrimidinyl)pyrimidin-2-ylamino]phenyl}benzamide

Reference Example 75

4-(1-piperazinylmethyl)-3-trifluoromethyl-N-{4-methyl-3-[4-(5-pyrimidinyl)pyrimidin-2-ylamino]phenyl}benzamide

Reference Example 76

3-methoxycarbonyl-4-(4-methylpiperazin-1-ylmethyl)-N-{4-methyl-3-[4-(3-pyridyl)pyrimidin-2-ylamino]phenyl}benzamide

Reference Example 77

3-cyano-4-(4-methylpiperazin-1-ylmethyl)-N-{4-methyl-3-[4-(3-pyridyl)pyrimidin-2-ylamino]phenyl}benzamide

Reference Example 78

3-bromo-4-(4-methylpiperazin-1-ylmethyl)-N-{4-methyl-3-[4-(5-pyrimidinyl)pyrimidin-2-ylamino]phenyl}benzamide hydrochloride

Reference Example 79

4-(4-methylpiperazin-1-ylmethyl)-3-trifluoromethyl-N-{4-methyl-3-[4-(5-pyrimidinyl)pyrimidin-2-ylamino]phenyl}benzamide hydrochloride

Reference Example 80

4-(4-methylpiperazin-1-ylmethyl)-3-trifluoromethyl-N-{3-[4-(5-bromopyridin-3-yl)pyrimidin-2-ylamino]-4-methylphenyl}benzamide hydrochloride

Reference Example 81

4-(4-methylpiperazin-1-ylmethyl)-3-trifluoromethyl-N-{4-methyl-3-[4-(5-pyrimidinyl)pyrimidin-2-ylamino]phenyl}benzamide methanesulfonate

TABLE 1

| Reference Example | Structure Formula | Melting point / Molecular formula / Elemental analysis / Thero. (%) / Found (%) |
|---|---|---|
| 38 | | 202-203° C.<br>$C_{29}H_{30}BrN_3O \cdot 0.9H_2O$<br>C:59.17, H:5.44, N:16.65<br>C:59.16, H:5.21, N:16.64 |
| 39 | | 199-200° C.<br>$C_{29}H_{30}IN_3O$<br>C:56.23, H:4.88, N:15.83<br>C:56.13, H:4.94, N:15.80 |
| 40 | | 193-194° C.<br>$C_{29}H_{30}ClN_3O \cdot 0.6H_2O$<br>C:64.64, H:5.84, N:18.20<br>C:64.62, H:5.60, N:18.23 |

TABLE 1-continued

| Reference Example | Structure Formula | Melting point Molecular formula Elemental analysis Thero. (%) Found (%) |
|---|---|---|
| 41 | | 197-199° C. $C_{29}H_{30}FN_3O\cdot0.3H_2O$ C:67.37, H:5.97, N:18.96 C:67.36, H:5.96, N:18.93 |
| 42 | | 182-183° C. $C_{30}H_{30}F_3N_3O\cdot0.3H_2O$ C:63.55, H:5.44, N:17.29 C:63.43, H:5.37, N:17.29 |
| 43 | | 231-233° C. $C_{28}H_{29}F_3N_3O\cdot0.2H_2O$ C:61.52, H:5.23, N:19.79 C:61.37, H:5.24, N:19.81 |
| 44 | | 213-214° C. $C_{28}H_{29}BrN_3O$ C:58.64, H:5.10, N:19.54 C:58.41, H:5.11, N:19.24 |
| 45 | | 219-220° C. $C_{28}H_{29}BrClN_3O$ C:57.39, H:4.82, N:16.15 C:57.07, H:4.75, N:16.09 |

TABLE 1-continued

| Reference Example | Structure Formula | Melting point / Molecular formula / Elemental analysis / Thero. (%) / Found (%) |
|---|---|---|
| 46 | | 194-195° C.<br>C$_{28}$H$_{29}$Br$_2$N$_2$O·0.3H$_2$O<br>C:53.03, H:4.54, N:14.93<br>C:53.07, H:4.53, N:14.70 |
| 47 | | 171-173° C.<br>C$_{30}$H$_{29}$BrF$_3$N$_2$O·0.7H$_2$O<br>C:55.17, H:4.69, N:15.01<br>C:55.16, H:4.57, N:14.94 |
| 48 | | amorphous<br>C$_{30}$H$_{31}$BrN$_2$O·0.81PE<br>C:59.94, H:6.47, N:17.06<br>C:59.94, H:6.30, N:16.80 |
| 49 | | 185-187° C.<br>C$_{28}$H$_{29}$BrN$_3$O·0.1H$_2$O<br>C:58.28, H:5.13, N:19.42<br>C:58.24, H:5.00, N:19.48 |
| 50 | | 238-240° C.<br>C$_{28}$H$_{29}$BrN$_3$O·0.1H$_2$O<br>C:58.46, H:6.12, N:19.48<br>C:58.21, H:5.02, N:19.30 |

TABLE 1-continued

| Reference Example | Structure Formula | Melting point<br>Molecular formula<br>Elemental analysis<br>Thero. (%)<br>Found (%) |
|---|---|---|
| 51 | | 244-245° C. (dec.)<br>$C_{32}H_{31}BrN_3O\cdot 0.6H_2O$<br>C:51.88, H:5.57, N:14.43<br>C:51.71, H:5.49, N:14.13 |
| 52 | | 244-246° C. (dec.)<br>$C_{29}H_{30}BrN_2O\cdot 0.2AcOEt\cdot 0.2H_2O$<br>C:60.28, H:5.43, N:16.51<br>C:60.12, H:5.40, N:16.28 |
| 53 | | amorphous<br>$C_{30}H_{31}BrN_3O$<br>C:63.05, H:5.47, N:14.70<br>(合致せず) |
| 54 | | 139-141° C.<br>$C_{30}H_{31}BrN_3O\cdot 1.2H_2O$<br>C:60.75, H:5.68, N:14.17<br>C:60.90, H:5.62, N:13.98 |
| 55 | | 174-175° C.<br>$C_{21}H_{22}BrN_3O$<br>C:65.26, H:5.65, N:12.28<br>C:65.12, H:5.73, N:12.19 |

TABLE 1-continued

| Reference Example | Structure Formula | Melting point Molecular formula Elemental analysis Thero. (%) Found (%) |
|---|---|---|
| 56 | (structure) | 192-193° C. $C_{29}H_{30}BrN_2O \cdot 0.25H_2O$ C:60.37, H:5.33, N:16.99 C:60.58, H:5.35, N:16.76 |
| 57 | (structure) | 158-159° C. $C_{28}H_{29}BrN_3O$ $+0.1C_3H_2O, +1.2H_2O$ C:56.55, H:5.40, N:18.64 C:56.58, H:5.40, N:18.27 |
| 58 | (structure) | 192-193° C. $C_{30}H_{33}N_3O$ C:70.98, H:6.55, N:19.31 C:70.79, H:6.57, N:19.39 |
| 59 | (structure) | 184-188° C. $C_{29}H_{30}N_3O_3 \cdot 0.3H2O$ C:63.19, H:5.74, N:20.33 C:63.38, H:5.57, N:20.00 |
| 60 | (structure) | 171-172° C. $C_{22}H_{23}N_3O_2 \cdot 0.6H_2O$ C:67.42, H:6.45, N:18.35 C:67.23, H:6.36, N:18.19 |

TABLE 1-continued

| Reference Example | Structure Formula | Melting point Molecular formula Elemental analysis Thero. (%) Found (%) |
|---|---|---|
| 61 | | 227-229° C. $C_{27}H_{28}Br_2N_3O \cdot 0.35AcOEt \cdot 0.1H_2O$ C:53.38, H:4.72, N:14.33 C:53.02, H:4.74, N:14.09 |
| 62 | | 201-214° C. (dec.) $C_{34}H_{35}N_3O_3 \cdot 0.5H_2O$ C:66.17, H:6.45, N:17.43 C:65.91, H:6.42, N:17.42 |
| 63 | | 210-214° C. (dec.) $C_{32}H_{33}N_3O_2 \cdot 0.6H_2O$ C:68.79, H:6.52, N:19.47 C:66.41, H:6.17, N:19.36 |
| 64 | | 202-203° C. $C_{30}H_{31}BrN_3O \cdot 0.25H_2O$ C:60.97, H:5.54, N:16.59 C:60.96, H:5.54, N:16.32 |
| 65 | | 204-205° C. $C_{31}H_{32}BrN_3O \cdot 0.4H_2O$ C:61.26, H:5.77, N:16.13 C:61.48, H:5.66, N:15.79 |

TABLE 1-continued

| Reference Example | Structure Formula | Melting point<br>Molecular formula<br>Elemental analysis<br>Thero. (%)<br>Found (%) |
|---|---|---|
| 66 | (structure) | 154-155° C.<br>$C_{24}H_{25}BrN_3O$<br>C:60.35, H:4.87, N:16.24<br>C:60.20, H:4.97, N:16.13 |
| 67 | (structure) | 172-173° C.<br>$C_{28}H_{29}BrN_3O$<br>C:61.65, H:5.35, N:15.41<br>C:61.35, H:5.36, N:15.35 |
| 68 | (structure) | 195-196° C.<br>$C_{26}H_{27}BrN_3O$<br>C:61.88, H:5.01, N:15.40<br>C:61.68, H:5.12, N:15.11 |
| 69 | (structure) | 158-159° C.<br>$C_{26}H_{27}BrN_3O$<br>C:62.48, H:5.24, N:15.07<br>C:62.23, H:5.25, N:14.83 |
| 70 | (structure) | 179-180° C.<br>$C_{26}H_{27}BrN_3O_2$<br>C:60.11, H:4.86, N:15.02<br>C:59.94, H:4.93, N:14.96 |

TABLE 1-continued

| Reference Example | Structure Formula | Melting point<br>Molecular formula<br>Elemental analysis<br>Thero. (%)<br>Found (%) |
|---|---|---|
| 71 | | 204-205° C.<br>$C_{20}H_{21}BrN_3O$<br>C:61.43, H:5.50, N:16.72<br>C:61.19, H:5.48, N:16.49 |
| 72 | | 156-157° C.<br>$C_{30}H_{32}BrN_3O\cdot0.25H_2O$<br>C:61.43, H:5.50, N:16.72<br>C:61.13, H:5.43, N:16.39 |
| 73 | | 225-228° C.<br>$C_{27}H_{28}BrN_3O\cdot0.3H_2O$<br>C:57.41, H:4.92, N:19.84<br>C:57.48, H:5.07, N:18.84 |
| 74 | | 188-191° C.<br>$C_{23}H_{24}F_3N_2O_3$<br>NMR |
| 75 | | 203-211° C.<br>$C_{26}H_{27}F_3N_3O$<br>C:61.31, H:4.96, N:20.43<br>C:61.03, H:5.01, N:20.33 |

TABLE 1-continued
| Reference Example | Structure Formula | Melting point<br>Molecular formula<br>Elemental analysis<br>Thero. (%)<br>Found (%) |
|---|---|---|
| 76 | 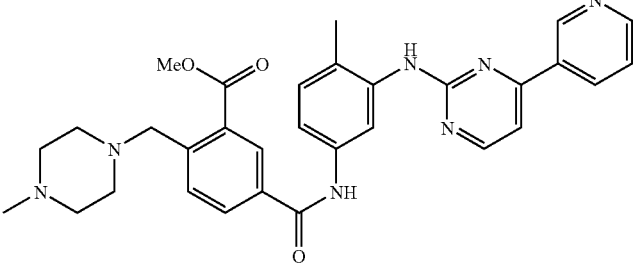 | 159-161° C.<br>$C_{31}H_{32}N_3O_3 \cdot 0.2H_2O$<br>C:67.06, H:6.06, N:17.66<br>C:56.77, H:6.03, N:17.68 |
| 77 | 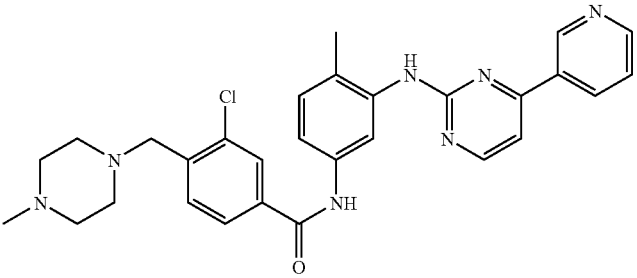 | 191-193° C. (dec.)<br>$C_{30}H_{30}N_3O \cdot 0.5H_2O$<br>C:68.29, H:5.92, N:21.24<br>C:68.05, H:5.99, N:21.12 |
| 78 | 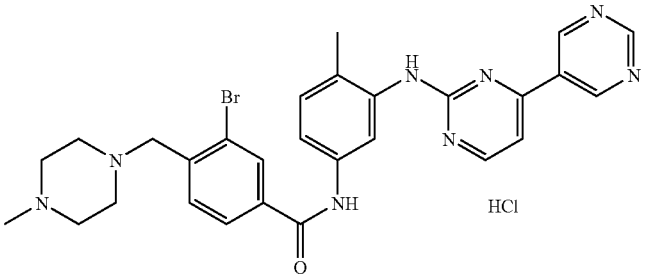 | 184-186° C.<br>$C_{23}H_{24}BrN_3O—HCl \cdot 2H_2O$<br>C:52.06, H:5.31, N:17.35<br>C:51.72, H:5.17, N:17.21 |
| 79 | 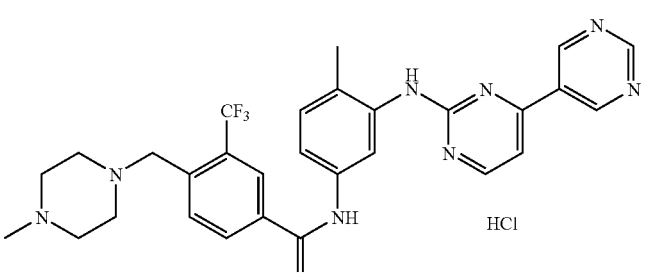 | 244-246° C. (dec.)<br>$C_{26}H_{27}F_3N_3O—HCl \cdot 0.8H_2O$<br>C:56.78, H:5.19, N:18.27<br>C:56.80, H:4.96, N:18.49 |
| 80 | 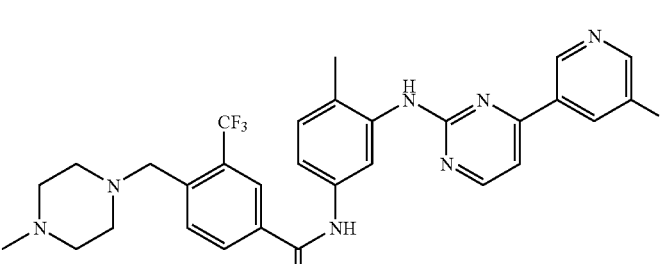 | 184-187° C.<br>$C_{26}H_{27}BrF_3N_3O—HCl—H_2O$<br>C:51.85, H:4.64, N:14.11<br>C:51.78, H:4.74, N:13.92 |

TABLE 1-continued

| Reference Example | Structure Formula | Melting point<br>Molecular formula<br>Elemental analysis<br>Thero. (%)<br>Found (%) |
|---|---|---|
| 81 | (structure shown with CF₃, methylpiperazine, methylphenyl, pyrimidinyl-pyrimidine, benzamide, CH₃SO₃H) | 171-173° C.<br>C₂₆H₂₇F₃N₃O—CH₃SO₂H—H₂O<br>C:53.25, H:5.21, N:16.56<br>C:53.04, H:5.39, N:16.74 |

The compounds of Reference Examples 38 to 81 were prepared according to the preparation process 1 as described above.

Reference Example 82

4-(bromomethyl)-3-trifluoromethyl-N-{4-methyl-3-[4-(3-pyridyl)pyrimidin-2-ylamino]phenyl}benzamide In the same manner as in Reference Example 31, the objective compound is prepared using 4-methyl-3-[4-(3-pyridyl)pyrimidin-2-ylamino]aniline (Patent Document 1).

Example 1

3-difluoromethyl-4-(4-methylpiperazin-1-ylmethyl)-N-{4-methyl-3-[4-(5-pyrimidinyl)pyrimidin-2-ylamino]phenyl}benzamide 1.98 g of 4-methyl-3-[4-(5-pyrimidinyl)pyrimidin-2-ylamino]aniline (Reference Example 18) was dissolved in 35 ml of anhydrous pyridine and 2.90 g of 3-difluoromethyl-4-(4-methylpiperazin-1-ylmethyl)benzoyl chloride hydrochloride (Reference Example 9) was added, followed by stirring at room temperature for 2 hours. To the reaction solution, ice water and an aqueous saturated sodium hydrogen carbonate solution were added and then the mixture was subjected to extraction with ethyl acetate. The extract was washed with water and dried over anhydrous magnesium sulfate, and then the solvent was distilled off under reduced pressure. The crude crystals were washed with chloroform-diethyl ether (1:1) to obtain 2.66 g of the objective compound as pale brown crystals.
Melting point: 206-207° C.

Example 2

3-difluoromethyl-4-(4-methylpiperazin-1-ylmethyl)-N-{4-methyl-3-[4-(5-pyrimidinyl)pyrimidin-2-ylamino]phenyl}benzamide hydrochloride 2.66 g of 3-difluoromethyl-4-(4-methylpiperazin-1-ylmethyl)-N-{4-methyl-3-[4-(5-pyrimidinyl)pyrimidin-2-ylamino]phenyl}benzamide (Example 1) was suspended in 26 ml of ethanol and 4.88 ml of 1 N hydrochloric acid was added thereto, and then the mixture was stirred with heating in a hot bath at 70° C. and dissolved. The solvent was distilled off under reduced pressure, and then the crude crystals were washed with ethanol to obtain 2.80 g of the objective compound.

Ocherous Crystals
  Melting point: 264° C. (with decomposition)
  Elemental analysis (for $C_{29}H_{30}F_2N_8O \cdot HCl0.6EtOH$)
  Calcd. (%): C, 59.59; H, 5.73; N, 18.41.
  Found (%): C, 59.59; H, 5.71; N, 18.53.

Example 3

3-ethyl-4-(4-methylpiperazin-1-ylmethyl)-N-{4-methyl-3-[4-(5-pyrimidinyl)pyrimidin-2-ylamino]phenyl}benzamide This compound was prepared in the same manner as in Example 1, except that 3-ethyl-4-(4-methylpiperazin-1-ylmethyl)benzoyl chloride hydrochloride (Reference Example 1) was used, and that the reaction was conducted at room temperature for 2 days and the crude product was purified by silica gel column chromatography.

Yellow Crystals
  Melting point: 131-134° C.

Example 4

3-ethyl-4-(4-methylpiperazin-1-ylmethyl)-N-{4-methyl-3-[4-(5-pyrimidinyl)pyrimidin-2-ylamino]phenyl}benzamide hydrochloride This compound was prepared in the same manner as in Example 2, except that 3-ethyl-4-(4-methylpiperazin-1-ylmethyl)-N-{4-methyl-3-[4-(5-pyrimidinyl)pyrimidin-2-ylamino]phenyl}benzamide (Example 3) was used, and that the resulting crude crystals were washed with ethyl acetate.

Yellow Crystals
  Melting point: 253-255° C. (with decomposition)
  Elemental analysis (for $C_{30}H_{34}N_8O \cdot HCl \cdot 2.1H_2O$)
  Calcd. (%): C, 60.36; H, 6.62; N, 18.77.
  Found (%): C, 60.10; H, 6.31; N, 18.75.

Example 5

4-(1-methylpiperidin-4-ylidenemethyl)-3-trifluoromethyl-N-{4-methyl-3-[4-(5-pyrimidinyl)pyrimidin-2-ylamino]phenyl}benzamide This compound was prepared in the same manner as in Example 1, except that a suspension of 4-(1-methylpiperidin-4-ylidenemethyl)-3-trifluoromethylbenzoyl chloride hydrochloride (Reference Example 7) in anhydrous tetrahydrofuran was used, and that the reaction was conducted at room temperature for 21 hours.

Yellow Crystals
    Melting point: 234-239° C. (with decomposition)

Example 6

4-(1-methylpiperidin-4-ylidenemethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-(1-methylpiperidin-4-ylidenemethyl)-3-trifluoromethyl-N-{4-methyl-3-[4-(5-pyrimidinyl)pyrimidin-2-ylamino]phenyl}benzamide (Example 5) was used, and that the resulting crude crystals were washed in turn with ethanol and diethyl ether.

Pale Yellow Crystals
    Melting point: 202-206° C. (with decomposition)
    Elemental analysis (for $C_{30}H_{28}F_3N_7O \cdot HCl \cdot H_2O$)
    Calcd. (%): C, 58.68; H, 5.09; N, 15.97.
    Found (%): C, 58.42; H, 4.92; N, 16.10.

Example 7

4-(1-methylpiperidin-4-ylmethyl)-3-trifluoromethyl-N-{4-methyl-3-[4-(5-pyrimidinyl)pyrimidin-2-ylamino]phenyl}benzamide This compound was prepared in the same manner as in Example 1, except that a suspension of 4-(1-methylpiperidin-4-ylmethyl)-3-trifluoromethylbenzoyl chloride hydrochloride (Reference Example 8) in anhydrous tetrahydrofuran was used, and that the reaction was conducted at room temperature for 21 hours and the resulting crude crystals were washed with ethyl acetate.

Pale Yellow Crystals
    Melting point: 230-233° C. (with decomposition)

Example 8

4-(1-methylpiperidin-4-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-(1-methylpiperidin-4-ylmethyl)-3-trifluoromethyl-N-{4-methyl-3-[4-(5-pyrimidinyl)pyrimidin-2-ylamino]phenyl}benzamide (Example 7) was used, and that the resulting crude crystals were washed in turn with ethanol and diethyl ether.

Pale Yellow Crystals
    Melting point: 227-231° C. (with decomposition)
    Elemental analysis (for $C_{30}H_{30}F_3N_7O \cdot HCl \cdot 0.5H_2O$)
    Calcd. (%): C, 59.35; H, 5.31; N, 16.15.
    Found (%): C, 59.02; H, 5.20; N, 16.08.

Example 9

4-(1-methylpiperidin-4-yloxy)-3-trifluoromethyl-N-{4-methyl-3-[4-(5-pyrimidinyl)pyrimidin-2-ylamino]phenyl}benzamide This compound was prepared in the same manner as in Example 1, except that 4-(1-methylpiperidin-4-yloxy)-3-trifluoromethylbenzoyl chloride hydrochloride (Reference Example 11) was used, and that the reaction was conducted at room temperature overnight and the crude product was purified by silica gel column chromatography.

Pale Yellow Crystals
    Melting point: 187-191° C.

Example 10

4-(1-methylpiperidin-4-yloxy)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-(1-methylpiperidin-4-yloxy)-3-trifluoromethyl-N-{4-methyl-3-[4-(5-pyrimidinyl)pyrimidin-2-ylamino]phenyl}benzamide (Example 9) was used, and that the resulting amorphous was crystallized by adding ethanol-diisopropyl ether.

Yellow Crystals
    Melting point: 275° C. or more
    Elemental analysis (for $C_{29}H_{28}F_3N_7O_2 \cdot HCl \cdot 0.3H_2O$)
    Calcd. (%): C, 57.53; H, 4.93; N, 16.19.
    Found (%): C, 57.34; H, 4.99; N, 16.05

Example 11

3,5-dichloro-4-[(S)-3-(dimethylamino)pyrrolidin-1-ylmethyl]-N-{4-methyl-3-[4-(5-pyrimidinyl)pyrimidin-2-ylamino]phenyl}benzamide This compound was prepared in the same manner as in Example 1, except that 3,5-dichloro-4-[(S)-3-(dimethylamino)pyrrolidin-1-ylmethyl]benzoyl chloride hydrochloride (Reference Example 6) was used, and that the reaction was conducted at room temperature for 66 hours, the crude product was purified by silica gel column chromatography and the resulting crude crystals were washed with ethyl acetate.

Yellow Crystals
    Melting point: 215-223° C. (with decomposition)

Example 12

(−)-3,5-dichloro-4-[(S)-3-(dimethylamino)pyrrolidin-1-ylmethyl]-N-{4-methyl-3-[4-(5-pyrimidinyl)pyrimidin-2-ylamino]phenyl}benzamide hydrochloride This compound was prepared in the same manner as in Example 2, except that 3,5-dichloro-4-[(S)-3-(dimethylamino)pyrrolidin-1-ylmethyl]-N-{4-methyl-3-[4-(5-pyrimidinyl)pyrimidin-2-ylamino]phenyl}benzamide (Example 11) was used, and that the resulting amorphous was crystallized by adding ethyl acetate-ethanol.

Ocherous Crystals
Melting point: 161-170° C. (with decomposition)
$[\alpha]_D^{20}$: −10.03° (c=0.538, methanol)
Elemental analysis (for $C_{29}H_{30}Cl_2N_8O.HCl.0.06CH_3CO_2C_2H_5.1.7H_2O$)
Calcd. (%): C, 54.04; H, 5.09; N, 17.24.
Found (%): C, 54.41; H, 5.56; N, 16.94.

Example 13

3-methoxy-4-(4-methylpiperazin-1-ylmethyl)-N-{3-[4-(5-bromopyridin-3-yl)pyrimidin-2-ylamino]-4-methylphenyl}benzamide This compound was prepared in the same manner as in Example 1, except that 3-[4-(5-bromopyridin-3-yl)pyrimidin-2-ylamino]-4-methylaniline (Reference Example 19) and 3-methoxy-4-(4-methylpiperazin-1-ylmethyl)benzoyl chloride dihydrochloride (Reference Example 3) were used, and that the reaction was conducted at room temperature for 17 hours and the crude product was purified by silica gel column chromatography.

Pale Yellow Crystals
Melting point: 168-171° C.

Example 14

3-methoxy-4-(4-methylpiperazin-1-ylmethyl)-N-{3-[4-(5-bromopyridin-3-yl)pyrimidin-2-ylamino]-4-methylphenyl}benzamide hydrochloride This compound was prepared in the same manner as in Example 2, except that 3-methoxy-4-(4-methylpiperazin-1-ylmethyl)-N-{3-[4-(5-bromopyridin-3-yl)pyrimidin-2-ylamino]-4-methylphenyl}benzamide (Example 13) was used, and that the resulting amorphous was crystallized by adding ethyl acetate.

Pale Yellow Crystals
Melting point: 168-169° C. (with decomposition)
Elemental analysis (for $C_{30}H_{32}BrN_7O_2.HCl.0.3CH_3CO_2C_2H_5.0.6H_2O$)
Calcd. (%): C, 55.42; H, 5.46; N, 14.50.
Found (%): C, 55.42; H, 5.45; N, 14.11.

Example 15

4-(4-ethylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 1, except that 4-(4-ethylpiperazin-1-ylmethyl)-3-trifluoromethylbenzoyl chloride dihydrochloride (Reference Example 5) was used, and that the reaction was conducted at room temperature for 20 hours and the crude product was washed with warmed methanol and then with diethyl ether.

Pale Yellow Crystals
Melting point: 240-244° C. (with decomposition)

Example 16

4-(4-ethylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-(4-ethylpiperazin-1-ylmethyl)-3-trifluoromethyl-N-{4-methyl-3-[4-(5-pyrimidinyl)pyrimidin-2-ylamino]phenyl}benzamide (Example 15) was used.

Pale Yellow Crystals
Melting point: 256-259° C. (with decomposition)
Elemental analysis (for $C_{30}H_{31}F_3N_8O.HCl$)
Calcd. (%): C, 58.77; H, 5.26; N, 18.28.
Found (%): C, 59.47; H, 5.32; N, 18.19.

Example 17

4-(4-ethylpiperazin-1-ylmethyl)-3-trifluoromethyl-N-{3-[4-(5-bromopyridin-3-yl)pyrimidin-2-ylamino]-4-methylphenyl}benzamide This compound was prepared in the same manner as in Example 1, except that 3-[4-(5-bromopyridin-3-yl)pyrimidin-2-ylamino]-4-methylaniline (Reference Example 19) and 4-(4-ethylpiperazin-1-ylmethyl)-3-trifluoromethylbenzoyl chloride dihydrochloride (Reference Example 5) were used, and that the reaction was conducted at room temperature for 24 hours and the amorphous obtained by purification with silica gel column chromatography was crystallized by adding chloroform-diethyl ether (1:1).

Pale Yellow Crystals
Melting point: 178-179° C.

Example 18

4-(4-ethylpiperazin-1-ylmethyl)-3-trifluoromethyl-N-{3-[4-(5-bromopyridin-3-yl)pyrimidin-2-ylamino]-4-methylphenyl}benzamide hydrochloride This compound was prepared in the same manner as in Example 2, except that 4-(4-ethylpiperazin-1-ylmethyl)-3-trifluoromethyl-N-{3-[4-(5-bromopyridin-3-yl)pyrimidin-2-ylamino]-4-methylphenyl}benzamide (Example 17) was used, and that the resulting amorphous was crystallized from ethanol.

Pale Yellow Crystals
Melting point: 166-172° C. (with decomposition)
Elemental analysis (for $C_{31}H_{31}BrF_3N_7O.HCl.0.5H_2O$)
Calcd. (%): C, 53.19; H, 4.75; N, 14.01.
Found (%): C, 52.89; H, 4.79; N, 14.05.

Example 19

3-chloro-4-(4-methylpiperazin-1-ylmethyl)-N-{4-methyl-3-[4-(5-pyrimidinyl)pyrimidin-2-ylamino]phenyl}benzamide This compound was prepared in the same manner as in Example 1, except that 3-chloro-4-(4-methylpiperazin-1-ylmethyl)benzoyl chloride dihydrochloride (Reference Example 4) was used, and that the reaction was conducted at room temperature for 18 hours.

Pale Yellow Crystals
Melting point: 210-227° C. (with decomposition)

Example 20

3-chloro-4-(4-methylpiperazin-1-ylmethyl)-N-{4-methyl-3-[4-(5-pyrimidinyl)pyrimidin-2-ylamino]phenyl}benzamide hydrochloride This compound was prepared in the same manner as in Example 2, except that 3-chloro-4-(4-methylpiperazin-1-ylmethyl)-N-{4-methyl-3-[4-(5-pyrimidinyl)pyrimidin-2-ylamino]phenyl}benzamide (Example 19) was used, and that the resulting amorphous was crystallized from ethanol.

Pale Yellow Crystals
Melting point: 197-200° C.
Elemental analysis (for $C_{28}H_{29}ClN_8O.HCl$)
Calcd. (%): C, 59.47; H, 5.35; N, 19.81.
Found (%): C, 59.73; H, 5.38; N, 19.90

Example 21

3-fluoromethyl-4-(1-methylpiperidin-4-ylmethyl)-N-{4-methyl-3-[4-(5-pyrimidinyl)pyrimidin-2-ylamino]phenyl}benzamide This compound was prepared in the same manner as in Example 1, except that 3-fluoromethyl-4-(1-methylpiperidin-4-ylmethyl)benzoyl chloride hydrochloride (Reference Example 10) was used, and that the reaction was conducted at room temperature for 3 days and the amorphous obtained by purification with silica gel column chromatography was crystallized from ethyl acetate.

Pale Yellow Crystals
Melting point: 162-164° C.

Example 22

4-(4-methylpiperazin-1-ylmethyl)-3-trifluoromethyl-N-{4-methyl-3-[4-(5-pyrimidinyl)pyridin-2-ylamino]phenyl}benzamide This compound was prepared in the same manner as in Example 1, except that 4-methyl-3-[4-(5-pyrimidinyl)pyridin-2-ylamino]aniline (Reference Example 22) and 4-(4-methylpiperazin-1-ylmethyl)-3-trifluoromethylbenzoyl chloride dihydrochloride (Reference Example 2) were used, and that the resulting crude crystals were washed with ethyl acetate.

Pale Yellow Crystals
Melting point: 277° C. (with decomposition)

Example 23

4-(4-methylpiperazin-1-ylmethyl)-3-trifluoromethyl-N-{4-methyl-3-[4-(5-primidinyl)pyridin-2-ylamino]phenyl}benzamide hydrochloride This compound was prepared in the same manner as in Example 2, except that 4-(4-methylpiperazin-1-ylmethyl)-3-trifluoromethyl-N-{4-methyl-3-[4-(5-pyrimidinyl)pyridin-2-ylamino]phenyl}benzamide (Example 22) was used.

Colorless Crystals
Melting point: 203-206° C. (with decomposition)
Elemental analysis (for $C_{30}H_{30}F_3N_7O.HCl.0.3H_2O$)
Calcd. (%): C, 59.71; H, 5.28; N, 16.25.
Found (%): C, 59.52; H, 5.34; N, 16.37.

Example 24

4-(4-ethylpiperazin-1-ylmethyl)-3-trifluoromethyl-N-{4-methyl-3-[4-(5-pyrimidinyl)pyridin-2-ylamino]phenyl}benzamide This compound was prepared in the same manner as in Example 1, except that 4-methyl-3-[4-(5-pyrimidinyl)pyridin-2-ylamino]aniline (Reference Example 22) and 4-(4-ethylpiperazin-1-ylmethyl)-3-trifluoromethylbenzoyl chloride dihydrochloride (Reference Example 5) were used, and that the resulting crude crystals were washed with ethyl acetate.

Pale Yellow Crystals
Melting point: 256-258° C. (with decomposition)

Example 25

4-(4-ethylpiperazin-1-ylmethyl)-3-trifluoromethyl-N-{4-methyl-3-[4-(5-pyrimidinyl)pyridin-2-ylamino]phenyl}benzamide hydrochloride This compound was prepared in the same manner as in Example 2, except that 4-(4-ethylpiperazin-1-ylmethyl)-3-trifluoromethyl-N-{4-methyl-3-[4-(5-pyrimidinyl)pyridin-2-ylamino]phenyl}benzamide (Example 24) was used.

Colorless Crystals
Melting point: 254-256° C. (with decomposition)
Elemental analysis (for $C_{31}H_{32}F_3N_7O.HCl.0.6H_2O$)
Calcd. (%): C, 59.77; H, 5.53; N, 15.74.
Found (%): C, 59.63; H, 5.34; N, 15.63.

Example 26

4-(4-ethylpiperazin-1-ylmethyl)-3-trifluoromethyl-N-{4-methyl-3-[4-(3-pyridyl)pyridin-2-ylamino]phenyl}benzamide 200 mg of 4-methyl-3-[4-(3-pyridyl)pyridin-2-ylamino]aniline (Reference Example 23) was suspended in 4 ml of acetonitrile, and 78.8 mg of 4-(dimethylamino)pyridine and 484 µl of N,N-diisopropyl-N-ethylamine were added in turn. Under ice-cooling with stirring, 383 mg of 4-(4-ethylpiperazin-1-ylmethyl)-3-trifluoromethylbenzoyl chloride dihydrochloride (Reference Example 5) was added, followed by stirring at room temperature for 2 hours. To the reaction solution was added water and the mixture was subjected to extraction with ethyl acetate three times. The organic layers were washed with saturated saline and dried over anhydrous magnesium sulfate, and then the solvent was distilled off under reduced pressure. The residue was purified by silica gel column chromatography to obtain 93 mg of the objective compound as pale yellow crystals.
Melting point: 227-229° C. (with decomposition)

Example 27

4-(4-ethylpiperazin-1-ylmethyl)-3-trifluoromethyl-N-{4-methyl-3-[4-(3-pyridyl)pyridin-2-ylamino]phenyl}benzamide hydrochloride This compound was prepared in the same manner as in Example 2, except that 4-(4-ethylpiperazin-1-ylmethyl)-3-trifluoromethyl-N-{4-methyl-3-[4-(3-pyridyl)pyridin-2-ylamino]phenyl}benzamide (Example 26) was used.

Colorless Crystals
  Melting point: 230-235° C. (with decomposition)
  Elemental analysis (for $C_{32}H_{33}F_3N_6O.HCl$)
  Calcd. (%): C, 62.89; H, 5.61; N, 13.75.
  Found (%): C, 63.30; H, 5.70; N, 13.65.

Example 28

4-(4-methylpiperazin-1-ylmethyl)-3-trifluoromethyl-N-{4-methyl-3-[4-(3-pyridyl)pyridin-2-ylamino]phenyl}benzamide This compound was prepared in the same manner as in Example 26, except that 4-(4-methylpiperazin-1-ylmethyl)-3-trifluoromethylbenzoyl chloride dihydrochloride (Reference Example 2) was used, and that extraction was conducted five times with chloroform and the resulting crude crystals obtained by purification with silica gel column chromatography were washed with ethyl acetate.

Pale Yellow Crystals
  Melting point: 241-242° C. (with decomposition)
  Elemental analysis (for $C_{31}H_{31}F_3N_6O.0.4H_2O$)
  Calcd. (%): C, 65.57; H, 5.64; N, 14.80.
  Found (%): C, 65.31; H, 5.70; N, 14.90.

Example 29

4-(4-methylpiperazin-1-ylmethyl)-3-trifluoromethyl-N-{4-methyl-3-[4-(3-pyridyl)pyridin-2-ylamino]phenyl}benzamide methanesulfonate 1.21 g of 4-(4-methylpiperazin-1-ylmethyl)-3-trifluoromethyl-N-{4-methyl-3-[4-(3-pyridyl)pyridin-2-ylamino]phenyl}benzamide (Example 28) was suspended in 20 ml of methanol and 140 μl of methanesulfonic acid was added, followed by stirring with heating. Insolubles were removed by filtration with heating and the solvent in the filtrate was distilled off under reduced pressure. The residue was crystallized by adding isopropanol and collected by filtration to obtain 1.33 g of the objective compound as pale yellow crystals.
  Melting point: 189-191° C.
  Elemental analysis (for $C_{31}H_{31}F_3N_6O.0.3SO_3H.0.3H_2O$)
  Calcd. (%): C, 58.05; H, 5.42; N, 12.69.
  Found (%): C, 58.05; H, 5.30; N, 12.71.

Example 30

4-(1-methylpiperazin-4-ylmethyl)-3-trifluoromethyl-N-{4-methyl-3-[6-(3-pyridyl)pyrimidin-4-ylamino]phenyl}benzamide This compound was prepared in the same manner as in Example 1, except that 4-methyl-3-[6-(3-pyridyl)pyrimidin-4-ylamino]aniline (Reference Example 20) and 4-(4-methylpiperazin-1-ylmethyl)-3-trifluoromethylbenzoyl chloride dihydrochloride (Reference Example 2) were used, and that the reaction was conducted at room temperature for 92 hours and the resulting crude crystals were washed with ethyl acetate.

Colorless Crystals
  Melting point: 253-254° C. (with decomposition)

Example 31

4-(1-methylpiperazin-4-ylmethyl)-3-trifluoromethyl-N-{4-methyl-3-[6-(3-pyridyl)pyrimidin-4-ylamino]phenyl}benzamide hydrochloride This compound was prepared in the same manner as in Example 2, except that 4-(1-methylpiperazin-4-ylmethyl)-3-trifluoromethyl-N-{4-methyl-3-[6-(3-pyridyl)pyrimidin-4-ylamino]phenyl}benzamide (Example 30) was used, and that the resulting crude crystals were washed in turn with ethanol and diethyl ether.

Pale Yellow Crystals
  Melting point: 190-194° C. (with decomposition)
  Elemental analysis (for $C_{30}H_{30}F_3N_7O.HCl.2.5H_2O$)
  Calcd. (%): C, 56.03; H, 5.64; N, 15.25.
  Found (%): C, 55.67; H, 5.76; N, 15.11.

Example 32

4-(1-methylpiperazin-4-ylmethyl)-3-trifluoromethyl-N-{4-methyl-3-[6-(5-pyrimidinyl)pyrimidin-4-ylamino]phenyl}benzamide This compound was prepared in the same manner as in Example 1, except that 4-methyl-3-[6-(5-pyrimidinyl)pyrimidin-4-ylamino]aniline (Reference Example 21) and 4-(4-methylpiperazin-1-ylmethyl)-3-trifluoromethylbenzoyl chloride dihydrochloride (Reference Example 2) were used, and that the reaction was conducted at room temperature for 17 hours and the resulting crude crystals were washed with ethyl acetate.

Pale Yellow Crystals
  Melting point: 257-267° C. (with decomposition)

Example 33

4-(1-methylpiperazin-4-ylmethyl)-3-trifluoromethyl-N-{4-methyl-3-[6-(5-pyrimidinyl)pyrimidin-4-ylamino]phenyl}benzamide hydrochloride This compound was prepared in the same manner as in Example 2, except that 4-(1-methylpiperazin-4-ylmethyl)-3-trifluoromethyl-N-{4-methyl-3-[6-(5-pyrimidinyl)pyrimidin-4-ylamino]phenyl}benzamide (Example 32) was used, and that the resulting crude crystals were washed in turn with ethanol and diethyl ether.

Pale Yellow Crystals
  Melting point: 203-207° C. (with decomposition)
  Elemental analysis (for $C_{29}H_{29}F_3N_8O.HCl.4H_2O$)
  Calcd. (%): C, 51.90; H, 5.71; N, 16.70.
  Found (%): C, 52.50; H, 5.68; N, 16.24.

Example 34

4-[4-(2-fluoroethyl)piperazin-1-ylmethyl]-3-trifluoromethyl-N-{4-methyl-3-[4-(5-pyrimidinyl)pyrimidin-2-ylamino]phenyl}benzamide Under an argon atmosphere, 1.71 g of 4-[4-(2-fluoroethyl)piperazin-1-ylmethyl]-3-trifluoromethylbenzoic acid (Reference Example 14) was dissolved in 14 ml of anhydrous N,N-dimethylformamide and 1.56 g of 2-chloro-1-methylpyridinium iodide was added, followed by stirring at room temperature for 10 minutes. 1.50 g of 4-methyl-3-[4-

(5-pyrimidinyl)pyrimidin-2-ylamino]aniline (Reference Example 18) and 1.13 ml of N,N-diisopropyl-N-ethylamine were added in turn, followed by stirring at room temperature for 1 hour. 300 ml of water was added to the reaction solution, followed by extraction with ethyl acetate. Two hundred ml of saturated sodium hydrogen carbonate was added to the aqueous layer and the mixture was further extracted with ethyl acetate. The organic layers were combined and dried over anhydrous magnesium sulfate, and the solvent was distilled off under reduced pressure. The residue was purified by column chromatography and the crude crystals were washed with diethyl ether-ethyl acetate to obtain 1.68 g of the objective compound as pale yellow crystals.

Melting point: 207-209° C. (with decomposition)

Example 35

4-[4-(2-fluoroethyl)piperazin-1-ylmethyl]-3-trifluoromethyl-N-{4-methyl-3-[4-(5 yrimidinyl)pyrimidin-2-ylamino]phenyl}benzamide hydrochloride This compound was prepared in the same manner as in Example 2, except that 4-[4-(2-fluoroethyl)piperazin-1-ylmethyl]-3-trifluoromethyl-N-{4-methyl-3-[4-(5-pyrimidinyl)pyrimidin-2-ylamino]phenyl}benzamide (Example 34) was used, and that the resulting crude crystals were washed with ethanol.

Pale Yellow Crystals

Melting point: 213-233° C. (with decomposition)
Elemental analysis (for $C_{30}H_{30}F_4N_8O.HCl.0.2H_2O$)
Calcd. (%): C, 56.77; H, 4.99; N, 17.66.
Found (%): C, 56.62; H, 4.99; N, 17.77

Example 36

4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide Step 1

4-[4-[2-(t-butyldimethylsilanoxy)ethyl]piperazin-1-ylmethyl]-3-trifluoromethyl-N-{4-methyl-3-[4-(5-pyrimidinyl)pyrimidin-2-ylamino]phenyl}benzamide This compound was prepared in the same manner as in Example 34, except that 4-{4-[2-(t-butyldimethylsilanoxy)ethyl]piperazin-1-ylmethyl}-3-trifluoromethylbenzoic acid (Reference Example 15) was used, and that the resulting amorphous obtained by purification with column chromatography was crystallized from diethyl ether-ethyl acetate.

Pale Yellow Crystals

Melting point: 193-198° C. (with decomposition)

Step 2

4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide 2.03 g of 4-{4-[2-(t-butyldimethylsilanoxy)ethyl]piperazin-1-ylmethyl}-3-trifluoromethyl-N-{4-methyl-3-[4-(5-pyrimidinyl)pyrimidin-2-ylamino]phenyl}benzamide obtained in the step 1 was dissolved in 25 ml of anhydrous tetrahydrofuran, followed by stirring under ice-cooling. 5.74 ml of tetrabutyl ammonium fluoride (1M solution in tetrahydrofuran) was added, and the mixture was stirred for 5 minutes, then stirred at room temperature for 22 hours. The reaction solution was diluted with ethyl acetate and washed with water. The washed aqueous layer was subjected to extraction with ethyl acetate four times. The organic layers were combined and dried over anhydrous magnesium sulfate, and then the solvent was distilled off under reduced pressure. The residue was purified by silica gel column chromatography to obtain 890 mg of the objective compound as pale yellow crystals.

Melting point: 188-192° C.

Example 37

4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide (Example 36) was used.

Pale Yellow Crystals

Melting point: 248-255° C. (with decomposition)
Elemental analysis (for $C_{30}H_{31}F_3N_8O_2.HCl.0.2H_2O$)
Calcd. (%): C, 56.95; H, 5.16; N, 17.71.
Found (%): C, 56.80; H, 5.06; N, 17.71.

Example 38

(+)-4-[(R)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide hydrochloride Step 1

4-[(R)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 34, except that 4-[(R)-3-(dimethylamino)pyrrolidin-1-ylmethyl]-3-trifluoromethylbenzoic acid (Reference Example 12) was used, and that after water and an aqueous saturated sodium hydrogen carbonate solution were added to the reaction solution, the mixture was stirred, and then the deposited crystals were collected by filtration and washed with water.

Yellow Crystals

Step 2

(+)-4-[(R)-3-(dimethylamino)pyrrolidin-1-ylmethyl]-3-trifluoromethyl-N-{4-methyl-3-[4-(5-pyrimidinyl)pyrimidin-2-ylaminol]phenyl}benzamide hydrochloride This compound was prepared in the same manner as in Example 2, except that 4-[(R)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide obtained in the step 1 was used, and that the resulting crude crystals were washed in turn with diisopropyl ether and diethyl ether.

Pale Yellow Crystals
Melting point: 178° C. (with decomposition)
$[\alpha]_D^{20}$: +9.75° (c=1.025, methanol)
Elemental analysis (for $C_{30}H_{31}F_3N_8O \cdot HCl \cdot 1.5H_2O$)
Calcd. (%): C, 56.29; H, 5.51; N, 17.51.
Found (%): C, 56.11; H, 5.43; N, 17.60.

Example 39

4-(1-piperazinylmethyl)-3-trifluoromethyl-N-{3-[4-(5-bromopyridin-3-yl)pyrimidin-2-ylamino]-4-methylphenyl}benzamide Step 1

4-[4-(t-butoxycarbonyl)piperazin-1-ylmethyl]-3-trifluoromethyl-N-{3-[4-(5-bromopyridin-3-yl)pyrimidin-2-ylamino]-4-methylphenyl}benzamide This compound was prepared in the same manner as in Example 34, except that 4-[4-(t-butoxycarbonyl)piperazin-1-ylmethyl]-3-trifluoromethylbenzoic acid (Reference Example 13) and 3-[4-(5-bromopyridin-3-yl)pyrimidin-2-ylamino]-4-methylaniline (Reference Example 19) were used.

Pale Yellow Crystals

Step 2

4-(1-piperazinylmethyl)-3-trifluoromethyl-N-{3-[4-(5-bromopyridin-3-yl)pyrimidin-2-ylamino]-4-methylphenyl}benzamide To 214 mg of 4-[4-(t-butoxycarbonyl)piperazin-1-ylmethyl]-3-trifluoromethyl-N-{3-[4-(5-bromopyridin-3-yl)pyrimidin-2-ylamino]-4-methylphenyl}benzamide obtained in the step 1 was added 1.5 ml of trifluoroacetic acid, followed by stirring at room temperature for 1 hour. The mixture was alkalified (pH 9) by adding 10 ml of a 10% aqueous sodium hydroxide solution to the reaction solution, extracted twice with ethyl acetate, and then dried over anhydrous magnesium sulfate. The solvent was distilled off under reduced pressure. The residue was purified by silica gel column chromatography and the crude product was crystallized from diethyl ether-ethyl acetate to obtain 99 mg of the objective compound as pale yellow crystals.

Melting point: 195-197° C. (with decomposition)

Example 40

4-(1-piperazinylmethyl)-3-trifluoromethyl-N-{3-[4-(5-bromopyridin-3-yl)pyrimidin-2-ylamino]-4-methylphenyl}benzamide hydrochloride This compound was prepared in the same manner as in Example 2, except that 4-(1-piperazinylmethyl)-3-trifluoromethyl-N-{3-[4-(5-bromopyridin-3-yl)pyrimidin-2-ylamino]-4-methylphenyl}benzamide (Example 39) was used, and that the resulting amorphous was crystallized by adding chloroform-diethyl ether-methanol.

Pale Yellow Crystals
Melting point: 176-182° C. (with decomposition)
Elemental analysis (for $C_{29}H_{27}BrF_3N_7O \cdot HCl \cdot 1.5H2O$)
Calcd. (%): C, 50.48; H, 4.53; N, 14.21.
Found (%): C. 50.25; H, 4.21; N, 13.91.

Example 41

4-(1-piperazinylmethyl)-3-trifluoromethyl-N-{4-methyl-3-[4-(3-pyridyl)pyridin-2-ylamino]phenyl}benzamide Step 1

4-[4-(t-butoxycarbonyl)piperazin-1-ylmethyl]-3-trifluoromethyl-N-{4-methyl-3-[4-(3-pyridyl)pyridin-2-ylamino]phenyl}benzamide This compound was prepared in the same manner as in Example 34, except that 4-[4-(t-butoxycarbonyl)piperazin-1-ylmethyl]-3-trifluoromethylbenzoic acid (Reference Example 13) and 4-methyl-3-[4-(3-pyridyl)pyridin-2-ylamino]aniline (Reference Example 23) were used, and that the resulting crude crystals obtained by purification with silica gel column chromatography were recrystallized from n-hexane-ethyl acetate.

Step 2

4-(1-piperazinylmethyl)-3-trifluoromethyl-N-{4-methyl-3-[4-(3-pyridyl)pyridin-2-ylamino]phenyl}benzamide This compound was prepared in the same manner as in Example 39 (Step 2), except that 4-[4-(t-butoxycarbonyl)piperazin-1-ylmethyl]-3-trifluoromethyl-N-{4-methyl-3-[4-(3-pyridyl)pyridin-2-ylamino]phenyl}benzamide obtained in the step 1 was used.

Example 42

4-(1-piperazinylmethyl)-3-trifluoromethyl-N-{4-methyl-3-[4-(3-pyridyl)pyridin-2-ylamino]phenyl}benzamide hydrochloride This compound was prepared in the same manner as in Example 2, except that 4-(1-piperazinylmethyl)-3-trifluoromethyl-N-{4-methyl-3-[4-(3-pyridyl)pyridin-2-ylamino]phenyl}benzamide (Example 41) was used, and that the resulting amorphous was crystallized by adding isopropanol.

Pale Yellow Crystals
Melting point: 190-195° C. (with decomposition)
Elemental analysis (for $C_{30}H_{29}F_3N_6O \cdot HCl \cdot 0.36(CH_3)CHOH \cdot 1.9H_2O$)
Calcd. (%): C, 57.64; H, 5.89; N, 13.40.
Found (%): C, 58.02; H, 5.47; N, 12.97.

Example 43

4-(1-piperazinylmethyl)-3-trifluoromethyl-N-{4-methyl-3-[4-(5-pyrimidinyl)pyrimidin-2-ylamino]phenyl}benzamide trifluoroacetate

Step 1

4-[4-(t-butoxycarbonyl)piperazin-1-ylmethyl]-3-trifluoromethyl-N-{4-methyl-3-[4-(5-pyrimidinyl)pyrimidin-2-ylamino]phenyl}benzamide This compound was prepared in the same manner as in Example 34, except that 4-[4-(t-butoxycarbonyl)piperazin-1-ylmethyl]-3-trifluoromethylbenzoic acid (Reference Example 13) was used.

Pale Yellow Crystals

Melting point: 182-186° C. (with decomposition)

Step 2

4-(1-piperazinylmethyl)-3-trifluoromethyl-N-{4-methyl-3-[4-(5-pyrimidinyl)pyrimidin-2-ylamino]phenyl}benzamide trifluoroacetate To 1.54 g of 4-[4-(t-butoxycarbonyl)piperazin-1-ylmethyl]-3-trifluoromethyl-N-{4-methyl-3-[4-(5-pyrimidinyl)pyrimidin-2-ylaminophenyl}benzamide obtained in the step 1 was added 15 ml of trifluoroacetic acid, followed by stirring at room temperature for 1 hour. Trifluoroacetic acid was distilled off under reduced pressure, and then the residue was purified by NH silica gel column chromatography (Chromatorex (Fuji Silysia Chemical Co., Ltd.), chloroform→chloroform/methanol (10/1)). The resulting amorphous was crystallized from ethyl acetate to obtain 1.23 g of the objective compound.

Pale Yellow Crystals

Melting point: 199-202° C. (with decomposition)

Elemental analysis (for $C_{28}H_{27}F_3N_8O \cdot CF_3CO_2H \cdot 2H_2O$)

Calcd. (%): C, 51.58; H, 4.62; N, 16.04.

Found (%): C, 51.71; H, 4.26; N, 16.13.

Example 44

4-(3-carbamoylpiperazin-1-ylmethyl)-3-trifluoromethyl-N-{4-methyl-3-[4-(5-pyrimidinyl)pyrimidin-2-ylamino]phenyl}benzamide

Step 1

4-[4-(t-butoxycarbonyl)-3-carbamoylpiperazin-1-ylmethyl]-3-trifluoromethyl-N-{4-methyl-3-[4-(5-pyrimidinyl)pyrimidin-2-ylamino]phenyl}benzamide This compound was prepared in the same manner as in Example 34, except that 4-[1-(t-butoxycarbonyl)-2-carbamoylpiperazin-4-ylmethyl]-3-trifluoromethylbenzoic acid (Reference Example 16) was used, and that the reaction was conducted at room temperature for 6 hours.

Pale Yellow Crystals

Melting point: 206-209° C. (with decomposition)

Step 2

4-(3-carbamoylpiperazin-1-ylmethyl)-3-trifluoromethyl-N-{4-methyl-3-[4-(5-pyrimidinyl)pyrimidin-2-ylamino]phenyl}benzamide To 1.52 g of 4-[4-(t-butoxycarbonyl)-3-carbamoylpiperazin-1-ylmethyl]-3-trifluoromethyl-N-{4-methyl-3-[4-(5-pyrimidinyl)pyrimidin-2-ylamino]phenyl}benzamide obtained in the step 1 was added 6.0 ml of trifluoroacetic acid, followed by stirring at room temperature for 1 hour. Trifluoroacetic acid was distilled off under reduced pressure, and the residue was dissolved in ethyl acetate, washed in turn with an aqueous saturated sodium hydrogen carbonate solution and water, and dried over anhydrous magnesium sulfate. The solvent was distilled off under reduced pressure, and then the residue was purified by silica gel column chromatography to obtain 963 mg of the objective compound as pale yellow crystals.

Melting point: 235-238° C.

Example 45

4-(3-carbamoylpiperazin-1-ylmethyl)-3-trifluoromethyl-N-{4-methyl-3-[4-(5-pyrimidinyl)pyrimidin-2-ylamino]phenyl}benzamide hydrochloride

This compound was prepared in the same manner as in Example 2, except that 4-(3-carbamoylpiperazin-1-ylmethyl)-3-trifluoromethyl-N-{4-methyl-3-[4-(5-pyrimidinyl)pyrimidin-2-ylamino]phenyl}benzamide (Example 44) was used.

Pale Yellow Crystals

Melting point: 205-208° C.

Elemental analysis (for $C_{29}H_{28}F_3N_9O_2 \cdot HCl \cdot 1.3H_2O$)

Calcd. (%): C, 53.47; H, 4.89; N, 19.35.

Found (%): C, 53.11; H, 4.92; N, 19.79.

Example 46

(−)-4-((S)-3-amino-2-oxopyrrolidin-1-ylmethyl)-3-trifluoromethyl-N-{4-methyl-3-[4-(5-pyrimidinyl)pyrimidin-2-ylamino]phenyl}benzamide

Step 1

4-[(S)-3-(t-butoxycarbonylamino)-2-oxopyrrolidin-1-ylmethyl]-3-trifluoromethyl-N-{4-methyl-3-[4-(5-pyrimidinyl)pyrimidin-2-ylamino]phenyl}benzamide Eight hundred mg of 4-[(S)-3-(t-butoxycarbonylamino)-2-oxopyrrolidin-1-ylmethyl]-3-trifluoromethylbenzoic acid (Reference Example 17) was dissolved in 7 ml of anhydrous N,N-dimethylformamide, and 0.67 ml of N,N-diisopropyl-N-ethylamine and 1.00 g of 1H-benzotriazol-1-yloxytripyrrolidinophosphonium hexafluorophosphate (PyBOP) were added in turn, followed by stirring at room temperature for 30 minutes. 4-Methyl-3-[4-(5-pyrimidinyl)pyrimidin-2-ylamino]aniline (Reference Example 18) was added and the mixture was stirred at room temperature for 18 hours. The reaction solution was diluted with water, followed by extraction with ethyl acetate. The organic layer was washed in turn with an aqueous saturated sodium hydrogen carbonate solution and water, and then dried over anhydrous magnesium sulfate. The solvent was distilled off under reduced pressure and the residue was purified by silica gel column chromatography to obtain 453 mg of the objective compound as a pale yellow amorphous.

Step 2

(−)-4-((S)-3-amino-2-oxopyrrolidin-1-ylmethyl)-3-trifluoromethyl-N-{4-methyl-3-[4-(5-pyrimidinyl)pyrimidin-2-ylamino]phenyl}benzamide 439 mg of 4-[(S)-3-(t-butoxycarbonylamino)-2-oxopyrrolidin-1-ylmethyl]-3-trifluoromethyl-N-{4-methyl-3-[4-(5-pyrimidinyl)pyrimidin-2-ylamino]phenyl}benzamide obtained in the step 1 was added 2.0 ml of trifluoroacetic acid, followed by stirring at room temperature for 1 hour. Trifluoroacetic acid was distilled off under reduced pressure, and then the residue was dissolved in water and washed with diethyl ether. The mixture was alkalified by adding an aqueous saturated sodium hydrogen carbonate solution to the aqueous layer, followed by extraction with chloroform twice, and dried over anhydrous magnesium sulfate. The solvent was distilled off under reduced pressure, and then the residue was purified by silica gel column chromatography, crystallized by adding ethyl acetate to the resulting amorphous and collected by filtration to obtain 244 mg of the objective compound as yellow crystals.

Melting point: 156-159° C. (with decomposition)
$[\alpha]_D^{20}$: −26.13° (c=0.352, methanol)
Elemental analysis (for $C_{28}H_{25}F_3N_8O.5CH_3CO_2C_2H_5.0.5H_2O$)
Calcd. (%): C, 58.53; H, 4.91; N, 18.20.
Found (%): C, 58.99; H, 4.88; N, 17.76.

Example 47

4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide To a solution of 6.00 g of 4-(bromomethyl)-3-trifluoromethyl-N-{4-methyl-3-[4-(5-pyrimidinyl)pyrimidin-2-ylamino]phenyl}benzamide (Reference Example 31) in 60 ml of anhydrous N,N-dimethylformamide were added 1.51 g of (S)-(−)-3-(dimethylamino)pyrrolidine and 1.83 g of potassium carbonate, followed by stirring at room temperature for 14 hours. To the reaction solution were added water and an aqueous saturated sodium hydrogen carbonate solution, and the mixture was extracted with ethyl acetate and dried over anhydrous magnesium sulfate. The solvent was distilled off under reduced pressure and the residue was purified by silica gel column chromatography to obtain 4.57 g of pale yellow crystals.

Melting point: 179-183° C. (with decomposition)

Example 48

(−)-4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide (Example 47) was used, and that the resulting crude crystals were washed with isopropanol.

Pale Yellow Crystals
Melting point: 154-158° C. (with decomposition)
$[\alpha]_D^{20}$: −10.25° (c=0.546, methanol)
Elemental analysis (for $C_{30}H_{31}F_3N_8O.HCl.2.5H_2O$)
Calcd. (%): C, 54.75; H, 5.67; N, 17.03.
Found (%): C, 54.72; H, 5.38; N, 16.96.

Example 49

4-(3-carbamoyl-4-methylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 47, except that 1-methylpiperazin-2-carboxamide dihydrochloride (Reference Example 24) was used, and that potassium carbonate was used in an amount of 10 equivalents based on a raw material.

Pale Yellow Crystals
Melting point: 248-253° C.

Example 50

4-(3-carbamoyl-4-methylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-(3-carbamoyl-4-methylpiperazin-1-ylmethyl)-3-trifluoromethyl-N-{4-methyl-3-[4-(5-pyrimidinyl)pyrimidin-2-ylamino]phenyl}benzamide (Example 49) was used.

Pale Yellow Crystals
Melting point: 203-208° C.
Elemental analysis (for $C_{30}H_{30}F_3N_9O_2.HCl.1.7H_2O$)
Calcd. (%): C, 53.56; H, 5.15; N, 18.74.
Found (%): C, 53.53; H, 4.98; N, 18.46.

Example 51

4-[(S)-2-(1-pyrrolidinylmethyl)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (S)-(+)-2-(1-pyrrolidinylmethyl)pyrrolidine was used.

Pale Yellow Crystals
Melting point: 147-152° C. (with decomposition)

Example 52

(−)-4-[(S)-2-(1-pyrrolidinylmethyl)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-2-(1-pyrrolidinylmethyl)pyrrolidin-1-ylmethyl]-3-trifluoromethyl-N-{4-methyl-3-[4-(5-pyrimidinyl)pyrimidin-2-ylamino]phenyl}benzamide (Example 51) was used.
Pale Yellow Amorphous
$[\alpha]_D^{20}$: −11.00° (c=0.509, methanol)
Elemental analysis (for $C_{33}H_{35}F_3N_8O \cdot HCl \cdot 0.5H_2O$)
Calcd. (%): C, 59.86; H, 5.63; N, 16.92.
Found (%): C, 59.66; H, 5.89; N, 16.61.

Example 53

4-[3-(dimethylaminomethyl)azetidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that 3-(dimethylaminomethyl)azetidine dihydrochloride (Reference Example 25) was used, and that potassium carbonate was used in an amount of 5 equivalents based on a raw material.
Yellow Crystals
Melting point: 174-181° C. (with decomposition)

Example 54

4-[3-(dimethylaminomethyl)azetidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[3-(dimethylaminomethyl)azetidin-1-ylmethyl]-3-trifluoromethyl-N-{4-methyl-3-[4-(5-pyrimidinyl)pyrimidin-2-ylamino]phenyl}benzamide (Example 53) was used.
Pale Yellow Crystals
Melting point: 142-152° C. (with decomposition)
Elemental analysis (for $C_{30}H_{31}F_3N_8O \cdot HCl \cdot H_2O$)
Calcd. (%): C, 57.10; H, 5.43; N, 17.76.
Found (%): C, 57.41; H, 5.79; N, 17.53.

Example 55

4-((S)-3-methylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 47, except that (S)-(+)-2-methylpiperazine was used.
Yellow Crystals
Melting point: 193-196° C.

Example 56

(+)-4-((R)-3-methylpiperazin-1-ylmethyl)-3-trifluoromethyl-N-{4-methyl-3-[4-(5-pyrimidinyl)pyrimidin-2-ylamino]phenyl}benzamide hydrochloride Step 1

4-((R)-3-methylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 47, except that (R)-(−)-2-methylpiperazine was used.
Pale Yellow Crystals Step 2

(+)-4-((R)-3-methylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-((R)-3-methylpiperazin-1-ylmethyl)-3-trifluoromethyl-N-{4-methyl-3-[4-(5-pyrimidinyl)pyrimidin-2-ylamino]phenyl}benzamide obtained in the step 1 was used.
Yellow Crystals
Melting point: 254-258° C.
$[\alpha]_D^{20}$: +9.63° (c=0.498, methanol)
Elemental analysis (for $C_{29}H_{29}F_3N_8O \cdot HCl \cdot 0.3C_2H_5OH \cdot H_2O$)
Calcd. (%): C, 55.85; H, 5.46; N, 17.97.
Found (%): C, 55.93; H, 5.33; N, 18.08.

Example 57

(−)-4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide hydrochloride Step 1

4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (S)-3-(N,N-diethylamino)pyrrolidine dihydrochloride (Reference Example 26) was used, and that potassium carbonate was used in an amount of 6 equivalents based on a raw material.
Pale Yellow Crystals Step 2

(−)-4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide obtained in the step 1 was used.
Pale Yellow Crystals
Melting point: 200-202° C.
$[\alpha]_D^{20}$: −9.74° (c=0.513, methanol)
Elemental analysis (for $C_{32}H_{35}F_3N_8O \cdot HCl \cdot 2.5H_2O$)
Calcd. (%): C, 56.01; H, 6.02; N, 16.33.
Found (%): C, 56.27; H, 5.94; N, 15.96.

Example 58

(−)-4-[(S)-3-(1-pyrrolidinyl)pyrrolidin-1-ylmethyl]-3-trifluoromethyl-N-{4-methyl-3-[4-(5-pyrimidinyl)pyrimidin-2-ylamino]phenyl}benzamide hydrochloride Step 1

4-[(S)-3-(1-pyrrolidinyl)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (S)-3-(1-pyrrolidinyl)pyrrolidine hydrochloride (Reference Example 27) was used, and that potassium carbonate was used in an amount of 3.8 equivalents based on a raw material.

Yellow Crystals

Step 2

(−)-4-[(S)-3-(1-pyrrolidinyl)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-3-(1-pyrrolidinyl)pyrrolidin-1-ylmethyl]-3-trifluoromethyl-N-{4-methyl-3-[4-(5-pyrimidinyl)pyrimidin-2-ylamino]phenyl}benzamide obtained in the step 1 was used.

Yellow Crystals

Melting point: 168-171° C.

$[\alpha]_D^{20}$: 12.20° (c=1.016, methanol)

Elemental analysis (for $C_{32}H_{33}F_3N_8O \cdot HCl \cdot 3H_2O$)

Calcd. (%): C, 55.45; H, 5.82; N, 16.17.

Found (%): C, 55.44; H, 5.48; N, 16.06.

Example 59

4-[(3S,4S)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide hydrochloride Step 1

4-[(3S,4S)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (3S,4S)-3-(dimethylamino)-4-methoxypyrrolidine dihydrochloride (Reference Example 28) was used, and that potassium carbonate was used in an amount of, 5 equivalents based on a raw material.

Pale Yellow Crystals

Melting point: 187-190° C. (with decomposition)

Step 2

4-[(3S,4S)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(3S,4S)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide obtained in the step 1 was used. The crude crystals were washed with isopropanol.

Pale Yellow Crystals

Melting point: 155-161° C. (with decomposition)

Elemental analysis (for $C_{31}H_{33}F_3N_8O \cdot HCl \cdot 0.2i\text{-}PrOH \cdot 1.5H_2O$)

Calcd. (%): C, 55.64; H, 5.70; N, 16.43.

Found (%): C, 55.59; H, 5.37; N, 16.69.

Example 60

(−)-4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide hydrochloride Step 1

4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (2R,4S)-4-(dimethylamino)-2-methylpyrrolidine dihydrochloride (Reference Example 29) was used, and that potassium carbonate was used in an amount of 5 equivalents based on a raw material.

Pale Yellow Crystals

Step 2

(−)-4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide obtained in the step 1 was used.

Yellow Crystals

Melting point: 188-193° C.

$[\alpha]_D^{20}$: −51.87° (c=0.347, methanol)

Elemental analysis (for $C_{31}H_{33}F_3N_8O \cdot HCl \cdot 0.5C_2H_5OH \cdot 2H_2O$)

Calcd. (%): C, 55.23; H, 6.13; N, 16.62.

Found (%): C, 55.42; H, 6.10; N, 16.96.

Example 61

4-((S)-3-aminopiperidinomethyl)-3-trifluoromethyl-N-{4-methyl-3-[4-(5-pyrimidinyl)pyrimidin-2-ylamino]phenyl}benzamide Step 1

4-[(S)-3-(t-butoxycarbonylamino)piperidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (S)-(−)-3-(t-butoxycarbonylamino)piperidine (Synthetic Communications, 1998, 28, 3919-3926) was used.

Pale Yellow Amorphous

Step 2

4-((S)-3-aminopiperidinomethyl)-3-trifluoromethyl-N-{4-methyl-3-[4-(5-pyrimidinyl)pyrimidin-2-ylamino]phenyl}benzamide This compound was prepared in the same manner as in Example 46 (Step 2), except that 4-[(S)-3-(t-butoxycarbonylamino)piperidin-1-ylmethyl]-3-trifluoromethyl-N-{4-methyl-3-[4-(5-pyrimidinyl)pyrimidin-2-ylamino]phenyl}benzamide obtained in the step 1 was used, and that extraction was conducted with a mixed solution of chloroform-methanol (10:1), the solvent was distilled off, and then the resulting crude crystals were washed with diethyl ether.

Pale Yellow Crystals
Melting point: 163-167° C.

Example 62

(+)-4-((S)-3-aminopiperidinomethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-((S)-3-aminopiperidinomethyl)-3-trifluoromethyl-N-{4-methyl-3-[4-(5-pyrimidinyl)pyrimidin-2-ylamino]phenyl}benzamide (Example 61) was used.

Pale Yellow Crystals
Melting point: 193-199° C.
$[\alpha]_D^{20}$: +28.31° (c=0.438, methanol)
Elemental analysis (for $C_{29}H_{29}F_3N_8O \cdot HCl \cdot 2.1H_2O$)
Calcd. (%): C, 54.69; H, 5.41; N, 17.59.
Found (%): C, 54.33; H, 5.40; N, 18.05.

Example 63

4-[(S)-3-(dimethylamino)piperidinomethyl]-3-trifluoromethyl-N-{4-methyl-3-[4-(5-pyrimidinyl)pyrimidin-2-ylamino]phenyl}benzamide To a suspension of 1.47 g of 4-((S)-3-aminopiperidinomethyl)-3-trifluoromethyl-N-{4-methyl-3-[4-(5-pyrimidinyl)pyrimidin-2-ylamino]phenyl}benzamide (Example 61) in 30 ml of methanol were added in turn 3 ml of acetic acid, 2 ml of a 37% aqueous formaldehyde solution and 1.66 g of sodium triacetoxy borohydride, followed by stirring at room temperature for 14 hours. The mixture was alkalified by adding an aqueous saturated sodium hydrogen carbonate solution to the reaction solution, extracted with ethyl acetate twice. The organic layers were combined, washed with water, and dried over anhydrous magnesium sulfate, and then the solvent was distilled off under reduced pressure. The residue was purified by silica gel column chromatography to obtain 0.62 g of the objective compound as pale yellow crystals.

Melting point: 160-162° C.

Example 64

(+)-4-[(S)-3-(dimethylamino)piperidinomethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-3-(dimethylamino)piperidinomethyl]-3-trifluoromethyl-N-{4-methyl-3-[4-(5-pyrimidinyl)pyrimidin-2-ylamino]phenyl}benzamide (Example 63) was used, and that the resulting crude crystals were washed with acetone.

Pale Yellow Crystals
Melting point: 195-198° C.
$[\alpha]_D^{20}$: +15.92° (c=0.314, methanol)
Elemental analysis (for $C_{31}H_{33}F_3N_8O \cdot HCl \cdot 2H_2O$)
Calcd. (%): C, 56.15; H, 5.78; N, 16.90.
Found (%): C, 55.45; H, 5.80; N, 17.30.

Example 65

4-((3S,4R)-3-amino-4-methylpyrrolidin-1-ylmethyl)-3-trifluoromethyl-N-{4-methyl-3-[4-(5-pyrimidinyl)pyrimidin-2-ylamino]phenyl}benzamide Step 1

4-[(3S,4R)-3-(t-butoxycarbonyl)amino-4-methylpyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (3S,4R)-3-(t-butoxycarbonyl)amino-4-methylpyrrolidine (Tetrahedron: Asymmetry, 1997, 8, 883-887) was used.

Pale Yellow Crystals
Melting point: 191-201° C.

Step 2

4-((3S,4R)-3-amino-4-methylpyrrolidin-1-ylmethyl)-3-trifluoromethyl-N-{4-methyl-3-[4-(5-pyrimidinyl)pyrimidin-2-ylamino]phenyl}benzamide This compound was prepared in the same manner as in Example 46 (Step 2), except that 4-[(3S,4R)-3-(t-butoxycarbonyl)amino-4-methylpyrrolidin-1-ylmethyl]-3-trifluoromethyl-N-{4-methyl-3-[4-(5-pyrimidinyl)pyrimidin-2-ylamino]phenyl}benzamide obtained in the step 1 was used, and that extraction was conducted with a mixed solution of chloroform-methanol (10:1).

Pale Yellow Crystals
Melting point: 148-155° C. (with decomposition)

Example 66

4-[(3S,4R)-3-(dimethylamino)-4-methylpyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 63, except that 4-((3S,4R)-3-amino-4-methylpyrrolidin-1-ylmethyl)-3-trifluoromethyl-N-{4-methyl-3-[4-(5-pyrimidinyl)pyrimidin-2-ylamino]phenyl}benzamide (Example 65) was used.

Pale Yellow Crystals
Melting point: 153-156° C. (with decomposition)

Example 67

(−)-4-[(3S,4R)-3-(dimethylamino)-4-methylpyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(3S,4R)-3-(dimethylamino)-4-methylpyrrolidin-1-ylmethyl]-3-trifluoromethyl-N-{4-methyl-3-[4-(5-pyrimidinyl)pyrimidin-2-ylamino]phenyl}benzamide (Example 66) was used.

Pale Yellow Crystals
Melting point: 164-174° C. (with decomposition)
$[\alpha]_D^{20}$: −2.43° (c=0.493, methanol)
Elemental analysis (for $C_{31}H_{33}F_3N_8O.HCl.0.5H_2O$)
Calcd. (%): C, 58.53; H, 5.55; N, 17.62.
Found (%): C, 58.50; H, 5.73; N, 17.38.

Example 68

(−)-4-[(S)-3-(methylamino)pyrrolidin-1-ylmethyl]-3-trifluoromethyl-N-{4-methyl-3-[4-(5-pyrimidinyl)pyrimidin-2-ylamino]phenyl}benzamide Step 1

4-{(S)-3-[N-(t-butoxycarbonyl)-N-methylamino]pyrrolidin-1-ylmethyl}-3-trifluoromethyl-N-{4-methyl-3-[4-(5-pyrimidinyl)pyrimidin-2-ylamino]phenyl}benzamide This compound was prepared in the same manner as in Example 47, except that (S)-3-[N-(t-butoxycarbonyl)-N-methylamino]pyrrolidine (Reference Example 30) was used.

Yellow Crystals

Step 2

(−)-4-[(S)-3-(methylamino)pyrrolidin-1-ylmethyl]-3-trifluoromethyl-N-{4-methyl-3-[4-(5-pyrimidinyl)pyrimidin-2-ylamino]phenyl}benzamide 0.99 g of 4-{(S)-3-[N-(t-butoxycarbonyl)-N-methylamino]pyrrolidin-1-ylmethyl}-3-trifluoromethyl-N-{4-methyl-3-[4-(5-pyrimidinyl)pyrimidin-2-ylamino]phenyl}benzamide obtained in the step 1 was dissolved in 15 ml of dichloromethane and 10 ml of trifluoroacetic acid was added, followed by stirring at room temperature for 1 hour. The reaction solution was neutralized with a 20% aqueous sodium hydroxide solution and followed by extraction with ethyl acetate. The organic layer was washed with saturated saline and dried over anhydrous magnesium sulfate, and then the solvent was distilled off under reduced pressure. The residue was purified by silica gel column chromatography to obtain 0.70 g of the objective compound as flesh-colored crystals.

Melting point: 142-149° C. (with decomposition)
$[\alpha]_D^{20}$: −7.14° (c=1.007, methanol)
Elemental analysis (for $C_{29}H_{29}F_3N_8O.HCl.0.6H_2O$)
Calcd. (%): C, 66.75; H, 5.31; N, 19.54.
Found (%): C, 66.78; H, 5.30; N, 19.37.

Example 69

(−)-4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide hydrochloride Step 1

4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 63, except that 4-((S)-3-methylpiperazin-1-ylmethyl)-3-trifluoromethyl-N-{4-methyl-3-[4-(5-pyrimidinyl)pyrimidin-2-ylamino]phenyl}benzamide (Example 55) was used.

Yellow Crystals

Step 2

(−)-4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide obtained in the step 1 was used.

Yellow Crystals
Melting point: 187-193° C.
$[\alpha]_D^{20}$: −5.27° (c=0.379, methanol)
Elemental analysis (for $C_{30}H_{31}F_3N_8O.HCl.2.6H_2O$)
Calcd. (%): C, 54.60; H, 5.68; N, 16.98.
Found (%): C, 54.46; H, 5.46; N, 16.81.

Example 70

4-((R)-3,4-dimethylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 63, except that 4-((R)-3-methylpiperazin-1-ylmethyl)-3-trifluoromethyl-N-{4-methyl-3-[4-(5-pyrimidinyl)pyrimidin-2-ylamino]phenyl}benzamide (Example 56 (Step 1)) was used.

Yellow Powder
  Melting point: 246-249° C. (with decomposition)

Example 71

(+)-4-((R)-3,4-dimethylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-((R)-3,4-dimethylpiperazin-1-ylmethyl)-3-trifluoromethyl-N-{4-methyl-3-[4-(5-pyrimidinyl)pyrimidin-2-ylamino]phenyl}benzamide (Example 70) was used.

Pale Yellow Crystals
  Melting point: 186-194° C.
  $[\alpha]_D^{20}$: +5.42° (c=0.369, methanol)
  Elemental analysis (for $C_{30}H_{31}F_3N_8O.HCl.0.4C_2H_5OH.2H_2O$)
  Calcd. (%): C, 54.77; H, 5.88; N, 17.04.
  Found (%): C, 55.04; H, 5.65; N, 16.74.

Example 72

4-{4-[(5-methyl-2-oxo-1,3-dioxol-4-yl)methyl]piperazin-1-ylmethyl}-3-trifluoromethyl-N-{4-methyl-3-[4-(5-pyrimidinyl)pyrimidin-2-ylamino]phenyl}benzamide Step 1

4-(bromomethyl)-5-methyl-1,3-dioxol-2-one

To 403 mg of 4-(chloromethyl)-5-methyl-1,3-dioxol-2-one and 525 mg of sodium bromide was added 0.8 ml of anhydrous N,N-dimethylformamide, followed by at room temperature for 1.5 hours. To the reaction solution was added 1.2 ml anhydrous acetone, the mixture was further stirred at room temperature for 1 hour, and then insolubles were removed by filtration. Insolubles were washed three times with 0.8 ml of anhydrous acetone, and the resulting pale yellow solution was used in the next reaction.

Step 2

4-{4-[(5-methyl-2-oxo-1,3-dioxol-4-yl)methyl]piperazin-1-ylmethyl}-3-trifluoromethyl-N-{4-methyl-3-[4-(5-pyrimidinyl)pyrimidin-2-ylamino]phenyl}benzamide To a suspension of 1.22 g of 4-(piperazin-1-ylmethyl)-3-trifluoromethyl-N-{4-methyl-3-[4-(5-pyrimidinyl)pyrimidin-2-ylamino]phenyl}benzamide (Reference Example 32) in 5 ml of anhydrous N,N-dimethylformamide was added 222 mg of potassium hydrogen carbonate, and a solution of 4-(bromomethyl)-5-methyl-1,3-dioxol-2-one obtained in the step 1 in acetone was added dropwise under stirring at room temperature. After stirring at room temperature for 10 hours, the reaction solution was diluted with water and followed by extraction with ethyl acetate five times. The organic layers were washed with water, and dried over anhydrous magnesium sulfate, and then the solvent was distilled off under reduced pressure. The residue was purified by silica gel column chromatography to obtain 1.00 g of the objective compound as a pale yellow amorphous.

Example 73

4-{4-[(5-methyl-2-oxo-1,3-dioxol-4-yl)methyl]piperazin-1-ylmethyl}-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-{4-[(5-methyl-2-oxo-1,3-dioxol-4-yl)methyl]piperazin-1-ylmethyl}-3-trifluoromethyl-N-{4-methyl-3-[4-(5-pyrimidinyl)pyrimidin-2-ylamino]phenyl}benzamide (Example 72) was used, and that the resulting crude crystals were washed with methanol.

Pale Yellow Crystals
  Melting point: 218-226° C. (with decomposition)
  Elemental analysis (for $C_{33}H_{31}F_3N_8O_4.HCl.3H_2O$)
  Calcd. (%): C, 56.86; H, 4.63; N, 16.07.
  Found (%): C, 56.55; H, 4.70; N, 16.14.

Example 74

4-(4-methylpiperazin-1-ylmethyl)-3-trifluoromethyl-N-{4-methyl-3-[4-(4-pyridyl)thiazol-2-ylamino]phenyl}benzamide To 697 mg of 4-(4-methylpiperazin-1-ylmethyl)-3-trifluoromethyl-N-[4-methyl-3-(thioureido)phenyl]benzamide (Reference Example 33) were added in turn 3 ml of ethanol, 1.5 ml of water and 1.5 ml of 1 N hydrochloric acid, and the mixture was heated in an oil bath at 65° C. 6 ml of an aqueous solution of 421 mg of 4-(bromoacetyl)pyridine hydrobromide (J. Heterocycl. Chem., 1970, 7, 1137-1141) was added thereto, and the mixture was stirred for 2 hours. After air-cooling the reaction solution, the reaction solution was diluted with water, alkalified by adding an aqueous saturated sodium hydrogen carbonate solution, followed by extraction with ethyl acetate and dried over anhydrous magnesium sulfate. Then, the solvent was distilled off under reduced pressure, and the residue was purified by silica gel column chromatography to obtain 701 mg of the objective compound as colorless crystals.
  Melting point: 226-227° C.

Example 75

4-(4-methylpipiperazin-1-ylmethyl)-3-trifluoromethyl-N-{4-methyl-3-[4-(4-pyridyl)thiazol-2-ylamino]phenyl}benzamide hydrochloride This compound was prepared in the same manner as in Example 2, except that 4-(4-methylpiperazin-1-ylmethyl)-3-trifluoromethyl-N-{4-methyl-3-[4-(4-pyridyl)thiazol-2-ylamino]phenyl}benzamide (Example 74) was used.

Pale Yellow Crystals
  Melting point: 186-188° C.
  Elemental analysis (for $C_{29}H_{29}F_3N_6OS\ HCl\ H_2O$)
  Calcd. (%): C, 56.08; H, 5.19; N, 13.53.
  Found (%): C, 56.37; H, 5.26; N, 13.25.

Example 76

4-[3-(dimethylamino)azetidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that 3-(dimethylamino)azetidine dihydrochloride (Reference Example 34) was used, and that potassium carbonate was used in an amount of 5 equivalents based on a raw material.

Yellow Crystals
  Melting point: 169-173° C. (with decomposition)

Example 77

4-[3-(dimethylamino)azetidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[3-(dimethylamino)azetidin-1-ylmethyl]-3-trifluoromethyl-N-{4-methyl-3-[4-(5-pyrimidinyl)pyrimidin-2-ylamino]phenyl}benzamide (Example 76) was used.

Pale Yellow Crystals
  Melting point: 159-167° C. (with decomposition)
  Elemental analysis (for $C_{29}H_{29}F_3N_8O \cdot HCl \cdot H_2O$)
  Calcd. (%): C, 56.45; H, 5.23; N, 18.16.
  Found (%): C, 56.35; H, 5.04; N, 17.90.

Example 78

4-[(R)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (S)-3-(dimethylaminomethyl)pyrrolidine dihydrochloride (Reference Example 35) was used, and that potassium carbonate was used in an amount of 5 equivalents based on a raw material.

Yellow Crystals
  Melting point: 159-164° C. (with decomposition)

Example 79

4-[(R)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(R)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide (Example 78) was used, and that the crude crystals were washed with isopropanol.

Pale Yellow Crystals
  Melting point: 114-122° C. (with decomposition)
  Elemental analysis (for $C_{31}H_{33}F_3N_8O \cdot HCl \cdot 0.5i\text{-}PrOH \cdot 0.5H_2O$)
  Calcd. (%): C, 58.61; H, 5.97; N, 16.67.
  Found (%): C, 58.73; H, 5.87; N, 16.31.

Example 80

4-[(S)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (R)-3-(dimethylaminomethyl)pyrrolidine dihydrochloride (Reference Example 36) was used, and that potassium carbonate was used in an amount of 5 equivalents based on a raw material.

Yellow Crystals
  Melting point: 158-163° C. (with decomposition)

Example 81

4-[(S)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(S)-3-(dimethylaminomethyl)pyrrolidin-1-ylmethyl]-3-trifluoromethyl-N-{4-methyl-3-[4-(5-pyrimidinyl)pyrimidin-2-ylamino]phenyl}benzamide (Example 80) was used, and that the crude crystals were washed with isopropanol.

Pale Yellow Crystals
  Melting point: 114-122° C. (with decomposition)
  Elemental analysis (for $C_{31}H_{33}F_3N_8O \cdot HCl \cdot 0.5i\text{-}PrOH \cdot 0.2H_2O$)
  Calcd. (%): C, 59.08; H, 5.86; N, 16.96.
  Found (%): C, 59.02; H, 5.79; N, 16.62.

Example 82

4-[(3R,4R)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide This compound was prepared in the same manner as in Example 47, except that (3R,4R)-3-(dimethylamino)-4-methoxypyrrolidine dihydrochloride (Reference Example 37) was used, and that potassium carbonate was used in an amount of 5 equivalents based on a raw material.

Pale Yellow Crystals
  Melting point: 185-188° C.

Example 83

4-[(3R,4R)-3-(dimethylamino)-4-methoxpyrrolidin-1-ylmethyl]-3-trifluoromethyl-N-{4-methyl-3-[4-(5-pyrimidinyl)pyrimidin-2-ylamino]phenyl}benzamide hydrochloride This compound was prepared in the same manner as in Example 2, except that 4-[(3R,4R)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide (Example 82) was used, and that the crude crystals were washed with isopropanol.

Pale Yellow Crystals
  Melting point: 166-170° C.
  Elemental analysis (for $C_{31}H_{33}F_3N_8O \cdot HCl \cdot 1.5H_2O$)
  Calcd. (%): C, 55.56; H, 5.57; N, 16.72.
  Found (%): C, 55.53; H, 5.19; N, 16.77.

Example 84

4-(1-methylpiperidin-4-yloxy)-3-trifluoromethyl-N-{4-methyl-3-[4-(3-pyridyl)pyrimidin-2-ylamino]phenyl}benzamide This compound was prepared in the same manner as in Example 1, except that 4-methyl-3-[4-(3-pyridyl)pyrimidin-2-ylamino]aniline (Patent Document 1) and 4-(1-methylpiperidin-4-yloxy)-3-trifluoromethylbenzoyl chloride hydrochloride (Reference Example 11) were used.

Example 85

4-(1-methylpiperidin-4-ylidenemethyl)-3-trifluoromethyl-N-{4-methyl-3-[4-(3-pyridyl)pyrimidin-2-ylamino]phenyl}benzamide This compound was prepared in the same manner as in Example 1, except that 4-methyl-3-[4-(3-pyridyl)pyrimidin-2-ylamino]aniline (Patent Document 1) and 4-(1-methylpiperidin-4-ylidenemethyl)-3-trifluoromethylbenzoyl chloride hydrochloride (Reference Example 7) were used.

Example 86

4-[(R)-3-(dimethylaminomethyl)pyrrolidin-1-ylmethyl]-3-trifluoromethyl-N-{4-methyl-3-[4-(3-pyridyl)pyrimidin-2-ylamino]phenyl}benzamide This compound was prepared in the same manner as in Example 47, except that 4-(bromomethyl)-3-trifluoromethyl-N-{4-methyl-3-[4-(3-pyridyl)pyrimidin-2-ylamino]phenyl}benzamide (Reference Example 82) and (S)-3-(dimethylaminomethyl)pyrrolidine dihydrochloride (Reference Example 35) were used, and that potassium carbonate was used in an amount of 5 equivalents based on a raw material.

Structural formulas of Examples 1 to 86 are shown in Table 2.

TABLE 2

| Example | Structure Formula |
|---|---|
| 1 | 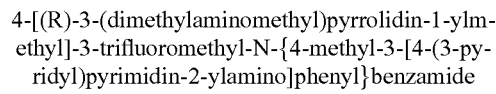 |
| 2 | 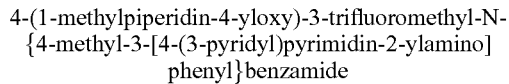 HCl |
| 3 | 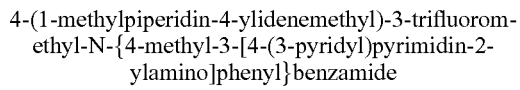 |

TABLE 2-continued

| Example | Structure Formula |
|---------|-------------------|
| 4 | (structure) HCl |
| 5 | (structure) |
| 6 | (structure) HCl |
| 7 | (structure) |
| 8 | (structure) HCl |

TABLE 2-continued
| Example | Structure Formula |
|---|---|
| 9 | 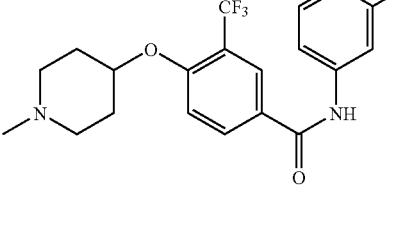 |
| 10 | 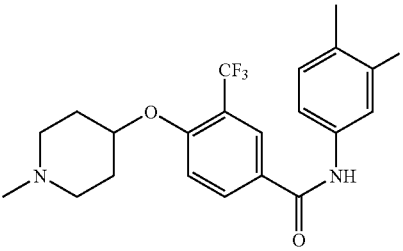 HCl |
| 11 | 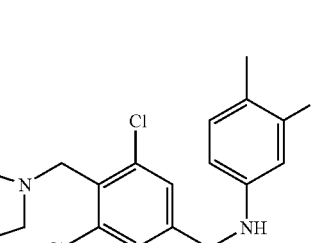 |
| 12 | 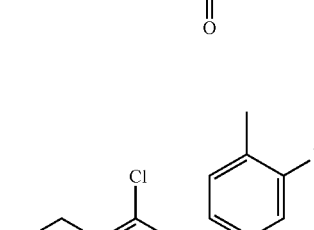 HCl |
| 13 | 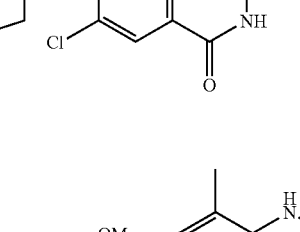 |

TABLE 2-continued
| Example | Structure Formula |
|---|---|
| 14 | 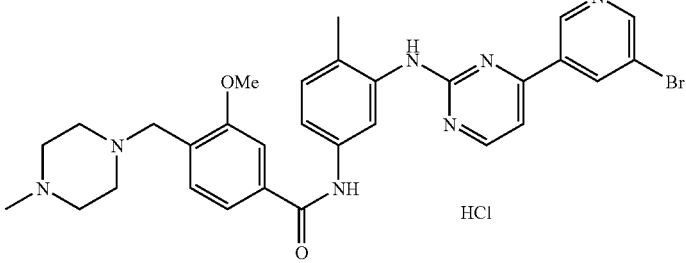 HCl |
| 15 | 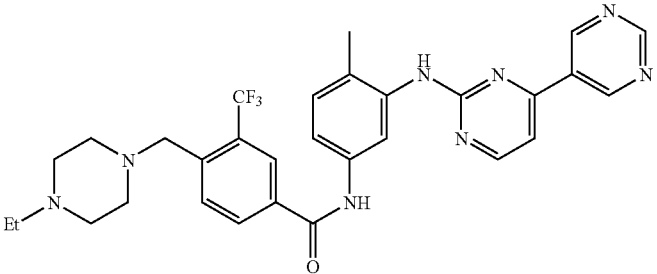 |
| 16 | 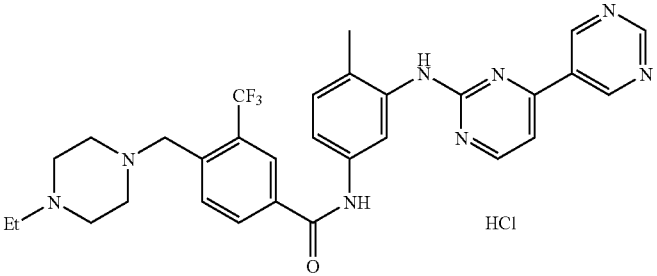 HCl |
| 17 | 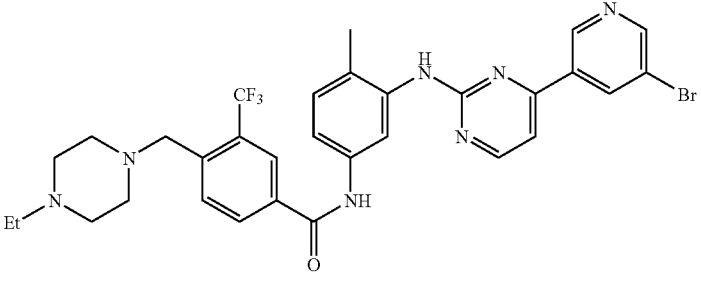 |
| 18 | 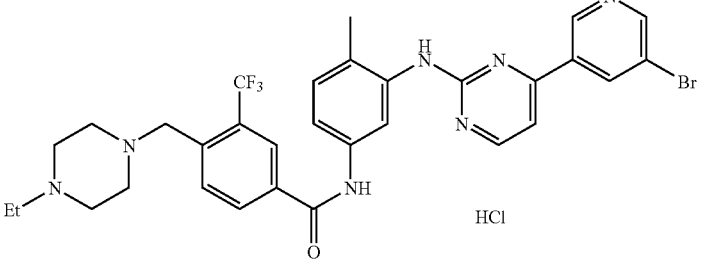 HCl |

TABLE 2-continued

| Example | Structure Formula |
|---|---|
| 19 | |
| 20 | HCl |
| 21 | |
| 22 | |
| 23 | HCl |

TABLE 2-continued

| Example | Structure Formula |
| --- | --- |
| 24 | |
| 25 | HCl |
| 26 | |
| 27 | HCl |
| 28 | |

TABLE 2-continued
| Example | Structure Formula |
|---|---|
| 29 | 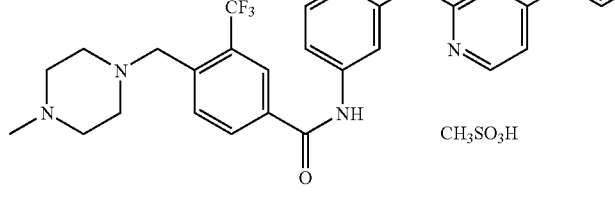 CH₃SO₃H |
| 30 | 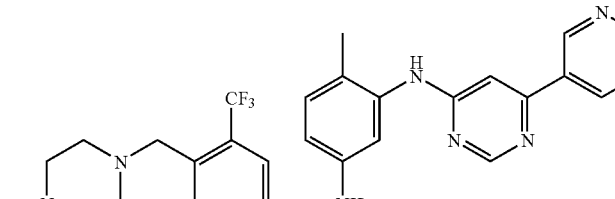 |
| 31 | 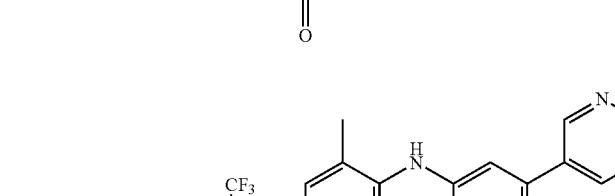 HCl |
| 32 | 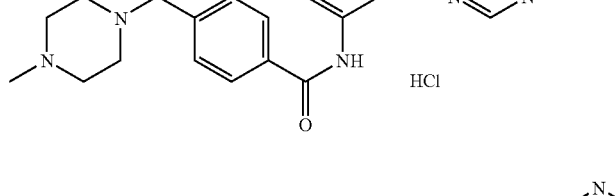 |
| 33 | 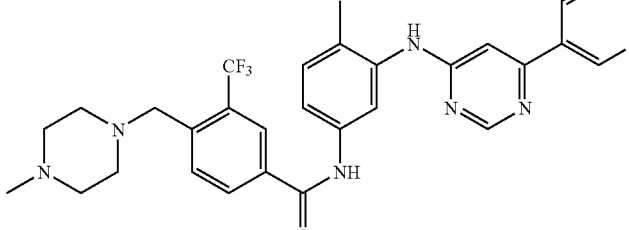 HCl |

TABLE 2-continued
| Example | Structure Formula |
|---|---|
| 34 | 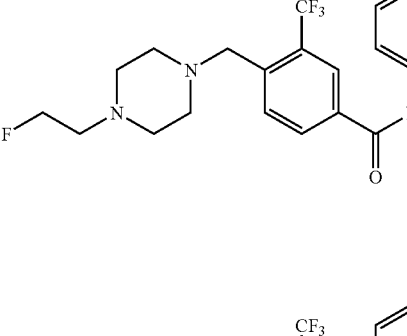 |
| 35 | 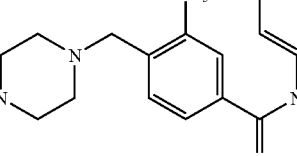 HCl |
| 36 | 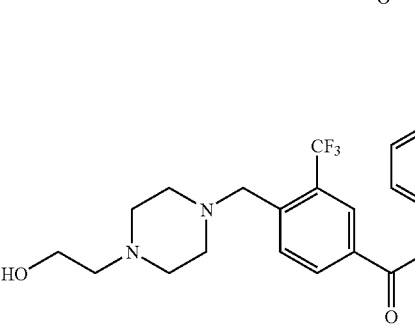 |
| 37 | 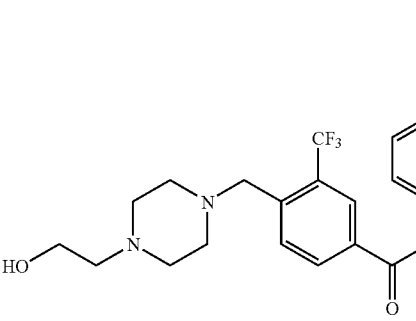 HCl |
| 38 | 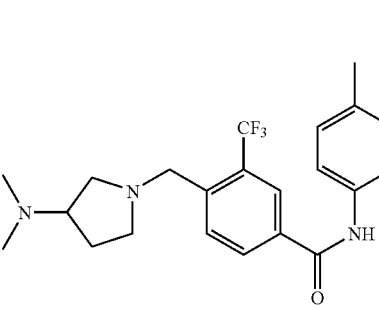 HCl |

TABLE 2-continued

| Example | Structure Formula |
| --- | --- |
| 39 | (structure) |
| 40 | (structure) HCl |
| 41 | (structure) |
| 42 | (structure) HCl |
| 43 | (structure) CF₃CO₂H |

TABLE 2-continued
| Example | Structure Formula |
|---|---|
| 44 | 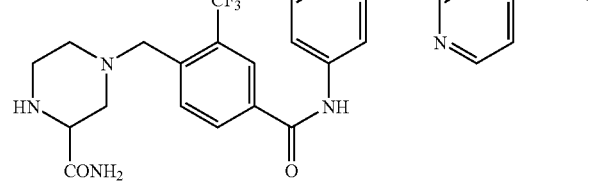 |
| 45 | 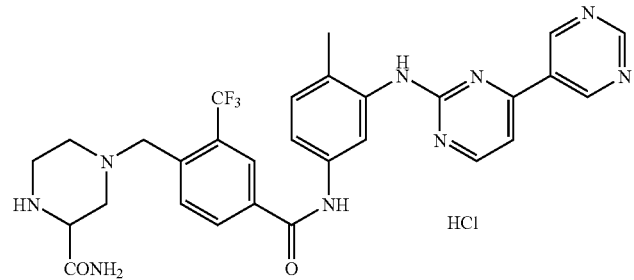 HCl |
| 46 | 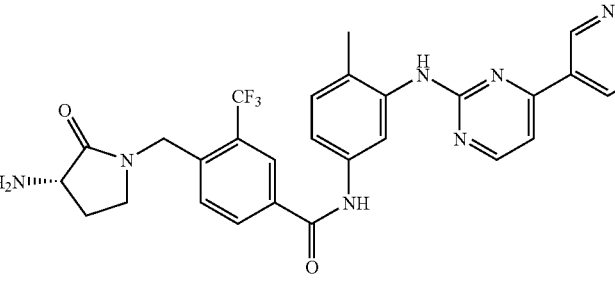 |
| 47 | 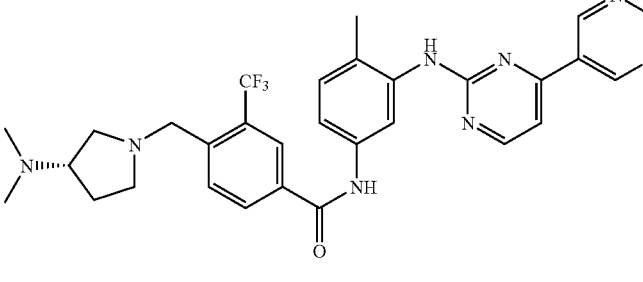 |
| 48 | 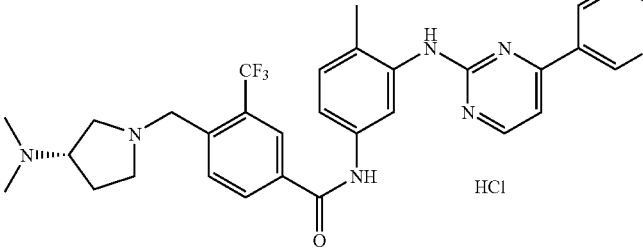 HCl |

TABLE 2-continued

| Example | Structure Formula |
|---|---|
| 49 | |
| 50 | |
| 51 | |
| 52 | |
| 53 | |

TABLE 2-continued
| Example | Structure Formula |
|---|---|
| 54 | 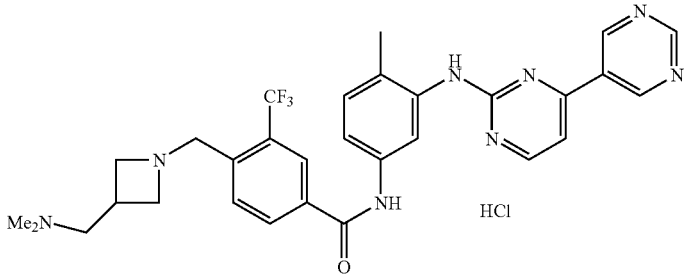 HCl |
| 55 | 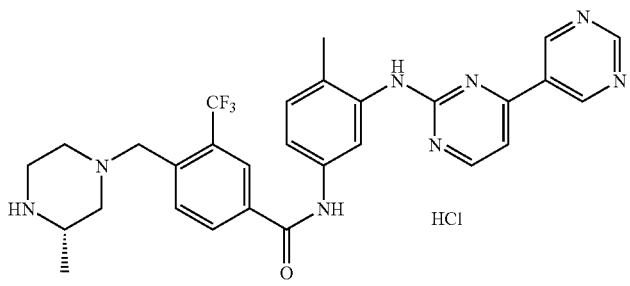 HCl |
| 56 | 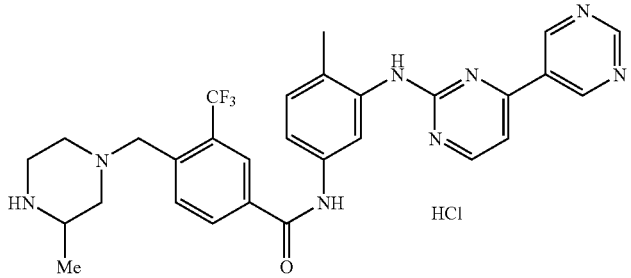 HCl |
| 57 | 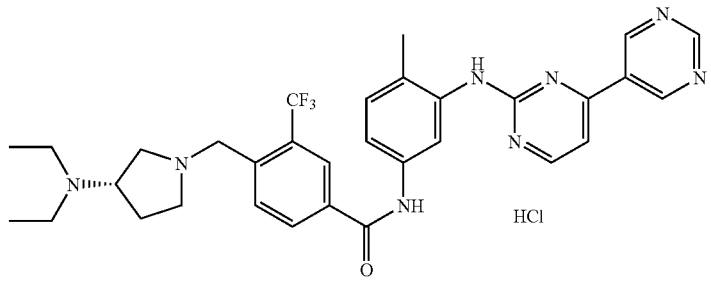 HCl |
| 58 | 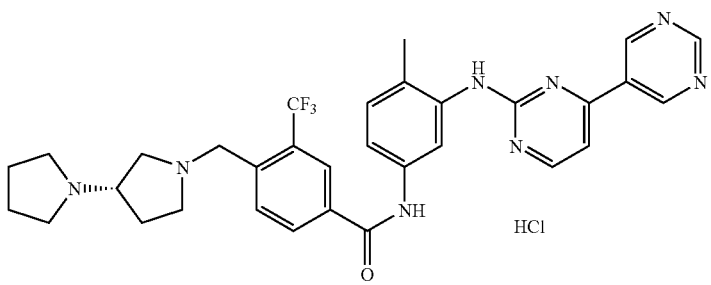 HCl |

TABLE 2-continued

| Example | Structure Formula |
|---|---|
| 59 | (structure with dimethylamino-methoxy-pyrrolidine, CF3-benzamide, tolyl-NH-pyrimidinyl-pyrimidine) · HCl |
| 60 | (structure with dimethylamino-methyl-pyrrolidine, CF3-benzamide, tolyl-NH-pyrimidinyl-pyrimidine) · HCl |
| 61 | (structure with 3-aminopiperidine, CF3-benzamide, tolyl-NH-pyrimidinyl-pyrimidine) |
| 62 | (structure with 3-aminopiperidine, CF3-benzamide, tolyl-NH-pyrimidinyl-pyrimidine) · HCl |
| 63 | (structure with 3-dimethylaminopiperidine, CF3-benzamide, tolyl-NH-pyrimidinyl-pyrimidine) |

TABLE 2-continued

| Example | Structure Formula |
| --- | --- |
| 64 | (structure shown) HCl |
| 65 | (structure shown) |
| 66 | (structure shown) |
| 67 | (structure shown) HCl |
| 68 | (structure shown) |

TABLE 2-continued
| Example | Structure Formula |
|---|---|
| 69 | 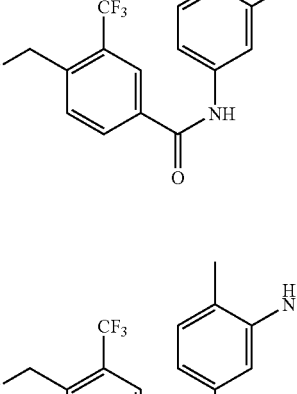 HCl |
| 70 | 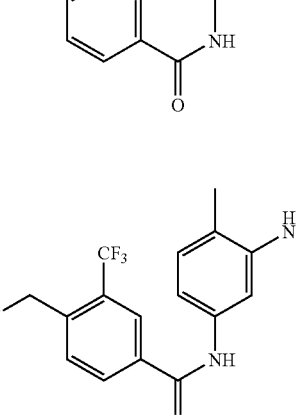 |
| 71 | 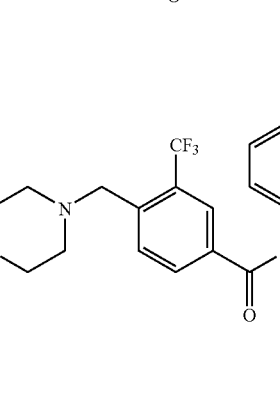 HCl |
| 72 | 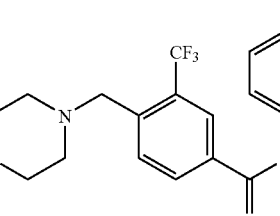 |
| 73 | HCl |

TABLE 2-continued

| Example | Structure Formula |
|---|---|
| 74 | |
| 75 | HCl |
| 76 | |
| 77 | HCl |
| 78 | |

TABLE 2-continued

| Example | Structure Formula |
|---|---|
| 79 | (structure: 4-[[(3R)-3-(dimethylaminomethyl)pyrrolidin-1-yl]methyl]-3-trifluoromethyl-N-[4-methyl-3-[[4-(pyrimidin-5-yl)pyrimidin-2-yl]amino]phenyl]benzamide · HCl) |
| 80 | (structure: 4-[[(3R)-3-(dimethylaminomethyl)pyrrolidin-1-yl]methyl]-3-trifluoromethyl-N-[4-methyl-3-[[4-(pyrimidin-5-yl)pyrimidin-2-yl]amino]phenyl]benzamide) |
| 81 | (structure: 4-[[(3S)-3-(dimethylaminomethyl)pyrrolidin-1-yl]methyl]-3-trifluoromethyl-N-[4-methyl-3-[[4-(pyrimidin-5-yl)pyrimidin-2-yl]amino]phenyl]benzamide · HCl) |
| 82 | (structure: 4-[[(3R,4R)-3-dimethylamino-4-methoxypyrrolidin-1-yl]methyl]-3-trifluoromethyl-N-[4-methyl-3-[[4-(pyrimidin-5-yl)pyrimidin-2-yl]amino]phenyl]benzamide) |
| 83 | (structure: 4-[[(3R,4R)-3-dimethylamino-4-methoxypyrrolidin-1-yl]methyl]-3-trifluoromethyl-N-[4-methyl-3-[[4-(pyrimidin-5-yl)pyrimidin-2-yl]amino]phenyl]benzamide · HCl) |

TABLE 2-continued

| Example | Structure Formula |
|---|---|
| 84 | |
| 85 | |
| 86 | |

Test Example 1

Cell Growth Inhibitory Effect

K562 cells and U937 cells (purchased from American Type Culture Collection) were cultured in a RPMI-1640 medium (manufactured by Sigma) containing 10% (v/v) fetal calf serum (FCS) (manufactures by Sigma) (RPMI-1640/FCS). K562 cells and U937 cells were seeded at a density of 5000 cells/100 μl/well and 4000 cells/100 μl/well in each of 96-hole-plate (manufactured by costar), respectively. The plate was incubated in a $CO_2$ incubator overnight. A test drug was prepared with dimethylsulfoxide (DMSO) (manufactured by Nacalai Tesque) in the concentration 1000 times higher than the test concentration (0, 0.00001 to 1 μM). The resulting solution was diluted 500 times in a RPMI-1640/FCS medium and then 100 μl of the diluent was added in a well. The plate was incubated in a $CO_2$ incubator. After 72 hours, 20 μl

| Test drugs | K562 cells (IC$_{50}$ value: μM) | U937 cells (IC$_{50}$ value: nμM) | Ratio (U937 cells/ K562 cells) |
|---|---|---|---|
| Example 20 | 0.0026 | 29 | 11154 |
| Example 21 | 0.0063 | 42 | 6667 |
| Example 23 | 0.0011 | 5.0 | 4545 |

-continued

| Test drugs | K562 cells (IC$_{50}$ value: μM) | U937 cells (IC$_{50}$ value: nμM) | Ratio (U937 cells/ K562 cells) |
|---|---|---|---|
| Example 25 | 0.0018 | 3.8 | 2111 |
| Example 27 | 0.0025 | 2.6 | 1040 |
| Example 29 | 0.0017 | 1.4 | 824 |
| Example 31 | 0.0069 | 2.1 | 304 |
| Example 33 | 0.0084 | 11 | 1310 |
| Example 35 | 0.0034 | 11 | 3235 |
| Example 37 | 0.0014 | 10 | 7143 |
| Example 38 | 0.0019 | 8.9 | 4684 |
| Example 40 | 0.0039 | 4.4 | 1128 |
| Example 42 | 0.0068 | 1.4 | 206 |
| Example 43 | 0.0011 | 3.9 | 3545 |
| Example 45 | 0.0031 | 15 | 4839 |
| Example 46 | 0.019 | 29 | 1526 |
| Example 48 | 0.0040 | 12 | 3000 |
| Example 50 | 0.0046 | 16 | 3478 |
| Example 52 | 0.0040 | 3.9 | 975 |
| Example 54 | 0.0096 | 16 | 1667 |
| Example 55 | 0.0022 | 10 | 4545 |
| Example 56 | 0.0046 | 4.4 | 957 |
| Example 57 | 0.0058 | 5.6 | 966 |
| Example 58 | 0.0047 | 9.4 | 2000 |
| Example 59 | 0.0081 | 13 | 1605 |
| Example 60 | 0.0050 | 4.0 | 800 |
| Example 62 | 0.0014 | 1.6 | 1143 |
| Example 64 | 0.0043 | 3.7 | 860 |

-continued

| Test drugs | K562 cells (IC$_{50}$ value: μM) | U937 cells (IC$_{50}$ value: nμM) | Ratio (U937 cells/ K562 cells) |
|---|---|---|---|
| Example 67 | 0.0077 | 6.5 | 844 |
| Example 68 | 0.0024 | 5.8 | 2417 |
| Example 69 | 0.0022 | 10 | 4545 |
| Example 71 | 0.0061 | 6.7 | 1098 |
| Example 73 | 0.0023 | 9.7 | 4217 |
| Example 75 | 0.0059 | 2.7 | 458 |
| Example 77 | 0.018 | >100 | >13699 |
| Example 79 | 0.0059 | 20 | 4348 |
| Example 81 | 0.0047 | >100 | >27778 |
| Control drugs | 0.15 | 17.8 | 136.9 |

As is apparent from the results shown in Table 3, the compounds of the present invention have cell growth inhibitory effect usually stronger compared to a control drug. Further, K562 cells used in Test Example 1 were BCR-ABL positive cells, which had been collected from pleural effusion in a late chronic myelogenous leukemia patient who had been subjected to acute transformation. U937 cells were malignant BCR-ABL negative cells that had been collected from a patient of histiocytic lymphoma. As is apparent from the cell growth inhibitory ratio (U937 cells/K562 cells), the compounds of the present invention are drugs having higher safety (20 times to 8000 times or more) than a control drug. Furthermore, the compounds of the present invention have also a cell growth inhibitory effect on E255K expressing cells, and therefore it can be expected that they exhibit adequate self-phosphorylation inhibitory effect on mutant kinases that would be found in the future. Accordingly, the compounds of the present invention are very useful as a therapeutic agent for diseases such as chronic myelogenous leukemia, acute lymphoblastic leukemia and acute myelogenous leukemia.

Formulation Example 1

| Tablet (oral tablet) Formulation/tablet (in 80 mg) | |
|---|---|
| Compound of Example 1 | 5.0 mg |
| Corn Starch | 46.6 mg |
| Crystalline cellulose | 24.0 mg |
| Methyl cellulose | 4.0 mg |
| Magnesium stearate | 0.4 mg |

The mixed powder of this composition is compressed by a conventional method and molded to make oral tablets.

Formulation Example 2

| Tablet (oral tablet) Formulation/tablet (in 80 mg) | |
|---|---|
| Compound of Example 2 | 5.0 mg |
| Corn Starch | 46.6 mg |
| Crystalline cellulose | 24.0 mg |
| Methyl cellulose | 4.0 mg |
| Magnesium stearate | 0.4 mg |

The mixed powder of this composition is compressed by a conventional method and molded to make oral tablets.

INDUSTRIAL APPLICABILITY

As described above, since the compound of the present invention is a compound having excellent BCR-ABL tyrosine kinase inhibitory activity, a pharmaceutical composition comprising the compound of the present invention as an active ingredient is useful as a BCR-ABL tyrosine kinase inhibitor, a therapeutic agent for chronic myelogenous leukemia, a therapeutic agent for acute myelogenous leukemia and a therapeutic agent for acute lymphoblastic leukemia for mammals including humans.

The invention claimed is:
1. An amide derivative, which is a compound selected from the group consisting of the following compounds (1) to (37), or a pharmaceutically acceptable salt:
   (1) 3-difluoromethyl-4-(4-methylpiperazin-1-ylmethyl)-N-{4-methyl-3-[4-(5-pyrimidinyl)pyrimidin-2-ylamino]phenyl}benzamide,
   (2) 3-ethyl-4-(4-methylpiperazin-1-ylmethyl)-N-{4-methyl-3-[4-(5-pyrimidinyl)pyrimidin-2-ylamino]phenyl}benzamide,
   (3) 4-(1-methylpiperidin-4-ylmethyl)-3-trifluoromethyl-N-{4-methyl-3-[4-(5-pyrimidinyl)pyrimidin-2-ylamino]phenyl}benzamide,
   (4) 3,5-dichloro-4-[(S)-3-(dimethylamino)pyrrolidin-1-ylmethyl]-N-{4-methyl-3-[4-(5-pyrimidinyl)pyrimidin-2-ylamino]phenyl}benzamide,
   (5) 3-methoxy-4-(4-methylpiperazin-1-ylmethyl)-N-{3-[4-(5-bromopyridin-3-yl)pyrimidin-2-ylamino]-4-methylphenyl}benzamide,
   (6) 4-(4-ethylpiperazin-1-ylmethyl)-3-trifluoromethyl-N-{4-methyl-3-[4-(5-pyrimidinyl)pyrimidin-2-ylamino]phenyl}benzamide,
   (7) 4-(4-ethylpiperazin-1-ylmethyl)-3-trifluoromethyl-N-{3-[4-(5-bromopyridin-3-yl)pyrimidin-2-ylamino]-4-methylphenyl}benzamide,
   (8) 3-chloro-4-(4-methylpiperazin-1-ylmethyl)-N-{4-methyl-3-[4-(5-pyrimidinyl)pyrimidin-2-ylamino]phenyl}benzamide,
   (9) 3-fluoromethyl-4-(1-methylpiperidin-4-ylmethyl)-N-{4-methyl-3-[4-(5-pyrimidinyl)pyrimidin-2-ylamino]phenyl}benzamide,
   (10) 4-(4-methylpiperazin-1-ylmethyl)-3-trifluoromethyl-N-{4-methyl-3-[4-(5-pyrimidinyl)pyridin-2-ylamino]phenyl}benzamide,
   (11) 4-(4-ethylpiperazin-1-ylmethyl)-3-trifluoromethyl-N-{4-methyl-3-[4-(5-pyrimidinyl)pyridin-2-ylamino]phenyl}benzamide,
   (12) 4-(4-ethylpiperazin-1-ylmethyl)-3-trifluoromethyl-N-{4-methyl-3-[4-(3-pyridyl)pyridin-2-ylamino]phenyl}benzamide,
   (13) 4-(4-methylpiperazin-1-ylmethyl)-3-trifluoromethyl-N-{4-methyl-3-[4-(3-pyridyl)pyridin-2-ylamino]phenyl}benzamide,
   (14) 4-[4(2-fluoroethyl)piperazin-1-ylmethyl]-3-trifluoromethyl-N-{4-methyl-3-[4-(5-pyrimidinyl)pyrimidin-2-ylamino]phenyl}benzamide,
   (15) 4-[4-(2-hydroxyethyl)piperazin-1-ylmethyl]-3-trifluoromethyl-N-{4-methyl-3-[4-(5-pyrimidinyl)pyrimidin-2-ylamino]phenyl}benzamide,
   (16) 4-[(R)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide,
   (17) 4-(1-piperazinylmethyl)-3-trifluoromethyl-N-{3-[4-(5-bromopyridin-3yl)pyrimidin-2-ylamino]-4-methylphenyl}benzamide,

(18) 4-(1-piperazinylmethyl)-3-trifluoromethyl-N-{4-methyl-3-[4-(3-pyridyl)pyridin-2-ylamino]phenyl}benzamide,
(19) 4-(1-piperazinylmethyl)-3-trifluoromethyl-N-{4-methyl-3-[4-(5-pyrimidinyl)pyrimidin-2-ylamino]phenyl}benzamide,
(20) 4-(3-carbamoylpiperazin-1-ylmethyl)-3-trifluoromethyl-N-{4-methyl-3-[4-(5-pyrimidinyl)pyrimidin-2-ylamino]phenyl}benzamide,
(21) 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide,
(22) 4-(3-carbamoyl-4-methylpiperazin-1-ylmethyl)-3-trifluoromethyl-N-{4-methyl-3-[4-(5-pyrimidinyl)pyrimidin-2-ylamino]phenyl}benzamide,
(23) 4-((S)-3-methylpiperazin-1-ylmethyl)-3-trifluoromethyl-N-{4-methyl-3-[4-(5-pyrimidinyl)pyrimidin-2-ylamino]phenyl}benzamide,
(24) 4-((R)-3-methylpiperazin-1-ylmethyl)-3-trifluoromethyl-N-{4-methyl-3-[4-(5-pyrimidinyl)pyrimidin-2-ylamino]phenyl}benzamide,
(25) 4-[(S)-3-(N,N-diethylamino)pyrrolidin-1-ylmethyl]-3-trifluoromethyl-N-{4-methyl-3-[4-(5-pyrimidinyl)pyrimidin-2-ylamino]phenyl}benzamide,
(26) 4-[(2R,4S)-4-(dimethylamino)-2-methylpyrrolidin-1-ylmethyl]-3-trifluoromethyl-N-{4-methyl-3-[4-(5-pyrimidinyl)pyrimidin-2-ylamino]phenyl}benzamide,
(27) 4-((S)-3-aminopiperidinomethyl)-3-trifluoromethyl-N-{4-methyl-3-[4-(5-pyrimidinyl)pyrimidinyl-2-ylamino]phenyl}benzamide,
(28) 4-[(S)-3-(dimethylamino)piperidinomethyl]-3-trifluoromethyl-N-{4-methyl-3-[4-(5-pyrimidinyl)pyrimidin-2-ylamino]phenyl}benzamide,
(29) 4-((3S,4R)-3-amino-4-methylpyrrolidin-1-ylmethyl)-3-trifluoromethyl-N-{4-methyl-3-[4-(5-pyrimidinyl)pyrimidin-2-ylamino]phenyl}benzamide,
(30) 4-[(3S,4R)-3-(dimethylamino)-4-methylpyrrolidin-1-ylmethyl]-3-trifluoromethyl-N-{4-methyl-3-[4-(5-pyrimidinyl)pyrimidin-2-ylamino]phenyl}benzamide,
(31) 4-[(S)-3-(methylamino)pyrrolidin-1-ylmethyl]-3-triliuoromethyl-N-{4-methyl-3-[4-(5-pyrimidinyl)pyrimidin-2-ylamino]phenyl}benzamide,
(32) 4-((S)-3,4-dimethylpiperazin-1-ylmethyl)-3-trifluoromethyl-N-{4-methyl-3-[4-(5-pyrimidinyl)pyrimidin-2-ylamino]phenyl}benzamide,
(33) 4-((R)-3,4-dimethylpiperazin-1-ylmethyl)-3-trifluoromethyl-N-{4-methyl-3-[4-(5pyrimidinyl)pyrimidin-2-ylamino]phenyl}benzamide,
(34) 4-[(3R,4R)-3-(dimethylamino)-4-methoxypyrrolidin-1-ylmethyl]-3-trifluoromethyl-N-{4-methyl-3-[4-(5-pyrimidinyl)pyrimidin-2-ylamino]phenyl}benzamide,
(35) 4-(1-methylpiperidin-4-yloxy)-3-trifluoromethyl-N-{4-methyl-3-[4-(3-pyridyl)pyrimidin-2-ylamino]phenyl}benzamide,
(36) 4-(1-methylpiperidin-4-ylidenemethyl)-3-trifluoromethyl-N-{4-methyl-3-[4-(3-pyridyl)pyrimidin-2-ylamino]phenyl}benzamide, and
(37) 4[(R)-3-(dimethylaminomethyl)pyrrolidin-1-ylmethyl]-3-trifluoromethyl-N-{4-methyl-3-[4-(3-pyridyl)pyrimidin-2-ylamino]phenyl}benzamide.

2. The amide derivative according to claim 1, wherein the compound is 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a pharmaceutically acceptable salt.

3. A pharmaceutical composition comprising the amide derivative of claim 1 or 2, or a pharmaceutically acceptable salt thereof as an active ingredient.

4. The pharmaceutical composition according to claim 3, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a pharmaceutically acceptable salt thereof as an active ingredient.

5. A therapeutic agent for chronic myelogenous leukemia comprising the amide derivative of claim 1 or 2, or a pharmaceutically acceptable salt thereof as an active ingredient.

6. The therapeutic agent according to claim 5, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a pharmaceutically acceptable salt thereof as an active ingredient.

7. A therapeutic agent for acute lymphoblastic leukemia comprising the amide derivative of claim 1 or 2, or a pharmaceutically acceptable salt thereof as an active ingredient.

8. The therapeutic agent according to claim 7, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a pharmaceutically acceptable salt thereof as an active ingredient.

9. A therapeutic agent for acute myelogenous leukemia comprising the amide derivative of claim 1 or 2, or a pharmaceutically acceptable salt thereof as an active ingredient.

10. The therapeutic agent according to claim 9, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a pharmaceutically acceptable salt thereof as an active ingredient.

11. A method of treating a subject having chronic myelogenous leukemia comprising administering to the subject an effective amount of the amide derivative of claim 1 or 2, or a salt thereof.

12. The method according to claim 11, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a salt thereof.

13. A method of treating a subject having acute lymphoblastic leukemia comprising administering to the subject an effective amount of the amide derivative of claim 1 or 2, or a salt thereof.

14. The method according to claim 13, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a salt thereof.

15. A method of treating a subject having acute myelogenous leukemia comprising administering to the subject an effective amount of the amide derivative of claim 1 or 2, or a salt thereof.

16. The method according to claim 15, wherein the amide derivative is the compound 4-[(S)-3-(dimethylamino)pyrrolidin-1-ylmethyl]-3-trifluoromethyl-N-{4-methyl-3-[4-(5-pyrimidinyl)pyrimidin-2-ylamino]phenyl}benzamide, or a salt thereof.

* * * * *